US012753450B2

(12) United States Patent
Assennato et al.

(10) Patent No.: US 12,753,450 B2
(45) Date of Patent: Oct. 6, 2026

(54) CORONAVIRUS DETECTION

(71) Applicant: Diagnostics for the Real World, Ltd, San Jose, CA (US)

(72) Inventors: Sonny Michael Assennato, Little Chesterford (GB); Allyson Victoria Ritchie, Little Chesterford (GB)

(73) Assignee: Diagnostics for the Real World, Ltd, San Jose, CA (US)

( * ) Notice: Subject to any disclaimer, the term of this patent is extended or adjusted under 35 U.S.C. 154(b) by 580 days.

(21) Appl. No.: 17/913,914

(22) PCT Filed: Mar. 23, 2021

(86) PCT No.: PCT/IB2021/052400
§ 371 (c)(1),
(2) Date: Sep. 23, 2022

(87) PCT Pub. No.: WO2021/191795
PCT Pub. Date: Sep. 30, 2021

(65) Prior Publication Data

US 2024/0209460 A1 Jun. 27, 2024

(30) Foreign Application Priority Data

Mar. 23, 2020 (GB) ..................................... 2004203
Apr. 6, 2020 (GB) ..................................... 2005062

(51) Int. Cl.
*C12Q 1/70* (2006.01)
*C12Q 1/6844* (2018.01)

(52) U.S. Cl.
CPC ........... *C12Q 1/701* (2013.01); *C12Q 1/6844* (2013.01)

(58) Field of Classification Search
None
See application file for complete search history.

(56) References Cited

U.S. PATENT DOCUMENTS

2021/0102197 A1* 4/2021 Sabeti .................... G16B 40/20

FOREIGN PATENT DOCUMENTS

| | | | |
|---|---|---|---|
| CN | 111254228 | B | 9/2020 |
| WO | 2008/090340 | A2 | 7/2008 |
| WO | 2010/015835 | A1 | 2/2010 |
| WO | 2014/140640 | A1 | 9/2014 |
| WO | 02/48164 | A2 | 6/2022 |

OTHER PUBLICATIONS

Lamb et al., "The Lancet Rapid Detection of Novel Coronavirus (COVID-19) by Reverse Transcription-Loop-Mediated sothermal Amplification", Manuscript Draft, The Lancet, (Feb. 24, 2020), pp. 1-19, XP055733471, Retrieved from the Internet: URL:https://www.medrxiv.org/content/10.110 1/2020.02.19.20025155vl [retrieved on Sep. 23, 2020].

Zhang et al., "Rapid Molecular Detection of SARS-CoV-2 (COVID-19) Virus RNA Using Colorimetric LAMP", medRxiv, (Feb. 29, 2020), XP055730127, Retrieved from the Internet: URL:https://www.medrxiv.org/content/10.110 1/2020.02.26.20028373vl [retrieved on Jun. 10, 2021].

Yang et al., "Rapid Detection of SARS-CoV-2 Using Reverse transcription RT-LAMP method", medRxiv, (Mar. 3, 2020), XP055733463, Retrieved from the Internet: URL:https://www.medrxiv.org/content/10.1101/2020.03.02.20030130v2 [retrieved on Jun. 10, 2021].

Breitbach, "Loop Mediated Isothermal Amplification (LAMP)—Lateral Flow Loop mediated isothermal Amplification and Lateral Flow Tips and Tricks for a successful Assay Development", (Mar. 11, 2020, XP055772550, Retrieved from the Internet: URL:https://www.milenia-biotec.com/en/isot hermal-amplification-lateral-flow/ [retrieved on Feb. 4, 2021].

El-Tholoth et al., "A Single and Two-Stage, Closed-Tube, Molecular Test for the 2019 Novel Coronavirus (COVID-19) at Home, Clinic, and Points of Entry", ChemRxiv, 2020, available from https://chemrxiv.org/articles/preprint/ A_Single_ and_Two-Stage_ Closed-Tube Molecular Test for the 2019 Novel Coronavirus -COVID-19_at_Home_Clinic_and_Points_of_Entry/11860137.

Yu et al., "Rapid colorimetric detection of COVID-19 coronavirus using a reverse transcriptional loop-mediated sothermal amplification (RT-LAMP) diagnostic platform: iLACO" See materials and methods, MedRxix, 2020, available from https://www.medrxiv.org/content/10.1101/2020.02.20.20025874vl.article-info.

Osterdahl et al., "Detecting SARS-CoV-2 at Point of Care: Preliminary Data Comparing Loop-Mediated Isothermal Amplification (LAMP) to PCR", available from https://papers.ssm.com/sol3/papers.cfm?abstract_id=3564906.

Broughton et al., "Rapid Detection of 2019 Novel Coronavirus SARS-Co V-2 Using a CRISPR-based DETECTR Lateral Flow Assay ", available from https://www.medrxiv.org/content/10.1101/2020.03.06.20032334v2.

Lu et al., "Development of a Novel Reverse Transcription Loop-Mediated Isothermal Amplification Method for Rapid Detection of SARS-Co V-2", Virologica sinica (2020), vol. 35, pp. 344-347, available from https://link.springer.com/article/10.1007/s 1225 0-020-00218-1 #article-info.

(Continued)

*Primary Examiner* — Laura B Goddard
(74) *Attorney, Agent, or Firm* — Scully, Scott, Murphy & Presser, P.C.

(57) ABSTRACT

Methods for detecting nucleic acid of severe acute respiratory syndrome coronavirus 2 (SARS-CoV-2) are described. The methods comprise amplifying nucleic acid of a sample, or amplifying nucleic acid derived from nucleic acid of the sample, by an isothermal amplification reaction using a forward nucleic acid amplification primer and a reverse nucleic acid amplification primer, wherein each nucleic acid amplification primer hybridises specifically to nucleic acid sequence that is conserved in SARS-CoV-2 nucleic acid, but not in other human coronavirus nucleic acid, or the complement thereof. The methods are particularly useful for point-of-care (ROC) testing. Kits, primers, probes, sets of primers, sets of oligonucleotides, and oligonucleotides, and their use in the methods are also described.

20 Claims, 16 Drawing Sheets

Figure 1:
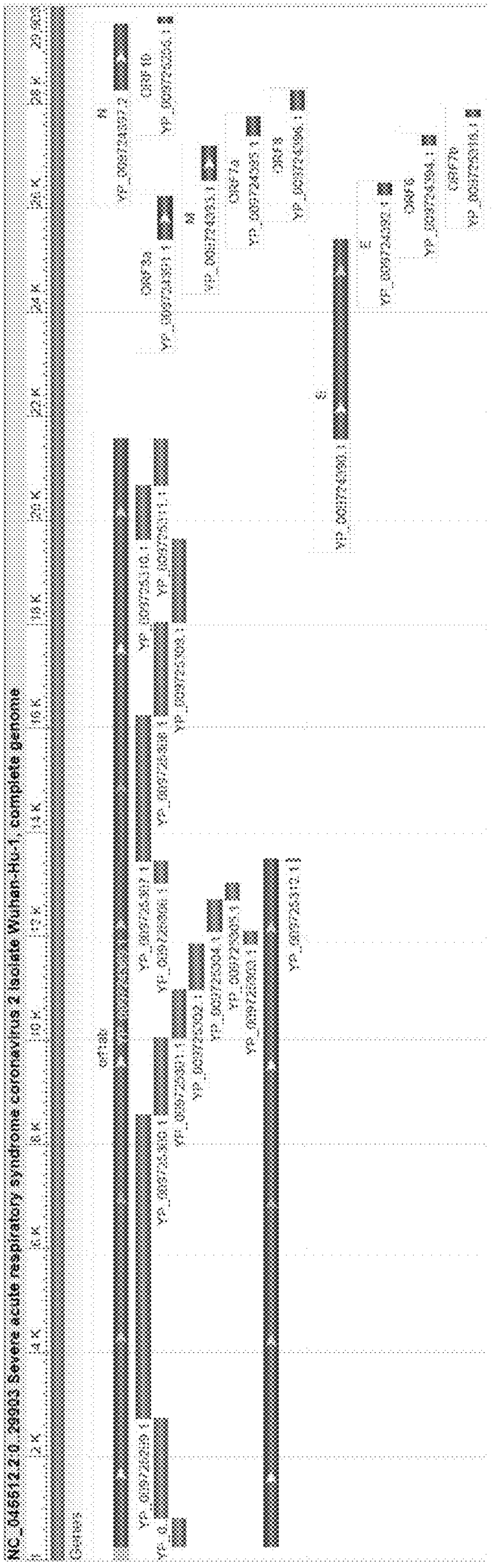

Specification includes a Sequence Listing.

(56) References Cited

OTHER PUBLICATIONS

International Search Report dated Jun. 23, 2021 issued in PCT/IB2021/052400.
GB Search Report dated Jan. 20, 2021 issued in GB 2005062.1.
Altschul S.F. et al., "Basic Local Alignment Search Tool", J. Mol. Biol. 215:403-410 (1990).
Boom R. et al., "Rapid and Simple Method for Purification of Nucleic Acids", Journal of Clinical Microbiology 28(3):495-503 (Mar. 1990).
Cacace M G et al., "The Hofmeister Series: Salt and Solvent Effects on Interfacial Phenomena", Quarterly Reviews of Biophysics 30(3):241-277 (Aug. 1997).
Campanella J.J. et al., "MatGAT: An Application that Generates Similarity/Identity Matrices Using Protein or DNA Sequences", BMC Bioinformatics 4:29 (2003).
Corman V.M. et al., "Detection of 2019 Novel Coronavirus (2019-nCoV) by Real-Time RT-PCR", Euro Surveill vol. 25(3) (2020).
Hourfar M.K. et al., "High-Throughput Purification of Viral RNA Based on Novel Aqueous Chemistry for Nucleic Acid Isolation", Clinical Chemistry 51(7):1217-1222 (Jul. 2005).
Kruskal J.B., "Time Warps, String Edits and Macromolecules: The Theory and Practice of Sequence Comparison", Advanced Book Program (1983).
Larkin M.A. et al., "Clustal W and Clustal X Version 2.0", Bioinformatics 23(21):2947-2948 (2007).
Lee H.H. et al., "Simple Amplification-Based Assay: A Nucleic Acid-Based Point-of-Care Platform for HIV-1 Testing", Journal of Infectious Diseases 201(S1):S65-S71 (2010).
Meinkoth J. et al., "Hybridization of Nucleic Acids Immobilized on Solid Supports", Analytical Biochemistry 138:267-284 (1984).
Needleman S.B. et al., "A General Method Applicable to the Search for Similarities in the Amino Acid Sequence of Two Proteins", J. Mol. Biol. 48(3):443-453 (Mar. 1970).

* cited by examiner

Figure 2A

```
CLUSTAL O(1.2.4) multiple sequence alignment

hCoV_229E_AF304460                              -------ACATGCCAATT------------------------------GCAGACCCTACA     23
SARS_CoV_GZ02_                                  -------AAGAAGAAGAGGAAGACTGGCTGGATGATACTACTGAGCAATCAGAGATTGAG     53
SARS_CoV_ZS-B_                                  -------AAGAAGAAGAGGAAGACTGGCTGGATGATACTACTGAGCAATCAGAGATTGAG     53
Bat_SARS-like_CoV_Rs4231_                       ----------AAGAAGAAGAGGACTGGCTTGGTGATGCTACTGAATTATCGGAGCATGAA     50
hCoV-HKU1_MH940245.1                            ACTGGTGACAATGACGATGAAGATGTTGTTACTGGTGACAATGACGATGAAGATGTTGTT     60
MERS_CoV_KJ477103.2                             -------------------AGGAGTGTTCTGAA---------GTAGAGGCTTCAGATTTA     32
hCoV_OC43_KU131570                              ----------------------------ATGATGGTCCAAGTGTGGAGACATCTGATTCA     32
hCoV-NL63_AY567487                              -------------------ACACTTGTTTT------------------GGTGTTAGTAAA     23
2019-nCoV_MN988713_Atlanta_USA                  -------AAGAGCAAGAAGAAGATTGGTTAGATGATGATAGTCAACAAACTGTTGGTCAA     53
2019-nCoV_MN988669.1_WuhanUniversity_China      -------AAGAGCAAGAAGAAGATTGGTTAGATGATGATAGTCAACAAACTGTTGGTCAA     53
2019-nCoV_MN908947.3_PublicHealth_China         -------AAGAGCAAGAAGAAGATTGGTTAGATGATGATAGTCAACAAACTGTTGGTCAA     53

2019-nCoV-ARP1.1F                               -------------------------------------------------CTGTTGGTCAA     11
2019-nCoV-ARP1.2F                               ----------------------------------------GTCAACAAACTGTTGGTCAA     20
2019-nCoV-ARP1.3F                               ----------------------------------------GTCAACAAACTGTTGGTCAA     20
2019-nCoV-AR-CP1.1                              ------------------------------------------------------------     0
2019-nCoV-AR-CP1.2                              ------------------------------------------------------------     0
2019-nCoV-AR-DP1.2                              ------------------------------------------------------------     0
2019-nCoV-AR-DP1.1                              ------------------------------------------------------------     0
2019-nCoV-ARP1.1R                               ------------------------------------------------------------     0
2019-nCoV-ARP1.2R                               ------------------------------------------------------------     0
```

Figure 2B

```
hCoV_229E_AF304460                               CATTTTGACATTGAA------------------------------------GAAGTTGAA   47
SARS_CoV_GZ02_                                   C-----------------------------------------------------------   54
SARS_CoV_ZS-B_                                   C-----------------------------------------------------------   54
Bat_SARS-like_CoV_Rs4231_                        C-----------------------------------------------------------   51
hCoV-HKU1_MH940245.1                             ACTGGTGACAATGACGATGAAGATGTTGTTACTGGTGACAATGACGATGAAGAGATTGTT   120
MERS_CoV_KJ477103.2                              GAAGAA--------GGTGAATCAG------------------------------AGTGCA   54
hCoV_OC43_KU131570                               CAAGTTGAAGAAGAT------------------G------------TAGAAATGTCGGAT   62
hCoV-NL63_AY567487                               CCTAATGCCATTGATGTTGAACATTTAGAGCT---------------TAAAGAAACTGTT   68
2019-nCoV_MN988713_Atlanta_USA                   CAAGACGGCAGTGAGGACAATCAGACAACTACTA------------TTCAAACAATTGTT   101
2019-nCoV_MN988669.1_WuhanUniversity_China       CAAGACGGCAGTGAGGACAATCAGACAACTACTA------------TTCAAACAATTGTT   101
2019-nCoV_MN908947.3_PublicHealth_China          CAAGACGGCAGTGAGGACAATCAGACAACTACTA------------TTCAAACAATTGTT   101

2019-nCoV-ARP1.1F                                CAAGACGGCA--------------------------------------------------   21
2019-nCoV-ARP1.2F                                ------------------------------------------------------------   20
2019-nCoV-ARP1.3F                                CA----------------------------------------------------------   22
2019-nCoV-AR-CP1.1                               ------GGCAGTGAGGACAATCAGCAACTAC-----------------------------   25
2019-nCoV-AR-CP1.2                               ------------GAGGACAATCAGACAACTACTA------------TTC-----------   25
2019-nCoV-AR-DP1.2                               ------------------------------------------------------------   0
2019-nCoV-AR-DP1.1                               ------------------------------------------------CAAACAATTGTT   12
2019-nCoV-ARP1.1R                                ------------------------------------------------------------   0
2019-nCoV-ARP1.2R                                ------------------------------------------------------------   0
```

Figure 2C

```
hCoV_229E_AF304460                        CTTTTAGATGCAGAG------TTTGTAGAACCAGGCTGTGGTGGTATTTTGGCAGT-AAT  100
SARS_CoV_GZ02_                            ----------------CAGAACCAGAACCTACACCTGAAGA---------ACCAGTTAAT  89
SARS_CoV_ZS-B_                            ----------------CAGAACCAGAACCTACACCTGAAGA---------ACCAGTTAAT  89
Bat_SARS-like_CoV_Rs4231_                 ----------------CAGAACCAGAACTAACACCTGAAGA---------ACCAGTTAAC  86
hCoV-HKU1_MH940245.1                      ACTGGTGACAATGATGACCAAATTGTTGTTACTGGTGATGATG---TAGATGATATTGAA  177
MERS_CoV_KJ477103.2                       TTTCTGAGACTTCAACT-------------GAACAAGTTGACG---TTTCTCATGAGACT  98
hCoV_OC43_KU131570                        TTTGTTGATCTTGAA------------------TCTGTGATTCAGGATTATGAAAATGTT  104
hCoV-NL63_AY567487                        TTTGTTGAACCTAAG------------------GATGGTGGTCAATTTTTTGTTTCTGGT  110
2019-nCoV_MN988713_Atlanta_USA            GAGGTTCAACCTCAATTAGAGATGGAACTTACACCAGTTGTTCAGACTATTGAAGTGAAT  161
2019-nCoV_MN988669.1_WuhanUniversity_China GAGGTTCAACCTCAATTAGAGATGGAACTTACACCAGTTGTTCAGACTATTGAAGTGAAT  161
2019-nCoV_MN908947.3_PublicHealth_China   GAGGTTCAACCTCAATTAGAGATGGAACTTACACCAGTTGTTCAGACTATTGAAGTGAAT  161

2019-nCoV-ARP1.1F                         ------------------------------------------------------------  21
2019-nCoV-ARP1.2F                         ------------------------------------------------------------  20
2019-nCoV-ARP1.3F                         ------------------------------------------------------------  22
2019-nCoV-AR-CP1.1                        ------------------------------------------------------------  25
2019-nCoV-AR-CP1.2                        ------------------------------------------------------------  25
2019-nCoV-AR-DP1.2                        GAGGTTCAACCTCAATTAGAGATGG-----------------------------------  25
2019-nCoV-AR-DP1.1                        GAGGTTCAACCTC-----------------------------------------------  25
2019-nCoV-ARP1.1R                         ------------------------------ACACCAGTTGTTCAGACTATTG--------  22
2019-nCoV-ARP1.2R                         -----------------AGAGATGGAACTTACACCAG-----------------------  20
```

Figure 2D

```
hCoV_229E_AF304460                                AGATGAGCACGTCTTTTATAAGAAGG  126
SARS_CoV_GZ02_                                    CAGTTTACTGGTTATTTAAAACTTAC  115
SARS_CoV_ZS-B_                                    CAGTTTACTGGTTATTTAAAACTTAC  115
Bat_SARS-like_CoV_Rs4231_                         CAGTTTACTGGTTATTTAAAACTTAC  112
hCoV-HKU1_MH940245.1                              AGTGTCTATGATTTTG----------  193
MERS_CoV_KJ477103.2                               TCT-----------------------  101
hCoV_OC43_KU131570                                TGTTTTGA------------------  112
hCoV-NL63_AY567487                                GATTATCTTTGGTATGT---------  127
2019-nCoV_MN988713_Atlanta_USA                    AGTTTTAGTGGTTATTTAAAACTTAC  187
2019-nCoV_MN988669.1_WuhanUniversity_China        AGTTTTAGTGGTTATTTAAAACTTAC  187
2019-nCoV_MN908947.3_PublicHealth_China           AGTTTTAGTGGTTATTTAAAACTTAC  187

2019-nCoV-ARP1.1F                                 --------------------------  21
2019-nCoV-ARP1.2F                                 --------------------------  20
2019-nCoV-ARP1.3F                                 --------------------------  22
2019-nCoV-AR-CP1.1                                --------------------------  25
2019-nCoV-AR-CP1.2                                --------------------------  25
2019-nCoV-AR-DP1.2                                --------------------------  25
2019-nCoV-AR-DP1.1                                --------------------------  25
2019-nCoV-ARP1.1R                                 --------------------------  22
2019-nCoV-ARP1.2R                                 --------------------------  20
```

Figure 3A

```
hCoV_OC43_KU131570                              AGAACCGGCAGTTTTTGGAGTTTCAACCCAGAAACAAACAACTTGATGTGTATAGATATG   60
hCoV-HKU1_MH940245.1                            AGAACTGGCAGTTGGTGGAGTTTTAACCCAGAGACTAATAATCTTATGTGTATTGATATG   60
hCoV-NL63_AY567487                              CGTGTTAAAACTTTTTGGGCTTTTAATCCTGAAACTAATGCAATCATCTCTCTCCAGGTT   60
hCoV_229E_AF304460                              CGTGCTCGAACTTTTTGGGCATGGAATCCTGAGGTTAATGCAATCACT----GTCACAAC   56
MERS_CoV_KJ477103.2                             AGAACTGGATCATGGTGGTCATTCAATCCTGAGACTAATTGCCTTTTGAACGTTCCATTT   60
Bat_SARS-like_CoV_Rs4231_                       ------------GTGTATTGCATGCATAAAGAATGCAGTA------------TACAAGAA   36
SARS_CoV_ZS-B_                                  ------------------------------------------------------------   0
SARS_CoV_GZ02_                                  -----------------GCAGTTGCATACGCACTGTAGTA--------------CAGCGC   29
2019-nCoV_MN988713_Atlanta_USA                  ---------------GCTGCATTTCACCAAGAATGTAGTT------------TACAGTCA   33
2019-nCoV_MN988669.1_WuhanUniversity_China      ---------------GCTGCATTTCACCAAGAATGTAGTT------------TACAGTCA   33
2019-nCoV_MN908947.3_PublicHealth_China         ---------------GCTGCATTTCACCAAGAATGTAGTT------------TACAGTCA   33

SA-nCoV-F2.3                                    ------------------------------------------------------------   0
SA-nCoV-R2.3                                    ------------------------------------------------------------   0
SA-nCoV-R2.5                                    ------------------------------------------------------------   0
SA-nCoV-R2.4                                    ------------------------------------------------------------   0
SA-nCoV-DP2.4                                   ------------------------------------------------------------   0
SA-nCoV-DP2.3                                   ------------------------------------------------------------   0
SA-nCoV-CP2.3                                   ------------------------------------------------------------   0
```

Figure 3B

```
hCoV_OC43_KU131570                          AAAGGAACAATGTTT-GTTAGGCCAATAATTGAGGACTACCATACC----CTGACGGTCA  115
hCoV-HKU1_MH940245.1                        AAAGGTAAGATGTAT-GTTAGGCCAGTTATTGAGGACTATCATACA----TTAACGGCTA  115
hCoV-NL63_AY567487                          TACGGACATAATTAT----TACTTACCGGTGATGGCTGCACCTACAGGT-GTTACATTAA  115
hCoV_229E_AF304460                          CGTGTTGGGACAGACATACTATCAACCCATTCAACAAGCTCCAACAGG-------CATTA  109
MERS_CoV_KJ477103.2                         GGTGGTACAACTGTC-GTACGTCCACTCGTAGAGGACTCT----------ACCAGTGTAA  109
Bat_SARS-like_CoV_Rs4231_                   TGTTGTGAAAATCAA-CCATTCCAACCTGAAGACCCATGTCCAATACATTATTATTCGGA  95
SARS_CoV_ZS-B_                              ----------------------------------------------------GCAGTTGC  8
SARS_CoV_GZ02_                              TGTGCATCTAATAAA-CCTCATGTGCTTGAAGATCCTTGTCCTACTGGTTACCAACCTGA  88
2019-nCoV_MN988713_Atlanta_USA              TGTACTCAACATCAA-CCATATGTAGTTGATGACCCGTGTCCTATTCACTTCTATTCTAA  92
2019-nCoV_MN988669.1_WuhanUniversity_China  TGTACTCAACATCAA-CCATATGTAGTTGATGACCCGTGTCCTATTCACTTCTATTCTAA  92
2019-nCoV_MN908947.3_PublicHealth_China     TGTACTCAACATCAA-CCATATGTAGTTGATGACCCGTGTCCTATTCACTTCTATTCTAA  92

SA-nCoV-F2.3                                -----------------------TAGTTGATGACCCGTGTCCT-----------------  20
SA-nCoV-R2.3                                ------------------------------------------------------------  0
SA-nCoV-R2.5                                ------------------------------------------------------------  0
SA-nCoV-R2.4                                ------------------------------------------------------------  0
SA-nCoV-DP2.4                               ------------------------------------------------------------  0
SA-nCoV-DP2.3                               ------------------------------------------------------------  0
SA-nCoV-CP2.3                               ------------------------------------------------------------  0
```

Figure 3C

```
hCoV_OC43_KU131570                          CAATAATACGCGG-------TCATCTTTACATTCAAGGTATAAAACTAGGTAC---TGGC  165
hCoV-HKU1_MH940245.1                        CTGTTATCCGTGG-------TCATCTTTATATACAGGGTGTTAAACTTGGCAC---TGGT  165
hCoV-NL63_AY567487                          CACTTCTTAGTGG-------TGTACTTCTTGTTGATGGCCATAAGATTGCTACTCGTGTT  168
hCoV_229E_AF304460                          CTGTG-ACCTTGCTGAGCGGCGTGCTTTACGTTGACGGACATAGATTGGCTTCAGGTGTT  168
MERS_CoV_KJ477103.2                         CTGCTGTTGTAAC-------CAATGGCCACCTCAAAATGGCTGGCATGCATTTCGGTGCT  162
Bat_SARS-like_CoV_Rs4231_                   CTGGTTTGTAAAAATTGGA---CCTCGCAAGTCTGCTCGCCTAGTACAACTTTGTGCTGG  152
SARS_CoV_ZS-B_                              ATAC--GCACTGTAGTACAGCGCTGTGCATCTAATATAGCACTGCTTGGCTTTGTGCTCT  66
SARS_CoV_GZ02_                              ATGGAATATAAGGTACAACACTAGGGGTAATACTTATAGCACTGCTTGGCTTTGTGCTCT  148
2019-nCoV_MN988713_Atlanta_USA              ATGGTATATTAGAGTAGGAGCTAGAAAATCAGCACCTTTAATTGAAT---TGTGCSTGGA  149
2019-nCoV_MN988669.1_WuhanUniversity_China  ATGGTATATTAGAGTAGGAGCTAGAAAATCAGCACCTTTAATTGAAT---TGTGCSTGGA  149
2019-nCoV_MN908947.3_PublicHealth_China     ATGGTATATTAGAGTAGGAGCTAGAAAATCAGCACCTTTAATTGAAT---TGTGCSTGGA  149

SA-nCoV-F2.3                                ------------------------------------------------------------  20
SA-nCoV-R2.3                                ------------------------------------------------------------  0
SA-nCoV-R2.5                                ------------------------------------------------------------  0
SA-nCoV-R2.4                                ------------------------------------------------------------  0
SA-nCoV-DP2.4                               ------------------------------------------------------------  0
SA-nCoV-DP2.3                               ------------------------------------------------------------  0
SA-nCoV-CP2.3                               ------------------------------------------------------------  0
```

Figure 3D

```
hCoV_OC43_KU131570                          TATTCTTTGGCAGATTTGCCAGCTTATATGACTGTTGCTAAGGTCACATACCTGTGCACA   225
hCoV-HKU1_MH940245.1                        TACACGCTTGCCGATTTGCCTGTTTATGTTACTGTAGCTAAGGTGCAAGTCCTCTGTACT   225
hCoV-NL63_AY567487                          CA---AGTGGGTCAGTTGCCTAAATATGTAATAGTTGCTACGCCTAGTACCACAATTGTT   225
hCoV_229E_AF304460                          CAGGTT---CATAACCTACCTGAATACATGACAGTTGCCGTGCCGAGCACTACTATAATT   225
MERS_CoV_KJ477103.2                         TGTGACTACGACAGACTTCCTAATGAAGTCACCGTGGCCAAACCCAATGTGCTGATTGCT   222
Bat_SARS-like_CoV_Rs4231_                   TGAATATGGACACA--------------------------------GAGTTCCAATACAT   180
SARS_CoV_ZS-B_                              AGGAAA--------------------------------------------GGTTTTACCT   82
SARS_CoV_GZ02_                              AGGAAA--------------------------------------------GGTTTTACCT   164
2019-nCoV_MN988713_Atlanta_USA              TGAGGCTGGTTCTA--------------------------------AATCACCCATTCAG   177
2019-nCoV_MN988669.1_WuhanUniversity_China  TGAGGCTGGTTCTA--------------------------------AATCACCCATTCAG   177
2019-nCoV_MN908947.3_PublicHealth_China     TGAGGCTGGTTCTA--------------------------------AATCACCCATTCAG   177

SA-nCoV-F2.3                                ------------------------------------------------------------   20
SA-nCoV-R2.3                                ------------------------------------------------------------   0
SA-nCoV-R2.5                                ------------------------------------------------------------   0
SA-nCoV-R2.4                                ------------------------------------------------------------   0
SA-nCoV-DP2.4                               ------------------------------------------------------------   0
SA-nCoV-DP2.3                               ------------------------------------------------------------   0
SA-nCoV-CP2.3                               -----CTGGTTCTA--------------------------------AATCACCCATTCA-   22
```

Figure 3E

```
hCoV_OC43_KU131570                           TATAAGCGTGGTTTTC---TTGACAAGATAAGCGATACTAGTGGTTTTGCTGTTTATGTT   282
hCoV-HKU1_MH940245.1                         TATAAACGTGCCTTTT---TAGATAAGTTAGATGTTAATAGTGGTTTTGCTGTTTTTGTT   282
hCoV-NL63_AY567487                           TGTGACCGTGTTGGTCGCTCTGTTAATGAAACAAGCCAGACTGGTTGGGCATTCTACGTC   285
hCoV_229E_AF304460                           TATAGTAGAGTCGGAAGGTCCGTAAATTCACAAAATAGCACAGGCTGGGTTTTCTACGTA   285
MERS_CoV_KJ477103.2                          TTAAAAATGGTGAAGCGGCAAAGC--TACGGA-ACTAATTCCGGCGTTGCCATTTACCAT   279
Bat_SARS-like_CoV_Rs4231_                    TATGAAATGT-TTGGCAATTATAC--TATTTCATGT---GAACCACTTGAAATAAATTGT   234
SARS_CoV_ZS-B_                               TTTCATAGAT-GGCACACTATGGT--TCAAACATGCACACCTAATGTTACTATCAACTGT   139
SARS_CoV_GZ02_                               TTTCATAGAT-GGCACACTATGGT--TCAAACATGCACACCTAATGTTACTATCAACTGT   221
2019-nCoV_MN988713_Atlanta_USA               TACA---TCG-ATATCGGTAATTA--TACAGTTTCCTGTTYACCTTTTACAATTAATTGC   231
2019-nCoV_MN988669.1_WuhanUniversity_China   TACA---TCG-ATATCGGTAATTA--TACAGTTTCCTGTTYACCTTTTACAATTAATTGC   231
2019-nCoV_MN908947.3_PublicHealth_China      TACA---TCG-ATATCGGTAATTA--TACAGTTTCCTGTTYACCTTTTACAATTAATTGC   231

SA-nCoV-F2.3                                 ------------------------------------------------------------   20
SA-nCoV-R2.3                                 ------------------------------------------------------------   0
SA-nCoV-R2.5                                 ------------------------------------------------------------   0
SA-nCoV-R2.4                                 ------------------------------------------------------------   0
SA-nCoV-DP2.4                                ------------------------------------------------------------   0
SA-nCoV-DP2.3                                ------------------------------------------------------------   0
SA-nCoV-CP2.3                                ------------------------------------------------------------   22
```

Figure 3F

| | | |
|---|---|---|
| hCoV_OC43_KU131570 | AAGTCCAAAGTCGGTAATTACCGACTGCCATCAACCCAAAAGGGTTC------AGGCATG | 336 |
| hCoV-HKU1_MH940245.1 | AAGTCTAAAGTTGGTAACTATCGTTTACCTTCTAGTAAA---TCTAG------TGGTATG | 333 |
| hCoV-NL63_AY567487 | CGTGCTAAACATGGTGATTTTTCTGGTGTTGCCTCTCAGGAGGGTGT------TTTGTCA | 339 |
| hCoV_229E_AF304460 | CGAGTAAAACACGGTGATTTTTCTGCAGTGAGCT----CTCCCATGAGCAACATGACAGA | 341 |
| MERS_CoV_KJ477103.2 | AGATATAAGGCAGGTAATTACAGGAGTCCGCCTATTACGGCGGATATTGAACTTGCATTG | 339 |
| Bat_SARS-like_CoV_Rs4231_ | CAAAACCCACCAGTTGGAAGTCTCATTGTACGTTGTTCATATGATGTTGACTTTATGGAG | 294 |
| SARS_CoV_ZS-B_ | CAAGATCCAGCTGGTGGTGCGCTTATAGCTAGGTGTTGGTACCTTCATGAAGGTCACCAA | 199 |
| SARS_CoV_GZ02_ | CAAGATCCAGCTGGTGGTGCGCTTATAGCTAGGTGTTGGTACCTTCATGAAGGTCACCAA | 281 |
| 2019-nCoV_MN988713_Atlanta_USA | CAGGAACCTAAATTGGGTAGTCTTGTAGTGCGTTGTTCGTTCTATGAAGACTTTTTAGAG | 291 |
| 2019-nCoV_MN988669.1_WuhanUniversity_China | CAGGAACCTAAATTGGGTAGTCTTGTAGTGCGTTGTTCGTTCTATGAAGACTTTTTAGAG | 291 |
| 2019-nCoV_MN908947.3_PublicHealth_China | CAGGAACCTAAATTGGGTAGTCTTGTAGTGCGTTGTTCGTTCTATGAAGACTTTTTAGAG | 291 |
| | | |
| SA-nCoV-F2.3 | ------------------------------------------------------------ | 20 |
| SA-nCoV-R2.3 | ------------------------------------------------------------ | 0 |
| SA-nCoV-R2.5 | ---------------------------GTGCGTTGTTCGTTCTATG-------------- | 19 |
| SA-nCoV-R2.4 | -----------------------------------------------------------G | 1 |
| SA-nCoV-DP2.4 | ---GGAACCTAAATTGGGTAGTCTTG---------------------------------- | 23 |
| SA-nCoV-DP2.3 | ----GAACCTAAATTGGGTAGTCTTGTAG------------------------------- | 25 |
| SA-nCoV-CP2.3 | ------------------------------------------------------------ | 22 |

Figure 3G

```
hCoV_OC43_KU131570                          GACA---CCGCATTGTTGAGAAATAATATCTAAATTTTAA----------------GGAT  377
hCoV-HKU1_MH940245.1                        GATA---CTGCCTTGTTGAGAGCTTAAATCTAAACTATTA----------------GGAT  374
hCoV-NL63_AY567487                          GAAA---GAGAGAAGTTGCTTCATTTAATCTAAACTAAACAAAATGGCTA---GTGTAAA  393
hCoV_229E_AF304460                          AAAC---GAAAGATTGCT--TCATTTTTTCTAAACTGAACGAAAAGATGGCTACAGTCAA  396
MERS_CoV_KJ477103.2                         CTT----CGAGCTTAGGC----------TCTTTAGTAAG----AGTATCT------TAAT  375
Bat_SARS-like_CoV_Rs4231_                   TATCA--CGACGTTCGTGTTGTTCTAGATTTCATCTAAACGAACAAACTA------AAAT  346
SARS_CoV_ZS-B_                              ACTGCTGCATTTAGAGACGTACTTGTTGTTTTAAATAAACGAACAAATTA------AAAT  253
SARS_CoV_GZ02_                              ACTGCTGCATTTAGAGACGTATTTGTTGTTTTAAATAAACGAACAAATTA------AAAT  335
2019-nCoV_MN988713_Atlanta_USA              TATCA--TGACGTTCGTGTTGTTTTAGATTTCATCTAAACGAACAAACTA------AAAT  343
2019-nCoV_MN988669.1_WuhanUniversity_China  TATCA--TGACGTTCGTGTTGTTTTAGATTTCATCTAAACGAACAAACTA------AAAT  343
2019-nCoV_MN908947.3_PublicHealth_China     TATCA--TGACGTTCGTGTTGTTTTAGATTTCATCTAAACGAACAAACTA------AAAT  343

SA-nCoV-F2.3                                ------------------------------------------------------------  20
SA-nCoV-R2.3                                ----------------------------------------------------------AT  2
SA-nCoV-R2.5                                ------------------------------------------------------------  19
SA-nCoV-R2.4                                TATCA--TGACGTTCGTGTTG---------------------------------------  20
SA-nCoV-DP2.4                               ------------------------------------------------------------  23
SA-nCoV-DP2.3                               ------------------------------------------------------------  25
SA-nCoV-CP2.3                               ------------------------------------------------------------  22
```

Figure 3H

| | | |
|---|---|---|
| hCoV_OC43_KU131570 | GTCTTTTACTCCTGGTAAGCAATCCAGTAGTAGAGCGTCCTCTGGAAATCGTTCTGGTAA | 437 |
| hCoV-HKU1_MH940245.1 | GTCTTATACTCCCGGTCATCATGCTGGAAGTAGAAGCTCCTCTGGAAATCGTTCAGGAAT | 434 |
| hCoV-NL63_AY567487 | TTGGGCCGATGA--CAGAGCTGCTAGGAAGAAATTTC--CTC----------------CT | 433 |
| hCoV_229E_AF304460 | ATGGGCTGATGCATCTGAACCACAACGTGGTCGTCAG--GGTA---------------GA | 439 |
| MERS_CoV_KJ477103.2 | TGATTTTAACGAATCTCAATTTCATTGTTATGGCATC--CCCTGCTGCAC--CTCGTGCT | 431 |
| Bat_SARS-like_CoV_Rs4231_ | GTCTGATAATGGACCCCAACCAAATCAGCGTAGTGCC--CCCCGCATTACATTTGGTGGA | 404 |
| SARS_CoV_ZS-B_ | GTCTGATAATGGACCCCAATCAAACCAACGTAGTGCC--CCCCGCATTACATTTGGTGGA | 311 |
| SARS_CoV_GZ02_ | GTCTGATAATGGACCCCAATCAAACCAACGTAGTGCC--CCCCGCATTACATTTGGTGGA | 393 |
| 2019-nCoV_MN988713_Atlanta_USA | GTCTGATAATGGACCCCAAAAT---CAGCGAAATGCA--CCCCGCATTACGTTTGGTGGA | 398 |
| 2019-nCoV_MN988669.1_WuhanUniversity_China | GTCTGATAATGGACCCCAAAAT---CAGCGAAATGCA--CCCCGCATTACGTTTGGTGGA | 398 |
| 2019-nCoV_MN908947.3_PublicHealth_China | GTCTGATAATGGACCCCAAAAT---CAGCGAAATGCA--CCCCGCATTACGTTTGGTGGA | 398 |
| | | |
| SA-nCoV-F2.3 | ------------------------------------------------------------ | 20 |
| SA-nCoV-R2.3 | GTCTGATAATGGACCCCA------------------------------------------ | 20 |
| SA-nCoV-R2.5 | ------------------------------------------------------------ | 19 |
| SA-nCoV-R2.4 | ------------------------------------------------------------ | 20 |
| SA-nCoV-DP2.4 | ------------------------------------------------------------ | 23 |
| SA-nCoV-DP2.3 | ------------------------------------------------------------ | 25 |
| SA-nCoV-CP2.3 | ------------------------------------------------------------ | 22 |

Figure 3I

| | | |
|---|---|---|
| hCoV_OC43_KU131570 | TGGCATCCTTAAGTG | 452 |
| hCoV-HKU1_MH940245.1 | CCTCAAGAA------ | 443 |
| hCoV-NL63_AY567487 | CCTTC---------- | 438 |
| hCoV_229E_AF304460 | ATACCTTATTC---- | 450 |
| MERS_CoV_KJ477103.2 | GTTTC---------- | 436 |
| Bat_SARS-like_CoV_Rs4231_ | CCCACAGATTC---- | 415 |
| SARS_CoV_ZS-B_ | CCCACAGATTC---- | 322 |
| SARS_CoV_GZ02_ | CCCACAGATTC---- | 404 |
| 2019-nCoV_MN988713_Atlanta_USA | CCCTCAGATTC---- | 409 |
| 2019-nCoV_MN988669.1_WuhanUniversity_China | CCCTCAGATTC---- | 409 |
| 2019-nCoV_MN908947.3_PublicHealth_China | CCCTCAGATTC---- | 409 |
| | | |
| SA-nCoV-F2.3 | --------------- | 20 |
| SA-nCoV-R2.3 | --------------- | 20 |
| SA-nCoV-R2.5 | --------------- | 19 |
| SA-nCoV-R2.4 | --------------- | 20 |
| SA-nCoV-DP2.4 | --------------- | 23 |
| SA-nCoV-DP2.3 | --------------- | 25 |
| SA-nCoV-CP2.3 | --------------- | 22 |

```
SEQUENCE LISTING

<160> NUMBER OF SEQ ID NOS: 48

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1

ctgttggtca acaagacggc a                                              21
```

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gtcaacaaac tgttggtcaa 20

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gtcaacaaac tgttggtcaa ca 22

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
cattacaggt ggtgttgttc agtt 24

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
caatagtctg aacaactggt gt 22

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctggtgtaag ttccatctct 20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
aggtgacaat ttgtccaccg ac 22

<210> SEQ ID NO 8
<211> LENGTH: 25
<212> TYPE: DNA
<213> ORGANISM: Artificial Sequence
<220> FEATURE:
<223> OTHER INFORMATION: Probe

<400> SEQUENCE: 8
ggcagtgagg acaatcagca actac 25

<210> SEQ ID NO 9
<211> LENGTH: 25
<212> TYPE: DNA
<213> ORGANISM: Artificial Sequence
<220> FEATURE:
<223> OTHER INFORMATION: Probe

<400> SEQUENCE: 9
gaggacaatc agacaactac tattc 25

<210> SEQ ID NO 10
<211> LENGTH: 20
<212> TYPE: DNA
<213> ORGANISM: Artificial Sequence
<220> FEATURE:
<223> OTHER INFORMATION: Probe

<400> SEQUENCE: 10
acccgtcctt gattggcttg 20

<210> SEQ ID NO 11
<211> LENGTH: 25
<212> TYPE: DNA
<213> ORGANISM: Artificial Sequence
<220> FEATURE:
<223> OTHER INFORMATION: Probe

<400> SEQUENCE: 11
caaacaattg ttgaggttca acctc 25

<210> SEQ ID NO 12
<211> LENGTH: 25
<212> TYPE: DNA
<213> ORGANISM: Artificial Sequence
<220> FEATURE:
<223> OTHER INFORMATION: Probe

<400> SEQUENCE: 12
gaggttcaac ctcaattaga gatgg 25

<210> SEQ ID NO 13
<211> LENGTH: 25
<212> TYPE: DNA
<213> ORGANISM: Artificial Sequence
<220> FEATURE:
<223> OTHER INFORMATION: Probe

<400> SEQUENCE: 13
ggaaggtgta gagtttctta gagac 25

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tagttgatga cccgtgtcct 20

<210> SEQ ID NO 15

<211> LENGTH: 20
<212> TYPE: DNA
<213> ORGANISM: Artificial Sequence
<220> FEATURE:
<223> OTHER INFORMATION: Primer

<400> SEQUENCE: 15
tggggtccat tatcagacat 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caacacgaac gtcatgatac 20

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
catagaacga acaacgcac 19

<210> SEQ ID NO 18
<211> LENGTH: 22
<212> TYPE: DNA
<213> ORGANISM: Artificial Sequence
<220> FEATURE:
<223> OTHER INFORMATION: Probe

<400> SEQUENCE: 18
ctggttctaa atcacccatt ca 22

<210> SEQ ID NO 19
<211> LENGTH: 25
<212> TYPE: DNA
<213> ORGANISM: Artificial Sequence
<220> FEATURE:
<223> OTHER INFORMATION: Probe

<400> SEQUENCE: 19
gaacctaaat tgggtagtct tgtag 25

<210> SEQ ID NO 20
<211> LENGTH: 23
<212> TYPE: DNA
<213> ORGANISM: Artificial Sequence
<220> FEATURE:
<223> OTHER INFORMATION: Probe

<400> SEQUENCE: 20
ggaacctaaa ttgggtagtc ttg 23

<210> SEQ ID NO 21
<211> LENGTH: 31
<212> TYPE: DNA
<213> ORGANISM: Artificial Sequence
<220> FEATURE:
<223> OTHER INFORMATION: T7 promoter sequence

<400> SEQUENCE: 21
aattctaata cgactcacta tagggagaag g 31

<210> SEQ ID NO 22
<211> LENGTH: 31
<212> TYPE: DNA
<213> ORGANISM: Artificial Sequence
<220> FEATURE:
<223> OTHER INFORMATION: T7 promoter sequence

<400> SEQUENCE: 22
aattctaata cgactcacta taggggaaaa g 31

<210> SEQ ID NO 23
<211> LENGTH: 18
<212> TYPE: DNA
<213> ORGANISM: Artificial Sequence
<220> FEATURE:
<223> OTHER INFORMATION: T7 promoter sequence

<400> SEQUENCE: 23
taatacgact cactatag 18

<210> SEQ ID NO 24
<211> LENGTH: 31
<212> TYPE: DNA
<213> ORGANISM: Artificial Sequence
<220> FEATURE:
<223> OTHER INFORMATION: T7 promoter sequence

<400> SEQUENCE: 24
aattctaata cgactcacta tagggaaagg a 31

<210> SEQ ID NO 25
<211> LENGTH: 30
<212> TYPE: DNA
<213> ORGANISM: Artificial Sequence
<220> FEATURE:
<223> OTHER INFORMATION: T7 promoter sequence

<400> SEQUENCE: 25
aattctaata cgactcacta tagggaaagg 30

<210> SEQ ID NO 26
<211> LENGTH: 31
<212> TYPE: DNA
<213> ORGANISM: Artificial Sequence
<220> FEATURE:
<223> OTHER INFORMATION: T7 promoter sequence

<400> SEQUENCE: 26
aattctaata cgactcacta taggggaaag a 31

<210> SEQ ID NO 27
<211> LENGTH: 101
<212> TYPE: DNA
<213> ORGANISM: Human coronavirus

<400> SEQUENCE: 27
aggagtgttc tgaagtagag gcttcagatt tagaagaagg tgaatcagag tgcatttctg 60
agacttcaac tgaacaagtt gacgtttctc atgagacttc t 101

<210> SEQ ID NO 28
<211> LENGTH: 112
<212> TYPE: DNA

<213> ORGANISM: Human coronavirus

<400> SEQUENCE: 28
atgatggtcc aagtgtggag acatctgatt cacaagttga agaagatgta gaaatgtcgg 60
attttgttga tcttgaatct gtgattcagg attatgaaaa tgtttgtttt ga 112

<210> SEQ ID NO 29
<211> LENGTH: 127
<212> TYPE: DNA
<213> ORGANISM: Human coronavirus

<400> SEQUENCE: 29
acacttgttt tggtgttagt aaacctaatg ccattgatgt tgaacattta gagcttaaag 60
aaactgtttt tgttgaacct aaggatggtg gtcaattttt tgtttctggt gattatcttt 120
ggtatgt 127

<210> SEQ ID NO 30
<211> LENGTH: 126
<212> TYPE: DNA
<213> ORGANISM: Human coronavirus

<400> SEQUENCE: 30
acatgccaat tgcagaccct acacattttg acattgaaga agttgaactt ttagatgcag 60
agtttgtaga accaggctgt ggtggtattt tggcagtaat agatgagcac gtcttttata 120
agaagg 126

<210> SEQ ID NO 31
<211> LENGTH: 193
<212> TYPE: DNA
<213> ORGANISM: Human coronavirus

<400> SEQUENCE: 31
actggtgaca atgacgatga agatgttgtt actggtgaca atgacgatga agatgttgtt 60
actggtgaca atgacgatga agatgttgtt actggtgaca atgacgatga agagattgtt 120
actggtgaca atgatgacca aattgttgtt actggtgatg atgtagatga tattgaaagt 180
gtctatgatt ttg 193

<210> SEQ ID NO 32
<211> LENGTH: 115
<212> TYPE: DNA
<213> ORGANISM: Human coronavirus

<400> SEQUENCE: 32
aagaagaaga ggaagactgg ctggatgata ctactgagca atcagagatt gagccagaac 60
cagaacctac acctgaagaa ccagttaatc agtttactgg ttatttaaaa cttac 115

<210> SEQ ID NO 33
<211> LENGTH: 115
<212> TYPE: DNA
<213> ORGANISM: Human coronavirus

<400> SEQUENCE: 33
aagaagaaga ggaagactgg ctggatgata ctactgagca atcagagatt gagccagaac 60
cagaacctac acctgaagaa ccagttaatc agtttactgg ttatttaaaa cttac 115

<210> SEQ ID NO 34
<211> LENGTH: 112

<212> TYPE: DNA
<213> ORGANISM: Bat SARS-like coronavirus

<400> SEQUENCE: 34
aagaagaaga ggactggctt ggtgatgcta ctgaattatc ggagcatgaa ccagaaccag 60
aactaacacc tgaagaacca gttaaccagt ttactggtta tttaaaactt ac 112

<210> SEQ ID NO 35
<211> LENGTH: 187
<212> TYPE: DNA
<213> ORGANISM: Human coronavirus

<400> SEQUENCE: 35
aagagcaaga agaagattgg ttagatgatg atagtcaaca aactgttggt caacaagacg 60
gcagtgagga caatcagaca actactattc aaacaattgt tgaggttcaa cctcaattag 120
agatggaact tacaccagtt gttcagacta ttgaagtgaa tagttttagt ggttatttaa 180
aacttac 187

<210> SEQ ID NO 36
<211> LENGTH: 187
<212> TYPE: DNA
<213> ORGANISM: Human coronavirus

<400> SEQUENCE: 36
aagagcaaga agaagattgg ttagatgatg atagtcaaca aactgttggt caacaagacg 60
gcagtgagga caatcagaca actactattc aaacaattgt tgaggttcaa cctcaattag 120
agatggaact tacaccagtt gttcagacta ttgaagtgaa tagttttagt ggttatttaa 180
aacttac 187

<210> SEQ ID NO 37
<211> LENGTH: 187
<212> TYPE: DNA
<213> ORGANISM: Human coronavirus

<400> SEQUENCE: 37
aagagcaaga agaagattgg ttagatgatg atagtcaaca aactgttggt caacaagacg 60
gcagtgagga caatcagaca actactattc aaacaattgt tgaggttcaa cctcaattag 120
agatggaact tacaccagtt gttcagacta ttgaagtgaa tagttttagt ggttatttaa 180
aacttac 187

<210> SEQ ID NO 38
<211> LENGTH: 436
<212> TYPE: DNA
<213> ORGANISM: Human coronavirus

<400> SEQUENCE: 38
agaactggat catggtggtc attcaatcct gagactaatt gccttttgaa cgttccattt 60
ggtggtacaa ctgtcgtacg tccactcgta gaggactcta ccagtgtaac tgctgttgta 120
accaatggcc acctcaaaat ggctggcatg catttcggtg cttgtgacta cgacagactt 180
cctaatgaag tcaccgtggc caaacccaat gtgctgattg ctttaaaaat ggtgaagcgg 240
caaagctacg gaactaattc cggcgttgcc atttaccata gatataaggc aggtaattac 300
aggagtccgc ctattacggc ggatattgaa cttgcattgc ttcgagctta ggctctttag 360
taagagtatc ttaattgatt ttaacgaatc tcaatttcat tgttatggca tcccctgctg 420
cacctcgtgc tgtttc 436

<210> SEQ ID NO 39
<211> LENGTH: 452
<212> TYPE: DNA
<213> ORGANISM: Human coronavirus

<400> SEQUENCE: 39
agaaccggca gtttttggag tttcaaccca gaaacaaaca acttgatgtg tatagatatg 60
aaaggaacaa tgtttgttag gccaataatt gaggactacc ataccctgac ggtcacaata 120
atacgcggtc atctttacat tcaaggtata aaactaggta ctggctattc tttggcagat 180
ttgccagctt atatgactgt tgctaaggtc acatacctgt gcacatataa gcgtggtttt 240
cttgacaaga taagcgatac tagtggtttt gctgtttatg ttaagtccaa agtcggtaat 300
taccgactgc catcaaccca aaagggttca ggcatggaca ccgcattgtt gagaaataat 360
atctaaattt taaggatgtc ttttactcct ggtaagcaat ccagtagtag agcgtcctct 420
ggaaatcgtt ctggtaatgg catccttaag tg 452

<210> SEQ ID NO 40
<211> LENGTH: 438
<212> TYPE: DNA
<213> ORGANISM: Human coronavirus

<400> SEQUENCE: 40
cgtgttaaaa ctttttgggc ttttaatcct gaaactaatg caatcatctc tctccaggtt 60
tacggacata attattactt accggtgatg gctgcaccta caggtgttac attaacactt 120
cttagtggtg tacttcttgt tgatggccat aagattgcta ctcgtgttca agtgggtcag 180
ttgcctaaat atgtaatagt tgctacgcct agtaccacaa ttgtttgtga ccgtgttggt 240
cgctctgtta atgaaacaag ccagactggt tgggcattct acgtccgtgc taaacatggt 300
gatttttctg gtgttgcctc tcaggagggt gttttgtcag aaagagagaa gttgcttcat 360
ttaatctaaa ctaaacaaaa tggctagtgt aaattgggcc gatgacagag ctgctaggaa 420
gaaatttcct cctccttc 438

<210> SEQ ID NO 41
<211> LENGTH: 450
<212> TYPE: DNA
<213> ORGANISM: Human coronavirus

<400> SEQUENCE: 41
cgtgctcgaa ctttttgggc atggaatcct gaggttaatg caatcactgt cacaaccgtg 60
ttgggacaga catactatca acccattcaa caagctccaa caggcattac tgtgaccttg 120
ctgagcggcg tgctttacgt tgacggacat agattggctt caggtgttca ggttcataac 180
ctacctgaat acatgacagt tgccgtgccg agcactacta taatttatag tagagtcgga 240
aggtccgtaa attcacaaaa tagcacaggc tgggttttct acgtacgagt aaaacacggt 300
gatttttctg cagtgagctc tcccatgagc aacatgacag aaaacgaaag attgcttcat 360
tttttctaaa ctgaacgaaa agatggctac agtcaaatgg gctgatgcat ctgaaccaca 420
acgtggtcgt cagggtagaa taccttattc 450

<210> SEQ ID NO 42
<211> LENGTH: 443
<212> TYPE: DNA
<213> ORGANISM: Human coronavirus

<400> SEQUENCE: 42
agaactggca gttggtggag ttttaaccca gagactaata atcttatgtg tattgatatg 60
aaaggtaaga tgtatgttag gccagttatt gaggactatc atacattaac ggctactgtt 120
atccgtggtc atctttatat acagggtgtt aaacttggca ctggttacac gcttgccgat 180
ttgcctgttt atgttactgt agctaaggtg caagtcctct gtacttataa acgtgccttt 240
ttagataagt tagatgttaa tagtggtttt gctgtttttg ttaagtctaa agttggtaac 300
tatcgtttac cttctagtaa atctagtggt atggatactg ccttgttgag agcttaaatc 360
taaactatta ggatgtctta tactcccggt catcatgctg gaagtagaag ctcctctgga 420
aatcgttcag gaatcctcaa gaa 443

<210> SEQ ID NO 43
<211> LENGTH: 404
<212> TYPE: DNA
<213> ORGANISM: Human coronavirus

<400> SEQUENCE: 43
gcagttgcat acgcactgta gtacagcgct gtgcatctaa taaacctcat gtgcttgaag 60
atccttgtcc tactggttac caacctgaat ggaatataag gtacaacact aggggtaata 120
cttatagcac tgcttggctt tgtgctctag gaaaggtttt accttttcat agatggcaca 180
ctatggttca aacatgcaca cctaatgtta ctatcaactg tcaagatcca gctggtggtg 240
cgcttatagc taggtgttgg taccttcatg aaggtcacca aactgctgca tttagagacg 300
tatttgttgt tttaaataaa cgaacaaatt aaaatgtctg ataatggacc ccaatcaaac 360
caacgtagtg ccccccgcat tacatttggt ggacccacag attc 404

<210> SEQ ID NO 44
<211> LENGTH: 322
<212> TYPE: DNA
<213> ORGANISM: Human coronavirus

<400> SEQUENCE: 44
gcagttgcat acgcactgta gtacagcgct gtgcatctaa tatagcactg cttggctttg 60
tgctctagga aaggttttac cttttcatag atggcacact atggttcaaa catgcacacc 120
taatgttact atcaactgtc aagatccagc tggtggtgcg cttatagcta ggtgttggta 180
ccttcatgaa ggtcaccaaa ctgctgcatt tagagacgta cttgttgttt taaataaacg 240
aacaaattaa aatgtctgat aatggacccc aatcaaacca acgtagtgcc ccccgcatta 300
catttggtgg acccacagat tc 322

<210> SEQ ID NO 45
<211> LENGTH: 415
<212> TYPE: DNA
<213> ORGANISM: Bat SARS-like coronavirus

<400> SEQUENCE: 45
gtgtattgca tgcataaaga atgcagtata caagaatgtt gtgaaaatca accattccaa 60
cctgaagacc catgtccaat acattattat tcggactggt ttgtaaaaat tggacctcgc 120
aagtctgctc gcctagtaca actttgtgct ggtgaatatg gacacagagt tccaatacat 180
tatgaaatgt ttggcaatta tactatttca tgtgaaccac ttgaaataaa ttgtcaaaac 240
ccaccagttg gaagtctcat tgtacgttgt tcatatgatg ttgactttat ggagtatcac 300
gacgttcgtg ttgttctaga tttcatctaa acgaacaaac taaaatgtct gataatggac 360
cccaaccaaa tcagcgtagt gccccccgca ttacatttgg tggacccaca gattc 415

<210> SEQ ID NO 46
<211> LENGTH: 409
<212> TYPE: DNA
<213> ORGANISM: Human coronavirus

<400> SEQUENCE: 46
gctgcatttc accaagaatg tagtttacag tcatgtactc aacatcaacc atatgtagtt 60
gatgacccgt gtcctattca cttctattct aaatggtata ttagagtagg agctagaaaa 120
tcagcacctt taattgaatt gtgcstggat gaggctggtt ctaaatcacc cattcagtac 180
atcgatatcg gtaattatac agtttcctgt tyacctttta caattaattg ccaggaacct 240
aaattgggta gtcttgtagt gcgttgttcg ttctatgaag actttttaga gtatcatgac 300
gttcgtgttg ttttagattt catctaaacg aacaaactaa aatgtctgat aatggacccc 360
aaaatcagcg aaatgcaccc cgcattacgt ttggtggacc ctcagattc 409

<210> SEQ ID NO 47
<211> LENGTH: 409
<212> TYPE: DNA
<213> ORGANISM: Human coronavirus

<400> SEQUENCE: 47
gctgcatttc accaagaatg tagtttacag tcatgtactc aacatcaacc atatgtagtt 60
gatgacccgt gtcctattca cttctattct aaatggtata ttagagtagg agctagaaaa 120
tcagcacctt taattgaatt gtgcstggat gaggctggtt ctaaatcacc cattcagtac 180
atcgatatcg gtaattatac agtttcctgt tyacctttta caattaattg ccaggaacct 240
aaattgggta gtcttgtagt gcgttgttcg ttctatgaag actttttaga gtatcatgac 300
gttcgtgttg ttttagattt catctaaacg aacaaactaa aatgtctgat aatggacccc 360
aaaatcagcg aaatgcaccc cgcattacgt ttggtggacc ctcagattc 409

<210> SEQ ID NO 48
<211> LENGTH: 409
<212> TYPE: DNA
<213> ORGANISM: Human coronavirus

<400> SEQUENCE: 48
gctgcatttc accaagaatg tagtttacag tcatgtactc aacatcaacc atatgtagtt 60
gatgacccgt gtcctattca cttctattct aaatggtata ttagagtagg agctagaaaa 120
tcagcacctt taattgaatt gtgcstggat gaggctggtt ctaaatcacc cattcagtac 180
atcgatatcg gtaattatac agtttcctgt tyacctttta caattaattg ccaggaacct 240
aaattgggta gtcttgtagt gcgttgttcg ttctatgaag actttttaga gtatcatgac 300
gttcgtgttg ttttagattt catctaaacg aacaaactaa aatgtctgat aatggacccc 360
aaaatcagcg aaatgcaccc cgcattacgt ttggtggacc ctcagattc 409

CORONAVIRUS DETECTION

This invention relates to methods for detecting nucleic acid of severe acute respiratory syndrome coronavirus 2 (SARS-CoV-2), responsible for coronavirus disease 2019 (COVID-19), particularly for point-of-care (POC) testing, and to kits, primers, probes, sets of primers, sets of oligonucleotides, and oligonucleotides, and their use in the methods.

INCORPORATION BY REFERENCE OF SEQUENCE LISTING

The Sequence Listing in an ASCII text file, named as 41378_Sequence_Listing.txt of 16 KB, created on Sep. 22, 2022, and submitted to the United States Patent and Trademark Office via EFS-Web, is incorporated herein by reference.

The 2019-20 coronavirus pandemic is an ongoing pandemic of COVID-19 caused by SARS-CoV-2. First identified in Wuhan, Hubei, China, in December 2019, the outbreak was recognised as a pandemic by the World Health Organization (WHO) on 11 Mar. 2020. As of 18 Mar. 2020, more than 203,000 cases of COVID-19 have been reported in over 160 countries and territories, with major outbreaks in mainland China, Europe, Iran, and South Korea. More than 8,200 people have died and over 82,000 have recovered.

SARS-CoV-2 belongs to the broad family of viruses known as coronaviruses. Coronaviruses are named for the crown-like spikes on their surface. There are four main sub-groupings of coronaviruses, known as alpha, beta, gamma, and delta. The seven coronaviruses that can infect people are: 229E (alpha coronavirus); NL63 (alpha coronavirus); OC43 (beta coronavirus); HKU1 (beta coronavirus); MERS-COV (beta coronavirus that causes Middle East Respiratory Syndrome, or MERS); SARS-COV (beta coronavirus that causes severe acute respiratory syndrome, or SARS); and SARS-CoV-2.

Like other coronaviruses, SARS-CoV-2 has four structural proteins, known as the S (spike), E (envelope), M (membrane), and N (nucleocapsid) proteins. The N protein holds the RNA genome, and the S, E, and M proteins together create the viral envelope. The spike protein, which has been imaged at the atomic level using cryogenic electron microscopy, is the protein responsible for allowing the virus to attach to the membrane of a host cell.

SARS-CoV-2 is a positive-sense single-stranded RNA (+ssRNA) virus. Like the SARS-related coronavirus strain implicated in the 2003 SARS outbreak, SARS-CoV-2 is a member of the subgenus Sarbecovirus (beta-CoV lineage B). Its RNA sequence is approximately 30,000 bases in length (see the SARS-COV genome organisation shown in FIG. 1).

Being able to test, identify and treat individuals infected with SARS-CoV-2 without delay is critical. Nucleic acid testing (NAT) is state of the art for diagnosis of infectious disease, but requires highly-trained staff and specialized facilities available only in sophisticated, centralized laboratories. Current NATs also require samples to be sent frozen or refrigerated; with turnaround times of 2-3 days for results leading to 'loss-to-follow-up,' a common problem in developing countries. Despite draconian efforts by central and local authorities, Wuhan experiences long delays in testing results, especially in hospitals without NAT testing capacity. This limitation is also seen in other settings such as cruise ships. China is also experiencing amplicon contamination, causing false positives, a common problem for NATs. China infrastructure is stretched and experiencing some of the same problems for diagnostics seen in developing countries.

There is clearly an urgent need for a decentralized, point-of-care (POC) diagnostic test for COVID-19 for use in the community.

We have designed primers and probes specific to SARS-CoV-2, and a test has been developed with a sensitivity of at least 10 copies/reaction for 2 specific regions of the SARS-CoV-2 genome.

Primers and probes specific to SARS-CoV-2 (COVID-19) genome have been designed in the ORF1 and nucleocapsid (N) genes. Alignment of all 7 human coronaviruses was used during primer and probe selection, ensuring high specificity.

According to the invention there is provided a method for determining whether a sample includes severe acute respiratory syndrome coronavirus 2 (SARS-CoV-2) nucleic acid, which comprises amplifying nucleic acid of the sample, or amplifying nucleic acid derived from nucleic acid of the sample, by an isothermal amplification reaction using a forward nucleic acid amplification primer and a reverse nucleic acid amplification primer, wherein each nucleic acid amplification primer hybridises specifically to nucleic acid sequence that is conserved in SARS-CoV-2 nucleic acid, but not in other human coronavirus nucleic acid, or the complement thereof.

Optionally the other human coronavirus nucleic acid is human coronavirus 229E, SARS, HKU1, MERS, OC43, and NL63 nucleic acid.

Optionally the nucleic acid sequence that is conserved in SARS-CoV-2 nucleic acid, but not in other human coronavirus nucleic acid, comprises a contiguous nucleic acid sequence that is at least 19 nucleotides long.

Optionally the nucleic acid sequence that is conserved in SARS-CoV-2 nucleic acid is nucleic acid sequence that is conserved in the ORF1ab gene or the Nucleocapsid gene of SARS-CoV-2.

Conserved sequences may be identified by homology search, using tools such as BLAST, HMMER and Infernal. Homology search tools may take an individual nucleic acid sequence as input, or use statistical models generated from multiple sequence alignments of known related sequences. Statistical models such as profile-HMMs, and RNA covariance models which also incorporate structural information, can be helpful when searching for more distantly related sequences. Input sequences are then aligned against a database of sequences from related individuals or other species. The resulting alignments are then scored based on the number of matching bases, and the number of gaps or deletions generated by the alignment. Acceptable conservative substitutions may be identified using substitution matrices such as PAM and BLOSUM. Highly scoring alignments are assumed to be from homologous sequences. The conservation of a sequence may then be inferred by detection of highly similar homologs over a broad phylogenetic range.

Optionally conserved SARS-CoV-2 nucleic acid is nucleic acid comprising nucleic acid sequence that includes up to 2 mismatches per 20 nucleotides compared with a reference SARS-CoV-2 nucleic acid sequence.

Optionally conserved SARS-CoV-2 nucleic acid is nucleic acid comprising nucleic acid sequence that includes up to 1 mismatch per 20 nucleotides compared to a reference SARS-CoV-2 nucleic acid sequence.

Optionally conserved SARS-CoV-2 nucleic acid is nucleic acid comprising nucleic acid sequence that is identical to a reference SARS-CoV-2 nucleic acid sequence.

Multiple sequence alignments can be used to visualise conserved sequences. The CLUSTAL format includes a plain-text key to annotate conserved columns of the alignment, denoting conserved sequence (*), conservative mutations (:), semi-conservative mutations (.), and non-conservative mutations ( ). Software such as MacVector can be used to perform multiple sequence alignments.

Optionally a nucleic acid amplification primer hybridises specifically to nucleic acid sequence that is conserved in SARS-CoV-2 nucleic acid, or the complement thereof, if it hybridises under stringent conditions to the conserved SARS-CoV-2 nucleic acid sequence, or the complement thereof, but not other human coronavirus nucleic acid, or the complement thereof.

The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. The $T_m$ is the temperature under defined ionic strength and pH, at which 50% of the target sequence hybridises to a perfectly matched primer or probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1) DNA-DNA hybrids (Meinkoth and Wahl, Anal. Biochem., 138:267-284, 1984):

$$T_m = 81.5^\circ\text{ C.} + 16.6 \times \log_{10}[\text{Na}^+]^a + 0.41 \times \%\,[G/C^b] - 500 \times [L^c]^{-1} - 0.61 \times \%\text{ formamide};$$

2) DNA-RNA or RNA-RNA hybrids:

$$T_m = 79.8^\circ\text{ C.} + 18.5(\log_{10}[\text{Na}^+]^a) + 0.58(\%\,G/C^b) + 11.8(\%\,G/C^b)^2 - 820/L^c;$$

3) oligo-DNA or oligo-RNAs hybrids:
For <20 nucleotides: $T_m=2(I_n)$;
For 20-35 nucleotides: $T_m=22+1.46(I_n)$;

[a] or for other monovalent cation, but only accurate in the 0.01-0.4 M range.

[b] only accurate for % GC in the 30% to 75% range.

[c]L=length of duplex in base pairs.

[d] oligo, oligonucleotide; $1_n$, =effective length of primer=2×(no. of G/C)+(no. of NT).

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical stringent conditions (also referred to as high stringency hybridisation conditions) for DNA hybrids longer than 50 nucleotides encompass hybridisation at 65° C. in 1×SSC or at 42° C. in 1×SSC and 50% formamide, followed by washing at 65° C. in 0.3×SSC. The length of the hybrid is the anticipated length for the hybridising nucleic acid.

When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 g/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

Optionally the forward nucleic acid primer hybridizes specifically to nucleic acid sequence that is conserved in the ORF1ab gene of SARS-CoV-2, or the complement thereof.

Optionally the forward nucleic acid primer hybridizes specifically to nucleic acid sequence that is the complement of nucleic acid sequence that is conserved in the ORF1ab gene of SARS-CoV-2.

Optionally the forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4.

Optionally the reverse nucleic acid primer hybridizes specifically to nucleic acid sequence that is conserved in the ORF1ab gene of SARS-CoV-2, or the complement thereof.

Optionally the reverse nucleic acid primer hybridizes specifically to nucleic acid sequence that is conserved in the ORF1ab gene of SARS-CoV-2.

Optionally the reverse nucleic acid primer comprises a nucleic acid sequence: CAATAGTCTGAACAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7.

Optionally the forward and reverse nucleic acid amplification primers comprise respective nucleic acid sequences according to any of the combinations of forward and reverse primer sequences shown in Table 1 below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

TABLE 1

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |
| 6 | SEQ ID NO: 4 (SA_nCoV_F2) | SEQ ID NO: 7 (SA_nCoV_R2) |

Optionally the forward nucleic acid amplification primer comprises a nucleic acid sequence of SEQ ID NO: 1, and the reverse nucleic acid amplification primer comprises a nucleic acid sequence of SEQ ID NO: 5.

Optionally the forward nucleic acid primer hybridizes specifically to nucleic acid sequence that is conserved in the Nucleocapsid gene of SARS-CoV-2, or the complement thereof.

Optionally the forward nucleic acid primer hybridizes specifically to nucleic acid sequence that is the complement of nucleic acid sequence that is conserved in the Nucleocapsid gene of SARS-CoV-2.

Optionally the forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14.

Optionally the forward nucleic acid primer comprises a nucleic acid sequence of SEQ ID NO: 14.

Optionally the reverse nucleic acid primer hybridizes specifically to nucleic acid sequence that is conserved in the Nucleocapsid gene of SARS-CoV-2, or the complement thereof.

Optionally the reverse nucleic acid primer hybridizes specifically to nucleic acid sequence that is conserved in the Nucleocapsid gene of SARS-CoV-2.

Optionally the reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17.

Optionally the forward nucleic acid amplification primer comprises a nucleic acid sequence of SEQ ID NO: 14, and the reverse nucleic acid amplification primer comprises a nucleic acid sequence of SEQ ID NO: 16.

FIG. 2 shows a multiple sequence alignment of the ORF1ab region for all 7 human coronaviruses (229E, SARS, HKU1, MERS, OC43, and NL63, and SARS-CoV-2 sequences of several different isolates), and a bat SARS-like coronavirus sequence (SEQ ID NO: 34). The ORF1ab region sequences shown in the figure are as follows: 229E is represented by SEQ ID NO: 30; SARS CoV-2 GZ02 is represented by SEQ ID NO: 32; SARS CoV-2 ZS-B is represented by SEQ ID NO: 33; HKU1 is represented by SEQ ID NO: 31; MERS is represented by SEQ ID NO: 27; OC43 is represented by SEQ ID NO: 28; NL63 is represented by SEQ ID NO: 29; 2019-nCOV_MN988713_Atlanta is represented by SEQ ID NO: 35; 2019-nCOV_MN988669.1_WuhanUniversity is represented by SEQ ID NO: 36; and 2019-nCOV_MN908947.3_PublicHealth is represented by SEQ ID NO: 37. In the figure, SARS-CoV-2 is referred to by its previous provisional name "2019-nCOV" (2019 novel coronavirus). The locations in the SARS-CoV-2 ORF1ab gene sequence corresponding to the sequence of the forward primers of SEQ ID NOs: 1-3 (2019-nCoV-ARP1.1F, 2019-nCoV-ARP1.2F, 2019-nCoV-ARP1.3F, respectively), and to the reverse complement of sequence of the reverse primers of SEQ ID NOs: 5 and 6 (2019-nCoV-ARP1.1R, 2019-nCoV-ARP1.2R, respectively), are shown in FIG. 2. Lastly, the capture probes are shown as nCoV-ARCP1.1 and nCoV-ARCP1.2 (SEQ ID NOs: 8 and 9, respectively) along with the detector probes nCoV-ARDP1.1 and nCoV-ARDP1.2 (SEQ ID NOs: 11 and 12, respectively).

FIG. 3 shows a multiple sequence alignment of the nucleocapsid region for all 7 human coronaviruses (229E, SARS, HKU1, MERS, OC43, and NL63, and SARS-CoV-2 sequences of several different isolates), and a bat SARS-like coronavirus sequence (SEQ ID NO: 45). The nucleocapsid region sequences shown in the figure are as follows: OC43 is represented by SEQ ID NO: 39; HKU1 is represented by SEQ ID NO: 42; NL63 is represented by SEQ ID NO: 40; 229E is represented by SEQ ID NO: 41; MERS is represented by SEQ ID NO: 38; SARS CoV-2 ZS-B is represented by SEQ ID NO: 44; SARS CoV-2 GZ02 is represented by SEQ ID NO: 43; 2019-nCOV_MN988713 Atlanta is represented by SEQ ID NO: 46; 2019-nCOV_MN988669.1_WuhanUniversity is represented by SEQ ID NO: 47; and 2019-nCOV_MN908947.3_PublicHealth is represented by SEQ ID NO: 48. In the figure, SARS-CoV-2 is referred to by its previous provisional name "2019-nCOV" (2019 novel coronavirus). The locations in the SARS-CoV-2 nucleocapsid gene sequence corresponding to the sequence of the forward primer of SEQ ID NO: 14 (SA-nCoV-F2.3), and to the reverse complement of sequence of the reverse primers of SEQ ID NOs: 15-17 (SA-nCoV-R2.3, SA-nCoV-R2.4, SA-nCoV-R2.5, respectively), are shown in FIG. 3. Lastly, capture probe nCoV-CP2.3 (SEQ ID NO: 18) is shown along with the detector probes nCoV-DP2.3 and nCoV-DP2.4 (SEQ ID NOs: 19 and 20, respectively).

Nucleic acid may be derived from nucleic acid of the sample, for example by reverse transcribing SARS-CoV-2 nucleic acid of the sample, and amplifying a product of the reverse transcription by an isothermal nucleic acid amplification reaction using the forward and reverse nucleic acid amplification primers.

Optionally a method of the invention further comprises reverse transcribing SARS-CoV-2 RNA of the sample, and amplifying a product of the reverse transcription by an isothermal amplification reaction using the forward and reverse nucleic acid amplification primers.

Optionally the reverse nucleic acid primer further comprises a promoter sequence for a DNA-dependent RNA polymerase at its 5'-end, and reverse transcription is carried out using the reverse nucleic acid primer.

Any suitable method of isothermal nucleic acid amplification may be used in methods of the invention. Several suitable methods of isothermal nucleic acid amplification are known to the skilled person. Optionally the isothermal nucleic acid amplification is a transcription-based amplification. Such methods involve amplification of an RNA template using reverse transcriptase (RT), RNase H, and RNA polymerase activities, and include nucleic acid sequence-based amplification (NASBA), transcription-mediated amplification (TMA), and self-sustained sequence replication (3SR) (Chan and Fox, Rev. Med. Microbiol. 10:185-196 (1999); Guatelli et al., Proc. Natl. Acad. Sci. 87:1874-1878 (1990); Compton, Nature 350:91-92 (1991)). NASBA and 3SR use RT from Avian Myeloblastosis Virus (AMV) (which also has RNaseH activity), RNase H from *E. coli*, and T7 RNA polymerase. TMA uses Moloney Murine Leukemia Virus (MMLV) RT (which also has RNase H activity), and T7 RNA polymerase.

Isothermal amplification methods, such as transcription-based amplification methods, have several advantages over amplification using a Polymerase Chain Reaction (PCR). The reactions occur simultaneously in a single tube, and are carried out under isothermal conditions so a thermocycler is not required. The amplification reaction is faster than PCR ($1\times10^9$-fold amplification can be seen after five cycles, compared with $1\times10^6$-fold amplification after 20 cycles for PCR). DNA background does not interfere with transcription-based amplification, and so these methods are not affected by double stranded DNA contamination. The amplification product is single stranded and can be detected without any requirement for strand separation.

Optionally the reverse nucleic acid primer further comprises a promoter sequence for a DNA-dependent RNA polymerase at its 5'-end. Such a primer can be used for the reverse transcription and for a transcription-based isothermal amplification reaction, thereby minimising the number of primers required to carry out reverse transcription and isothermal nucleic acid amplification.

For example, the promoter sequence may be a T7 promoter sequence comprising: 5' taatacgactcactatag 3' (SEQ ID NO: 23). T7 RNA polymerase starts transcription at the underlined G in the promoter sequence. The polymerase then transcribes using the opposite strand as a template from 5'→3'. The first base in the transcript will be a G. Other examples of T7 promoter sequence for inclusion at the 5'-end of the reverse nucleic acid primer include a nucleic acid sequence of:

```
aattctaatacgactcactatagggagaagg (SEQ ID NO: 21)-
for use with 2019-CoV-ARP1.1R (SEQ ID NO: 5);

aattctaatacgactcactataggggaaaag (SEQ ID NO: 22)-
for use with SA_nCoV_R2.4 (SEQ ID NO: 16);

aattctaatacgactcactatagggaaagga (SEQ ID NO: 24)-
for use with 2019-CoV-ARP1.2R (SEQ ID NO: 6);

aattctaatacgactcactatagggaaagg (SEQ ID NO: 25)-
for use with SA_nCoV_R2 (SEQ ID NO: 7);

aattctaatacgactcactataggggaaaga (SEQ ID NO: 26)-
for use with SA_nCoV_R2.3 (SEQ ID NO: 15) or
SA_nCoV_R2.3 R2.5 (SEQ ID NO: 17)
```

A transcription-based isothermal amplification reaction suitable for use in methods of the invention is described below, with reference to FIG. 4.

An antisense Primer 1 comprises nucleic acid sequence complementary to a portion of a target RNA so that the primer can hybridise specifically to the target RNA (for example, SEQ ID NO: 5, 2019-CoV-ARP1.1R, reverse primer), and a single stranded-version of a promoter sequence for a DNA-dependent RNA polymerase at its 5'-end (for example, a T7 promoter sequence comprising SEQ ID NO: 21). Primer 1 is annealed to the RNA target. An RNA-dependent DNA polymerase extends Primer 1 to synthesise a complementary DNA (cDNA) copy of the RNA target. A DNA/RNA duplex-specific ribonuclease digests the RNA of the RNA-cDNA hybrid. A sense Primer 2 comprises nucleic acid sequence complementary to a portion of the cDNA. Primer 2 is annealed to the cDNA downstream of the part of the cDNA formed by Primer 1. Primer 2 is extended by a DNA-dependent DNA polymerase to produce a second DNA strand which extends through the DNA-dependent RNA polymerase promoter sequence at one end (thereby forming a double stranded promoter). This promoter is used by a DNA-dependent RNA polymerase to synthesise a large number of RNAs complementary to the original target sequence. These RNA products then function as templates for a cyclic phase of the reaction, but with the primer annealing steps reversed, i.e., Primer 2 followed by Primer 1.

In a variation of this method, Primer 2 may also include a single stranded version of a promoter sequence for the DNA-dependent RNA polymerase. This results in production of RNAs with the same sense as the original target sequence (as well as RNAs complementary to the original target sequence).

In some conventional isothermal transcription-based amplification reactions it is known to cleave the target RNA at the 5'-end before it serves as the template for cDNA synthesis. An enzyme with RNase H activity is used to cleave the RNA portion of an RNA-DNA hybrid formed by adding an oligonucleotide (a cleavage oligonucleotide) having a sequence complementary to the region overlapping and adjacent to the 5'-end of the target RNA. The cleavage oligonucleotide may have its 3'-terminal-OH appropriately modified to prevent extension reaction. Whilst in some embodiments of the invention a cleavage oligonucleotide could be used, it is preferred that a method of the invention is carried out in the absence of a cleavage oligonucleotide thereby simplifying the amplification reaction and the components required.

Isothermal nucleic acid amplification is advantageous because it can readily be used in resource-limited settings. Such methods do not require the use of thermal cyclers which may not be available in resource-limited settings. Examples of suitable methods are described in WO 2008/090340 and Lee et al., Journal of Infectious Diseases 2010; 201(S1): S65-S71.

Examples of suitable reagents for carrying out reverse transcription of RNA, and for isothermal amplification of a product of the reverse transcription, are given in WO 2008/090340, and include, for example, the following enzyme activities: an RNA-dependent DNA polymerase, a DNA-dependent DNA polymerase, a DNA/RNA duplex-specific ribonuclease, and a DNA-dependent RNA polymerase.

It will be appreciated that in addition to the required enzyme activities, it will also be necessary to provide appropriate nucleotide triphosphates (for transcription-based amplifications, ribonucleotide triphosphates (rNTPs, i.e. rATP, rGTP, rCTP, and rUTP), and deoxyribonucleotide triphosphates (dNTPs, i.e. dATP, dGTP, dCTP, and dTTP) are required), appropriate primers for specific amplification of the target nucleic acid, a suitable buffer for carrying out the amplification reaction, and any necessary cofactors (for example magnesium ions) required by the enzyme activities. Examples of suitable buffers include Tris-HCl, HEPES, or acetate buffer. A suitable salt may be provided, such as potassium chloride or sodium chloride. Suitable concentrations of these components may readily be determined by the skilled person. Suitable rNTP concentrations are typically in the range 0.25-5 mM, or 0.5-2.5 mM. Suitable dNTP concentrations are typically in the range 0.25-5 mM dNTP, or 0.5-2.5 mM. Suitable magnesium ion concentrations are typically in the range 5-15 mM.

Some conventional transcription-based amplification methods use very high amounts of T7 RNA polymerase (for example 142 or more units, where one unit incorporates 1 nmole of labelled nucleotide into acid insoluble material in 1 hour at 37° C. under standard assay conditions, such as: 40 mM Tris-HCl (pH8.0), 50 mM NaCl, 8 mM $MgCl_2$, 5 mM DTT, 400 μM rNTPs, 400 μM [$^3$H]-UTP (30 cpm/pmoles), 20 μg/ml T7 DNA, 50 μg/ml BSA, 100 μl reaction volume, 37° C., 10 min.). Methods of the invention can be carried out using significantly less T7 RNA polymerase than such conventional methods, thereby reducing cost. For example, methods of the invention can be carried out using less than 142 units of a DNA-dependent RNA polymerase (for example T7 RNA polymerase), suitably less than 100 units or less than 50 units, such as 30-40 units.

Optionally nucleic acid of the sample is isolated before reverse transcribing SARS-CoV-2 RNA of the sample present in the isolated nucleic acid.

Many suitable methods for isolation of nucleic acid are known to the skilled person. Some methods use chaotropic agents, such as guanidinium thiocyanate, and organic solvents to lyse cells, and denature proteins. For example, Boom et al. (Journal of Clinical Microbiology, 1990, Vol. 28 (3): 495-503) describes methods in which a sample is contacted with silica particles in the presence of a lysis/binding buffer containing guanidinium thiocyanate. Released nucleic acid binds to the silica particles, which are then washed with a wash buffer containing guanidinium thiocyanate, then with ethanol, and then acetone. The bound nucleic acid is subsequently eluted in an aqueous low salt buffer (Tris-HCl, EDTA, pH 8.0).

Some methods avoid the requirement for chaotropic salts and organic solvents. For example, Hourfar et al. (Clinical Chemistry, 2005, 51 (7): 1217-1222) describes methods in which a sample is mixed with magnetic silica particles in the presence of a lysis/binding buffer containing a kosmotropic salt (ammonium sulphate) before addition of proteinase K. Following separation, the magnetic particles are washed with wash buffer containing proteinase K, and eluted in elution buffer (Tris-HCl, pH 8.5) at 80° C. Other suitable methods are described in WO 2010/015835.

Isolation of nucleic acid may be carried out using conventional binding buffers and/or elution buffers for use with a solid phase that is able to bind the nucleic acid in the presence of binding buffer at a first pH, and from which the nucleic acid can be eluted at a second pH.

Optionally the solid phase comprises an ionisable group, which changes charge according to the ambient conditions. The pKa of the ionisable group is appropriate to the conditions at which it is desired to bind nucleic acid to and release nucleic acid from the solid phase.

Generally, nucleic acid will bind to the solid phase at a pH below or roughly equal to the pKa, and will be released at a higher pH (usually above the pKa). Suitable solid phases for binding a nucleic acid at a first pH, and elution of bound nucleic acid at a second pH that is higher than the first pH, are well known to those of ordinary skill in the art. For example, at the first pH the solid phase may comprise a positive charge, and at the second pH the solid phase may have a less positive, neutral, or negative charge. Alternatively or additionally, at the first pH the solid phase may comprise a neutral or less negative charge, and at the second pH the solid phase may have a negative or more negative charge. Such changes in charge allow the nucleic acid to be adsorbed to the solid phase at the first pH, and released at the second pH.

For example, the solid phase may comprise a negatively ionisable group with a pKa between the first and second pH. Nucleic acid will bind to the solid phase when the solid phase is neutral or less negatively charged, and will be released when the solid phase is negatively or more negatively charged. Alternatively, or additionally, the solid phase may comprise a positively ionisable group with a pKa between the first and second pH. Nucleic acid will bind to the solid phase when the solid phase is positively charged, and will be released when the solid phase is neutral or less positively charged.

Examples of solid phases that may be used for extraction of nucleic acid include solid phases that comprise inorganic oxides, such as silica or glass (for example, as described in Boom et al, or Hourfar et al), or aluminium oxide, sugar polymers, or charge-switch materials (for example, as described in WO 02/48164).

The solid phase may be in any suitable form, for example comprising a membrane, gel, or particles, for example magnetic particles. Silica membrane or gel, and magnetic silica particles are preferred examples. Silica membrane is particularly preferred. This is less expensive than magnetic silica particles (used for example by Hourfar, et al.) and does not require refrigerated storage, unlike magnetic silica particles.

The solid phase may be a solid phase to which binding of nucleic acid is enhanced by the presence of a kosmotropic agent. Optionally binding of the nucleic acid to the solid phase is carried out in the presence of a kosmotropic agent. Such agents are known to enhance binding of nucleic acid to solid phases such as silica-based solid phases.

The terms "chaotropic" and "kosmotropic" agent originate from the Hofmeister series (Cacace et al., Q Rev Biophys 1997; 30:241-77), which divides these agents depending on their influence on the structure of macromolecules and water. A chaotrope may be defined as a substance that breaks solvent structure, and a kosmotrope as a substance that enhances solvent structure. FIG. 1 of Cacace et al shows the Hofmeister series and commonly occurring organic solutes with effects on protein structure/function. Examples of chaotropic agents are known to those in the art, and include sodium iodide, sodium perchlorate, guanidinium thiocyanate and guanidinium hydrochloride. Examples of kosmotropic agents are known to those in the art, and include ammonium sulphate and lithium chloride.

Optionally lysis is carried out using the binding buffer. Binding buffers that may be used for cell lysis are known to those of ordinary skill in the art. The lysis buffer used by Boom et al. comprises guanidinium thiocyanate, Tris hydrochloride, pH 6.4, EDTA (adjusted to pH 8), and Triton X-100. Optionally, the lysis buffer does not include a chaotropic agent. For example, a lysis/binding buffer that comprises a kosmotropic agent may be used. Optionally the buffer is an acidic buffer, suitably a strong acidic buffer with a pKa (25° C.) in the range 3-5.

Optionally a method of the invention further comprises capturing a product of the isothermal amplification reaction by hybridising nucleic acid of the product to a nucleic acid capture probe, wherein the capture probe hybridises specifically to nucleic acid sequence that is conserved in SARS-CoV-2 nucleic acid, but not in other human coronavirus nucleic acid, or the complement thereof.

Optionally the other human coronavirus nucleic acid is human coronavirus 229E, SARS, HKU1, MERS, OC43, and NL63 nucleic acid.

Optionally the nucleic acid sequence that is conserved in SARS-CoV-2 nucleic acid, but not in other human coronavirus nucleic acid, comprises a contiguous nucleic acid sequence that is at least 19 nucleotides long.

Optionally a capture probe hybridises specifically to nucleic acid sequence that is conserved in SARS-CoV-2 nucleic acid, or the complement thereof, if it hybridises under stringent conditions to nucleic acid sequence that is conserved in SARS-CoV-2 nucleic acid, or the complement thereof, but not to other human coronavirus nucleic acid, or the complement thereof.

Optionally the forward and reverse nucleic acid primers hybridise specifically to nucleic acid sequence that is conserved in the ORF1ab gene of SARS-CoV-2, or the complement thereof, and the capture probe hybridizes specifically to nucleic acid sequence that is conserved in the ORF1ab gene of SARS-CoV-2, or the complement thereof.

Optionally the capture probe comprises a nucleic acid of sequence: GGCAGTGAGGACAATCAGCAACTAC (SEQ ID NO: 8), GAGGACAATCAGACAACTACTATTC (SEQ ID NO: 9), ACCCGTCCTTGATTGGCTTG (SEQ ID NO: 10), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 8, 9, or 10, or the complement thereof.

Optionally the capture probe comprises a nucleic acid sequence of SEQ ID NO: 9.

Optionally the forward and reverse nucleic acid primers hybridise specifically to nucleic acid sequence that is conserved in the nucleocapsid gene of SARS-CoV-2, or the complement thereof, and the capture probe hybridizes specifically to nucleic acid sequence that is conserved in the nucleocapsid gene of SARS-CoV-2, or the complement thereof.

Optionally the capture probe comprises a nucleic acid of sequence: CTGGTTCTAAATCACCCATTCA (SEQ ID NO: 18), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 18, or the complement thereof.

Optionally the capture probe comprises a nucleic acid of SEQ ID NO: 18.

Optionally a method of the invention further comprises detecting a product of the isothermal amplification reaction by hybridising the product to a nucleic acid detector probe, wherein the detector probe hybridises specifically to nucleic acid sequence that is conserved in SARS-CoV-2 nucleic acid, but not in other human coronavirus nucleic acid, or the complement thereof.

Optionally the other human coronavirus nucleic acid is human coronavirus 229E, SARS, HKU1, MERS, OC43, and NL63 nucleic acid.

Optionally the nucleic acid sequence that is conserved in SARS-CoV-2 nucleic acid, but not in other human coronavirus nucleic acid, comprises a contiguous nucleic acid sequence that is at least 19 nucleotides long.

Optionally a detector probe hybridises specifically to nucleic acid sequence that is conserved in SARS-CoV-2 nucleic acid, or the complement thereof, if it hybridises under stringent conditions to nucleic acid sequence that is conserved in SARS-CoV-2 nucleic acid, or the complement thereof, but not to other human coronavirus nucleic acid, or the complement thereof.

Optionally the forward and reverse nucleic acid primers hybridise specifically to nucleic acid sequence that is conserved in the ORF1ab gene of SARS-CoV-2, or the complement thereof, and the detector probe hybridizes specifically to nucleic acid sequence that is conserved in the ORF1ab gene of SARS-CoV-2, or the complement thereof.

Optionally the detector probe comprises a nucleic acid sequence of: CAAACAATTGTTGAGGTTCAACCTC ID (SEQ NO: 11), GAGGTTCAACCTCAATTAGAGATGG (SEQ ID NO: 12), GGAAGGTGTAGAGTTTCTTAGAGAC (SEQ ID NO: 13), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, 12, or 13, or the complement thereof.

Optionally a method of the invention comprises amplifying with forward and reverse nucleic acid amplification primers, capture of amplification product with capture probe, and detection of amplification product with detector probe, wherein the amplification primers and capture and detector probes comprise respective nucleic acid sequences according to any of the combinations of forward and reverse primer sequences, and capture probe (CP) and detector probe (DP) shown in Table 2 below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

TABLE 2

| Combination | Forward | Reverse | CP | DP |
|---|---|---|---|---|
| 1 | SEQ ID NO: 1 (nCoV-ARP1.1F) | SEQ ID NO: 5 (nCoV-ARP1.1R) | SEQ ID NO: 9 (nCoV-ARCP1.2) | SEQ ID NO: 12 (nCoV-ARDP1.2) |
| 2 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 11 (nCoV-ARDP1.1) |
| 3 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 12 (nCoV-ARDP1.2) |
| 4 | SEQ ID NO: 2 (nCoV-ARP1.2F) | SEQ ID NO: 5 (nCoV-ARP1.1R) | SEQ ID NO: 9 (nCoV-ARCP1.2) | SEQ ID NO: 12 (nCoV-ARDP1.2) |
| 5 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 11 (nCoV-ARDP1.1) |
| 6 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 12 (nCoV-ARDP1.2) |

TABLE 2-continued

| Combination | Forward | Reverse | CP | DP |
|---|---|---|---|---|
| 7 | SEQ ID NO: 3 (nCoV-ARP1.3F) | SEQ ID NO: 5 (nCoV-ARP1.1R) | SEQ ID NO: 9 (nCoV-ARCP1.2) | SEQ ID NO: 12 (nCoV-ARDP1.2) |
| 8 | SEQ ID NO: 2 (nCoV-ARP1.2F) | SEQ ID NO: 6 (nCoV-ARP1.2R) | SEQ ID NO: 8 (nCoV-ARCP1.1) | SEQ ID NO: 11 (nCoV-ARDP1.1) |
| 9 | SEQ ID NO: 3 (nCoV-ARP1.3F) | SEQ ID NO: 6 (nCoV-ARP1.2R) | SEQ ID NO: 8 (nCoV-ARCP1.1) | SEQ ID NO: 11 (nCoV-ARDP1.1) |
| 10 | SEQ ID NO: 4 (SA_nCoV_F2) | SEQ ID NO: 7 (SA_nCoV_R2) | SEQ ID NO: 10 (SA_nCoV_CP2) | SEQ ID NO: 13 (SA_nCoV_DP2) |

Optionally the detector probe comprises a nucleic acid sequence of SEQ ID NO: 12.

Optionally the forward and reverse nucleic acid primers hybridise specifically to nucleic acid sequence that is conserved in the nucleocapsid gene of SARS-CoV-2, or the complement thereof, and the detector probe hybridizes specifically to nucleic acid sequence that is conserved in the nucleocapsid gene of SARS-CoV-2, or the complement thereof.

Optionally the detector probe comprises a nucleic acid sequence of: GAACCTAAATTGGGTAGTCTTGTAG (SEQ ID NO: 19), GGAACCTAAATTGGGTAGTCTTG (SEQ ID NO: 20), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 19 or 20, or the complement thereof.

Optionally the detector probe comprises a nucleic acid sequence of SEQ ID NO: 19.

The locations in the SARS-CoV-2 ORF1ab gene sequence corresponding to the sequence of the capture probes of SEQ ID NOs: 8,9 (2019-nCoV-AR-CP1.1, 2019-nCoV-AR-CP1.2, respectively), and the detector probes of SEQ ID NOs: 11, 12 (2019-nCoV-AR-DP1.1, 2019-nCoV-AR-DP1.2, respectively), are shown in FIG. 2.

The locations in the SARS-CoV-2 nucleocapsid gene sequence corresponding to the sequence of the capture probe of SEQ ID NO: 18 (SA-nCoV-CP2.3), and the detector probe of SEQ ID NOs: 19, 20 (SA-nCoV-DP2.3, SA-nCoV-DP2.4, respectively), are shown in FIG. 3.

Sequence identity between nucleic acid sequences can be determined by comparing an alignment of the sequences. When an equivalent position in the compared sequences is occupied by the same nucleotide, then the molecules are identical at that position. Scoring an alignment as a percentage of identity is a function of the number of identical nucleotides at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector. Examples include MatGat (Campanella et al., 2003, BMC Bioinformatics 4:29; program available from http://bitincka.com/ledion/matgat), Gap (Needleman & Wunsch, 1970, J. Mol. Biol. 48:443-453), FASTA (Altschul et al., 1990, J. Mol. Biol. 215:403-410; program available from http://www.ebi.ac.uk/fasta), Clustal W 2.0 and X 2.0 (Larkin et al., 2007, Bioinformatics 23:2947-2948; program available from http://www.ebi.ac.uk/tools/clustalw2) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp 1-44, Addison Wesley; programs available from http://www.ebi.ac.uk/tools/emboss/align). All programs may be run using default parameters.

For example, sequence comparisons may be undertaken using the “needle” method of the EMBOSS Pairwise Alignment Algorithms, which determines an optimum alignment (including gaps) of two sequences when considered over their entire length and provides a percentage identity score.

Optionally the detector probe is labelled with a detectable label. Optionally the label is a visually detectable label (i.e. a label that is detectable by eye, without the aid of instrumentation).

Examples of suitable visually detectable labels include colloidal metal sol particles, latex particles, or textile dye particles. An example of colloidal metal sol particles is colloidal gold particles.

Optionally capture and/or detection of the product of the isothermal amplification reaction is carried out by chromatographic dipstick assay.

A product of the isothermal nucleic acid amplification may be labelled with a visually detectable label, and captured and detected using a chromatographic test strip, for example as described in WO 2008/090340, and Lee et al., Journal of Infectious Diseases 2010; 201 (S1): S65-S71.

Optionally the sample is a biological sample, for example a biological sample obtained from a subject suspected of being infected with SARS-CoV-2. Optionally the sample is a swab sample obtained from a subject suspected of being infected with SARS-CoV-2. Optionally the sample is a nasopharyngeal or a throat swab sample obtained from a subject suspected of being infected with SARS-CoV-2.

Optionally a method of the invention is an in vitro method.

Optionally a method of the invention comprises amplifying nucleic acid of the sample, or amplifying nucleic acid derived from nucleic acid of the sample, by an isothermal amplification reaction using a first forward nucleic acid amplification primer and a first reverse nucleic acid amplification primer, and a second forward nucleic acid amplification primer and a second reverse nucleic acid amplification primer, wherein each nucleic acid amplification primer hybridises specifically to nucleic acid sequence that is conserved in SARS-CoV-2 nucleic acid, but not in other human coronavirus nucleic acid, or the complement thereof, and wherein the first forward nucleic acid amplification primer and the first reverse nucleic acid amplification primer hybridise specifically to nucleic acid sequence that is conserved in the ORF1ab gene of SARS-CoV-2 nucleic acid, or the complement thereof, and the second forward nucleic acid amplification primer and the second reverse nucleic acid amplification primer hybridise specifically to nucleic acid sequence that is conserved in the nucleocapsid gene of SARS-CoV-2 nucleic acid, or the complement thereof.

Optionally a method of the invention further comprises capturing a product of the isothermal amplification reaction using the first forward nucleic acid amplification primer and the first reverse nucleic acid amplification primer by hybridising nucleic acid of the product to a first nucleic acid capture probe, wherein the first capture probe hybridises specifically to nucleic acid sequence that is conserved in SARS-CoV-2 nucleic acid, but not in other human coronavirus nucleic acid, or the complement thereof, and capturing a product of the isothermal amplification reaction using the second forward nucleic acid amplification primer and the second reverse nucleic acid amplification primer by hybridising nucleic acid of the product to a second nucleic acid capture probe, wherein the second capture probe hybridises specifically to nucleic acid sequence that is conserved in SARS-CoV-2 nucleic acid, but not in other human coronavirus nucleic acid, or the complement thereof, and wherein the first capture probe hybridises specifically to nucleic acid sequence that is conserved in the ORF1ab gene of SARS-CoV-2 nucleic acid, or the complement thereof, and the second capture probe hybridises specifically to nucleic acid sequence that is conserved in the nucleocapsid gene of SARS-CoV-2 nucleic acid, or the complement thereof.

Optionally a method of the invention further comprises detecting a product of the isothermal amplification reaction using the first forward nucleic acid amplification primer and the first reverse nucleic acid amplification primer by hybridising nucleic acid of the product to a first nucleic acid detector probe, wherein the first detector probe hybridises specifically to nucleic acid sequence that is conserved in SARS-CoV-2 nucleic acid, but not in other human coronavirus nucleic acid, or the complement thereof, and detecting a product of the isothermal amplification reaction using the second forward nucleic acid amplification primer and the second reverse nucleic acid amplification primer by hybridising nucleic acid of the product to a second nucleic acid detector probe, wherein the second detector probe hybridises specifically to nucleic acid sequence that is conserved in SARS-CoV-2 nucleic acid, but not in other human coronavirus nucleic acid, or the complement thereof, and wherein the first detector probe hybridises specifically to nucleic acid sequence that is conserved in the ORF1ab gene of SARS-CoV-2 nucleic acid, or the complement thereof, and the second detector probe hybridises specifically to nucleic acid sequence that is conserved in the nucleocapsid gene of SARS-CoV-2 nucleic acid, or the complement thereof.

Optionally the first forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4, or the complement thereof.

Optionally the first reverse nucleic acid primer comprises a nucleic acid sequence: CAATAGTCTGAACAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7, or the complement thereof.

Optionally the first forward and reverse nucleic acid amplification primers comprise respective nucleic acid sequences according to any of the combinations of forward and reverse primer sequences shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |
| 6 | SEQ ID NO: 4 (SA_nCoV_F2) | SEQ ID NO: 7 (SA_nCoV_R2) |

Optionally the first forward nucleic acid amplification primer comprises a nucleic acid sequence of SEQ ID NO: 1, and the first reverse nucleic acid amplification primer comprises a nucleic acid sequence of SEQ ID NO: 5.

Optionally the second forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14, or the complement thereof.

Optionally the second reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17, or the complement thereof.

Optionally the second forward nucleic acid amplification primer comprises a nucleic acid sequence of SEQ ID NO: 14, and the second reverse nucleic acid amplification primer comprises a nucleic acid sequence of SEQ ID NO: 16.

Optionally the first and/or second reverse nucleic acid primer further comprises a promoter sequence for a DNA-dependent RNA polymerase at its 5'-end for reverse transcription of SARS-CoV-2 RNA using the reverse nucleic acid primer.

Optionally the first capture probe comprises a nucleic acid of sequence: GGCAGTGAGGACAATCAGCAACTAC (SEQ ID NO: 8), GAGGACAATCAGACAACTACTATTC (SEQ ID NO: 9), ACCCGTCCTTGATTGGCTTG (SEQ ID NO: 10), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 8, 9, or 10, or the complement thereof.

Optionally the first capture probe comprises a nucleic acid sequence of SEQ ID NO: 9.

Optionally the second capture probe comprises a nucleic acid of sequence: CTGGTTCTAAATCACCCATTCA (SEQ ID NO: 18), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 18, or the complement thereof.

Optionally the first detector probe comprises a nucleic acid sequence of: CAAACAATTGTTGAGGTTCAACCTC ID (SEQ. NO: 11), GAGGTTCAACCTCAATT-AGAGATGG (SEQ ID NO: 12), GGAAGGTGTAGAGTTTCTTAGAGAC (SEQ ID NO: 13), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, 12, or 13, or the complement thereof.

Optionally the first forward and reverse amplification primers, and the first capture and detector probes comprise respective nucleic acid sequences according to any of the combinations of forward and reverse primer sequences, and capture probe (CP) and detector probe (DP) shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

forward and reverse amplification primers specific for the nucleocapsid gene (and optional capture and detection with probes specific to the ORF1ab and nucleocapsid genes), provides methods with exceptional sensitivity and specificity.

For embodiments of a method of the invention comprising an isothermal amplification reaction using a first forward nucleic acid amplification primer and a first reverse nucleic acid amplification primer, and a second forward nucleic acid amplification primer and a second reverse nucleic acid amplification primer, capture and/or detection of the product of the isothermal amplification reactions may be carried out by chromatographic dipstick assay using a chromatographic test strip. The test strip may comprise a first capture zone for capturing a product of the amplification reaction using the first forward and reverse nucleic acid amplification primers, and a second, separate capture zone for capturing a product of the amplification reaction using the second forward and reverse nucleic acid amplification primers.

Methods of the invention are particularly useful as POC tests for testing or screening for SARS-CoV-2 infection. In particular, methods of the invention can be carried out rapidly, without use of laboratory facilities or thermal cyclers. SARS-CoV-2 infection can be potentially be detected using a method of the invention before the subject is showing symptoms of COVID-19. Once a subject has been identified as being infected with SARS-CoV-2, they can be isolated, administered appropriate treatment, and the infection can be monitored.

The invention also provides a kit for carrying out a method of the invention.

| Combination | Forward | Reverse | CP | DP |
|---|---|---|---|---|
| 1 | SEQ ID NO: 1 (nCoV-ARP1.1F) | SEQ ID NO: 5 (nCoV-ARP1.1R) | SEQ ID NO: 9 (nCoV-ARCP1.2) | SEQ ID NO: 12 (nCoV-ARDP1.2) |
| 2 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 11 (nCoV-ARDP1.1) |
| 3 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 12 (nCoV-ARDP1.2) |
| 4 | SEQ ID NO: 2 (nCoV-ARP1.2F) | SEQ ID NO: 5 (nCoV-ARP1.1R) | SEQ ID NO: 9 (nCoV-ARCP1.2) | SEQ ID NO: 12 (nCoV-ARDP1.2) |
| 5 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 11 (nCoV-ARDP1.1) |
| 6 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 12 (nCoV-ARDP1.2) |
| 7 | SEQ ID NO: 3 (nCoV-ARP1.3F) | SEQ ID NO: 5 (nCoV-ARP1.1R) | SEQ ID NO: 9 (nCoV-ARCP1.2) | SEQ ID NO: 12 (nCoV-ARDP1.2) |
| 8 | SEQ ID NO: 2 (nCoV-ARP1.2F) | SEQ ID NO: 6 (nCoV-ARP1.2R) | SEQ ID NO: 8 (nCoV-ARCP1.1) | SEQ ID NO: 11 (nCoV-ARDP1.1) |
| 9 | SEQ ID NO: 3 (nCoV-ARP1.3F) | SEQ ID NO: 6 (nCoV-ARP1.2R) | SEQ ID NO: 8 (nCoV-ARCP1.1) | SEQ ID NO: 11 (nCoV-ARDP1.1) |
| 10 | SEQ ID NO: 4 (SA_nCoV_F2) | SEQ ID NO: 7 (SA_nCoV_R2) | SEQ ID NO: 10 (SA_nCoV_CP2) | SEQ ID NO: 13 (SA_nCoV_DP2) |

Optionally the first detector probe comprises a nucleic acid sequence of SEQ ID NO: 12.

Optionally the second detector probe comprises a nucleic acid sequence of: GAACCTAAATTGGGTAGTCTTGTAG (SEQ ID NO: 19), GGAACCTAAATTGGGTAGTCTTG (SEQ ID NO: 20), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 19 or 20, or the complement thereof.

Optionally the second detector probe comprises a nucleic acid sequence of SEQ ID NO: 19.

Amplification using first forward and reverse amplification primers specific for the ORF1ab gene, and second There is also provided according to the invention a kit for determining whether a sample includes SARS-CoV-2 nucleic acid, which comprises:

a forward nucleic acid amplification primer and a reverse nucleic acid amplification primer, for amplifying a template nucleic acid by an isothermal amplification reaction, wherein each nucleic acid amplification primer hybridises specifically to nucleic acid sequence that is conserved in SARS-CoV-2 nucleic acid, but not in other human coronavirus nucleic acid, or the complement thereof;

a nucleic acid capture probe, wherein the capture probe hybridises specifically to nucleic acid sequence that is conserved in SARS-CoV-2 nucleic acid, but not in other human coronavirus nucleic acid, or the complement thereof; and/or a nucleic acid detector probe, wherein the detector probe hybridises specifically to nucleic acid sequence that is conserved in SARS-CoV-2 nucleic acid, but not in other human coronavirus nucleic acid, or the complement thereof, optionally wherein the detector probe comprises a detectable label for labelling a product of the isothermal nucleic acid amplification.

Optionally the other human coronavirus nucleic acid is human coronavirus 229E, SARS, HKU1, MERS, OC43, and NL63 nucleic acid.

The forward and reverse nucleic acid amplification primers, or the capture and/or detector probes, of a kit of the invention may be any of the forward and reverse nucleic acid amplification primers, or any of the capture and/or detector probes, or any of the combinations of primers and/or probes as recited herein for methods of the invention.

Optionally the nucleic acid sequence that is conserved in SARS-CoV-2 nucleic acid, but not in other human coronavirus nucleic acid, comprises a contiguous nucleic acid sequence that is at least 19 nucleotides long.

Optionally the forward nucleic acid primer hybridizes specifically to nucleic acid sequence that is conserved in the ORF1ab gene of SARS-CoV-2, or the complement thereof.

Optionally the forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4.

Optionally the reverse nucleic acid primer hybridizes specifically to nucleic acid sequence that is conserved in the ORF1ab gene of SARS-CoV-2, or the complement thereof.

Optionally the reverse nucleic acid primer comprises a nucleic acid sequence: CAATAGTCTGAACAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7.

Optionally the forward and reverse nucleic acid amplification primers comprise respective nucleic acid sequences according to any of the combinations of forward and reverse primer sequences shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |

-continued

| Combination | Forward | Reverse |
|---|---|---|
| 6 | SEQ ID NO: 4 (SA_nCoV_F2) | SEQ ID NO: 7 (SA_nCoV_R2) |

Optionally the forward nucleic acid amplification primer comprises a nucleic acid sequence of SEQ ID NO: 1, and the reverse nucleic acid amplification primer comprises a nucleic acid sequence of SEQ ID NO: 5.

Optionally the forward nucleic acid primer hybridizes specifically to nucleic acid sequence that is conserved in the nucleocapsid gene of SARS-CoV-2, or the complement thereof.

Optionally the forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14.

Optionally the reverse nucleic acid primer hybridizes specifically to nucleic acid sequence that is conserved in the nucleocapsid gene of SARS-CoV-2, or the complement thereof.

Optionally the reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17.

Optionally the forward nucleic acid amplification primer comprises a nucleic acid sequence of SEQ ID NO: 14, and the reverse nucleic acid amplification primer comprises a nucleic acid sequence of SEQ ID NO: 16.

Optionally the reverse nucleic acid primer further comprises a promoter sequence for a DNA-dependent RNA polymerase at its 5'-end for reverse transcription of SARS-CoV-2 RNA using the reverse nucleic acid primer.

Optionally the forward and reverse nucleic acid primers hybridise specifically to nucleic acid sequence that is conserved in the ORF1ab gene of SARS-CoV-2, or the complement thereof, and the capture probe hybridizes specifically to nucleic acid sequence that is conserved in the ORF1ab gene of SARS-CoV-2, or the complement thereof.

Optionally the capture probe comprises a nucleic of sequence: acid GGCAGTGAGGACAATCAGCAACTAC (SEQ ID NO: 8), GAGGACAATCAGACAACTACTATTC (SEQ ID NO: 9), ACCCGTCCTTGATTGGCTTG (SEQ ID NO: 10), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 8, 9, or 10, or the complement thereof.

Optionally the capture probe comprises a nucleic acid sequence of SEQ ID NO: 9.

Optionally the forward and reverse nucleic acid primers hybridise specifically to nucleic acid sequence that is conserved in the nucleocapsid gene of SARS-CoV-2, or the complement thereof, and the capture probe hybridizes specifically to nucleic acid sequence that is conserved in the nucleocapsid gene of SARS-CoV-2, or the complement thereof.

Optionally the capture probe comprises a nucleic acid of sequence: CTGGTTCTAAATCACCCATTCA (SEQ ID NO: 18), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 18, or the complement thereof.

Optionally the forward and reverse nucleic acid primers hybridise specifically to nucleic acid sequence that is conserved in the ORF1ab gene of SARS-CoV-2, or the complement thereof, and the detector probe hybridizes specifically to nucleic acid sequence that is conserved in the ORF1ab gene of SARS-CoV-2, or the complement thereof.

Optionally the detector probe comprises a nucleic acid sequence of: CAAACAATTGTTGAGGTTCAACCTC (SEQ ID NO: 11), GAGGTTCAACCTCAATT-AGAGATGG (SEQ ID NO: 12), GGAAGGTGTAGAGTTTCTTAGAGAC (SEQ ID NO: 13), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, 12, or 13, or the complement thereof.

Optionally a kit of the invention comprises forward and reverse amplification primers, and capture and detector probes comprising respective nucleic acid sequences according to any of the combinations of forward and reverse primer sequences, and capture probe (CP) and detector probe (DP) shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

95%, 96%, 97%, 98%, or 99% identity along its entire length with a nucleic acid sequence of SEQ ID NO: 19 or 20, or the complement thereof.

Optionally the detector probe comprises a nucleic acid sequence of SEQ ID NO: 19.

There is also provided according to the invention a kit for determining whether a sample includes SARS-CoV-2 nucleic acid, which comprises:

a first forward nucleic acid amplification primer and a first reverse nucleic acid amplification primer; and a second forward nucleic acid amplification primer and a second reverse nucleic acid amplification primer;

wherein each nucleic acid amplification primer hybridises specifically to nucleic acid sequence that is conserved in SARS-CoV-2 nucleic acid, but not in other human coronavirus nucleic acid, or the complement thereof, and wherein the first forward nucleic acid amplification primer and the first reverse nucleic acid amplification primer hybridise specifically to nucleic acid sequence that is conserved in the ORF1ab gene of SARS-CoV-2 nucleic acid, or the complement thereof, and the second forward nucleic acid amplification primer and the second reverse nucleic acid amplification primer hybridise specifically to nucleic acid sequence that is conserved in the nucleocapsid gene of SARS-CoV-2 nucleic acid, or the complement thereof;

a first nucleic acid capture probe, and a second nucleic acid capture probe, wherein the first and second nucleic acid capture probe each hybridise specifically to nucleic acid sequence that is conserved in SARS-CoV-2 nucleic acid, but not in other human coronavirus

| Combination | Forward | Reverse | CP | DP |
|---|---|---|---|---|
| 1 | SEQ ID NO: 1 (nCoV-ARP1.1F) | SEQ ID NO: 5 (nCoV-ARP1.1R) | SEQ ID NO: 9 (nCoV-ARCP1.2) | SEQ ID NO: 12 (nCoV-ARDP1.2) |
| 2 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 11 (nCoV-ARDP1.1) |
| 3 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 12 (nCoV-ARDP1.2) |
| 4 | SEQ ID NO: 2 (nCoV-ARP1.2F) | SEQ ID NO: 5 (nCoV-ARP1.1R) | SEQ ID NO: 9 (nCoV-ARCP1.2) | SEQ ID NO: 12 (nCoV-ARDP1.2) |
| 5 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 11 (nCoV-ARDP1.1) |
| 6 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 12 (nCoV-ARDP1.2) |
| 7 | SEQ ID NO: 3 (nCoV-ARP1.3F) | SEQ ID NO: 5 (nCoV-ARP1.1R) | SEQ ID NO: 9 (nCoV-ARCP1.2) | SEQ ID NO: 12 (nCoV-ARDP1.2) |
| 8 | SEQ ID NO: 2 (nCoV-ARP1.2F) | SEQ ID NO: 6 (nCoV-ARP1.2R) | SEQ ID NO: 8 (nCoV-ARCP1.1) | SEQ ID NO: 11 (nCoV-ARDP1.1) |
| 9 | SEQ ID NO: 3 (nCoV-ARP1.3F) | SEQ ID NO: 6 (nCoV-ARP1.2R) | SEQ ID NO: 8 (nCoV-ARCP1.1) | SEQ ID NO: 11 (nCoV-ARDP1.1) |
| 10 | SEQ ID NO: 4 (SA_nCoV_F2) | SEQ ID NO: 7 (SA_nCoV_R2) | SEQ ID NO: 10 (SA_nCoV_CP2) | SEQ ID NO: 13 (SA_nCoV_DP2) |

Optionally the detector probe comprises a nucleic acid sequence of SEQ ID NO: 12.

Optionally the forward and reverse nucleic acid primers hybridise specifically to nucleic acid sequence that is conserved in the nucleocapsid gene of SARS-CoV-2, or the complement thereof, and the detector probe hybridizes specifically to nucleic acid sequence that is conserved in the nucleocapsid gene of SARS-CoV-2, or the complement thereof.

Optionally the detector probe comprises a nucleic acid sequence of: GAACCTAAATTGGGTAGTCTTGTAG (SEQ ID NO: 19), GGAACCTAAATTGGGTAGTCTTG (SEQ ID NO: 20), or a nucleic acid sequence that has at least 85%, 86%, 87%, 88%, 89%, 90%, 91%, 92%, 93%, 94%, nucleic acid, or the complement thereof, and wherein the first nucleic acid capture probe hybridises specifically to nucleic acid sequence that is conserved in the ORF1ab gene of SARS-CoV-2 nucleic acid, or the complement thereof, and the second nucleic acid capture probe hybridises specifically to nucleic acid sequence that is conserved in the nucleocapsid gene of SARS-CoV-2 nucleic acid, or the complement thereof; and/or a first nucleic acid detector probe, and a second nucleic acid detector probe, wherein the first and second nucleic acid detector probe each hybridise specifically to nucleic acid sequence that is conserved in SARS-CoV-2 nucleic acid, but not in other human coronavirus nucleic acid, or the complement thereof, and wherein the first nucleic acid detector probe hybridises specifically to nucleic acid sequence that is conserved in the ORF1ab gene of SARS-CoV-2 nucleic acid, or the complement thereof, and the second nucleic acid detector probe hybridises specifically to nucleic acid sequence that is conserved in the nucleocapsid gene of SARS-CoV-2 nucleic acid, or the complement thereof.

Optionally the first forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4.

Optionally the first reverse nucleic acid primer comprises a nucleic acid sequence: CAATAGTCTGAACAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7.

Optionally the first forward and reverse nucleic acid amplification primers comprise respective nucleic acid sequences according to any of the combinations of forward and reverse primer sequences shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |
| 6 | SEQ ID NO: 4 (SA_nCoV_F2) | SEQ ID NO: 7 (SA_nCoV_R2) |

Optionally the first forward nucleic acid amplification primer comprises a nucleic acid sequence of SEQ ID NO: 1, and the first reverse nucleic acid amplification primer comprises a nucleic acid sequence of SEQ ID NO: 5.

Optionally the second forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14.

Optionally the second reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17.

Optionally the second forward nucleic acid amplification primer comprises a nucleic acid sequence of SEQ ID NO: 14, and the second reverse nucleic acid amplification primer comprises a nucleic acid sequence of SEQ ID NO: 16.

Optionally the first and/or second reverse nucleic acid primer further comprises a promoter sequence for a DNA-dependent RNA polymerase at its 5'-end for reverse transcription of SARS-CoV-2 RNA using the reverse nucleic acid primer.

Optionally the first capture probe comprises a nucleic acid of sequence: GGCAGTGAGGACAATCAGCAACTAC (SEQ ID NO: 8), GAGGACAATCAGACAACTACTATTC (SEQ ID NO: 9), ACCCGTCCTTGATTGGCTTG (SEQ ID NO: 10), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 8, 9, or 10, or the complement thereof.

Optionally the first capture probe comprises a nucleic acid sequence of SEQ ID NO: 9.

Optionally the second capture probe comprises a nucleic acid of sequence: CTGGTTCTAAATCACCCATTCA (SEQ ID NO: 18), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 18, or the complement thereof.

Optionally the first detector probe comprises a nucleic acid sequence of: CAAACAATTGTTGAGGTTCAACCTC (SEQ ID NO: 11), GAGGTTCAACCTCAATTAGAGATGG (SEQ ID NO: 12), GGAAGGTGTAGAGTTTCTTAGAGAC (SEQ ID NO: 13), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, 12, or 13, or the complement thereof.

Optionally the first forward and reverse amplification primers, and the first capture and detector probes comprise respective nucleic acid sequences according to any of the combinations of forward and reverse primer sequences, and capture probe (CP) and detector probe (DP) shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse | CP | DP |
|---|---|---|---|---|
| 1 | SEQ ID NO: 1 (nCoV-ARP1.1F) | SEQ ID NO: 5 (nCoV-ARP1.1R) | SEQ ID NO: 9 (nCoV-ARCP1.2) | SEQ ID NO: 12 (nCoV-ARDP1.2) |
| 2 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 11 (nCoV-ARDP1.1) |
| 3 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 12 (nCoV-ARDP1.2) |

-continued

| Combination | Forward | Reverse | CP | DP |
|---|---|---|---|---|
| 4 | SEQ ID NO: 2 (nCoV-ARP1.2F) | SEQ ID NO: 5 (nCoV-ARP1.1R) | SEQ ID NO: 9 (nCoV-ARCP1.2) | SEQ ID NO: 12 (nCoV-ARDP1.2) |
| 5 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 11 (nCoV-ARDP1.1) |
| 6 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 12 (nCoV-ARDP1.2) |
| 7 | SEQ ID NO: 3 (nCoV-ARP1.3F) | SEQ ID NO: 5 (nCoV-ARP1.1R) | SEQ ID NO: 9 (nCoV-ARCP1.2) | SEQ ID NO: 12 (nCoV-ARDP1.2) |
| 8 | SEQ ID NO: 2 (nCoV-ARP1.2F) | SEQ ID NO: 6 (nCoV-ARP1.2R) | SEQ ID NO: 8 (nCoV-ARCP1.1) | SEQ ID NO: 11 (nCoV-ARDP1.1) |
| 9 | SEQ ID NO: 3 (nCoV-ARP1.3F) | SEQ ID NO: 6 (nCoV-ARP1.2R) | SEQ ID NO: 8 (nCoV-ARCP1.1) | SEQ ID NO: 11 (nCoV-ARDP1.1) |
| 10 | SEQ ID NO: 4 (SA_nCoV_F2) | SEQ ID NO: 7 (SA_nCoV_R2) | SEQ ID NO: 10 (SA_nCoV_CP2) | SEQ ID NO: 13 (SA_nCoV_DP2) |

Optionally the first detector probe comprises a nucleic acid sequence of SEQ ID NO: 12.

Optionally the second detector probe comprises a nucleic acid sequence of: GAACCTAAATTGGGTAGTCTTGTAG (SEQ ID NO: 19), GGAACCTAAATTGGGTAGTCTTG (SEQ ID NO: 20), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 19 or 20, or the complement thereof.

Optionally the second detector probe comprises a nucleic acid sequence of SEQ ID NO: 19.

Optionally a kit of the invention further comprises an RNA-dependent DNA polymerase, a DNA-dependent DNA polymerase, a DNA/RNA duplex-specific ribonuclease, and a DNA-dependent RNA polymerase.

Optionally a kit of the invention further comprises appropriate nucleotide triphosphates (for transcription-based amplifications ribonucleotide triphosphates (rNTPs, i.e. rATP, rGTP, rCTP, and rUTP), and deoxyribonucleotide triphosphates (dNTPs, i.e. dATP, dGTP, dCTP, and dTTP) are required), a suitable buffer for carrying out the amplification reaction, and any necessary cofactors (for example magnesium ions) required by the enzyme activities. Examples of suitable buffers include Tris-HCl, HEPES, or acetate buffer. A suitable salt may be provided, such as potassium chloride or sodium chloride. Suitable concentrations of these components may readily be determined by the skilled person. Suitable rNTP concentrations are typically in the range 0.25-5 mM, or 0.5-2.5 mM. Suitable dNTP concentrations are typically in the range 0.25-5 mM dNTP, or 0.5-2.5 mM. Suitable magnesium ion concentrations are typically in the range 5-15 mM.

A kit of the invention may further comprise a detectable label (for example, a visually detectable label) for labelling a product of the isothermal nucleic acid amplification and/or a chromatographic test strip and reagents for capturing and detecting a product of the isothermal nucleic acid amplification. Examples of suitable labels, test strips, and reagents, and methods for capturing and detecting a product of the isothermal nucleic acid amplification by a simple amplification-based assay (SAMBA), are described in WO 2008/090340 and Lee et al., Journal of Infectious Diseases 2010; 201 (S1): S65-S71. An amplification device for carrying out SAMBA methods, and apparatus for carrying out automated SAMBA methods, are described in WO 2014/140640.

For embodiments of a kit of the invention comprising a first forward and reverse nucleic acid primer, a second forward and reverse nucleic acid primer, a first and second nucleic acid capture probe and/or a first and second nucleic acid detector probe, the chromatographic test strip may comprise a first capture zone for capturing a product of the amplification reaction using the first forward and reverse nucleic acid amplification primers, and a second, separate capture zone for capturing a product of the amplification reaction using the second forward and reverse nucleic acid amplification primers.

SAMBA enables complex NAT to be carried out in doctor's offices, primary and community healthcare settings and small hospitals where complex NAT technology cannot be used. The technology can be instrumental in public health emergencies such as the current Corona virus outbreak. SAMBA POC testing augments testing capacity, alleviating delays due to sample transport and locating infected patients. SAMBA allows accurate NAT at POC settings in ~1 hour, thus enabling healthcare workers to rapidly and correctly identify, isolate and treat patients infectious for SARS-CoV-2—keys to limiting the present outbreak. SAMBA will give more hospitals capability for SARS-CoV-2 RNA testing, allowing infected patients to be identified and treated without waiting for results from a centralized testing laboratory.

A kit of the invention may further comprise reagents for isolating nucleic acid from a sample, for example using a method of nucleic acid extraction as described above. Suitable reagents for extracting nucleic acid may include a lysis buffer for lysing cells present in the sample, a solid phase for binding nucleic acid, a binding buffer for binding nucleic acid to the solid phase (optionally, the lysis buffer is the same as the binding buffer) optionally a wash buffer for washing nucleic acid bound to the solid phase, and an elution buffer for eluting nucleic acid from the solid phase. Suitable lysis, wash, and elution buffers are described above, as well as suitable solid phases for use with the buffers.

Optionally a kit of the invention further comprises a lysis/binding buffer, an elution buffer, and optionally a wash buffer, for extracting nucleic acid from a biological sample obtained from the subject.

A kit of the invention may further comprise a swab stick for obtaining a nasopharyngeal or throat swab sample from a subject.

Optionally a kit of the invention comprises a first swab stick for obtaining a nasopharyngeal swab sample from a subject, and a second swab stick for obtaining a throat swab sample from a subject.

Suitable swab sticks are commercially available: Copan Diagnostics Nylon Flocked Dry Swabs in Peel Pouches (Copan Diagnostics 503CS01).

Optionally a kit of the invention further comprises a chromatographic test strip for capturing and detecting a product of the isothermal nucleic acid amplification.

Optionally a kit of the invention further comprises positive and/or negative controls.

Optionally a kit of the invention further comprises instructions for carrying out a method of the invention using the kit.

According to the invention there is also provided a set of primers for amplifying SARS-CoV-2 nucleic acid by an isothermal nucleic acid amplification reaction, which comprises a forward nucleic acid amplification primer and a reverse nucleic acid amplification primer, wherein each nucleic acid amplification primer hybridises specifically to nucleic acid sequence that is conserved in SARS-CoV-2 nucleic acid, but not in other human coronavirus nucleic acid, or the complement thereof.

Optionally the other human coronavirus nucleic acid is human coronavirus 229E, SARS, HKU1, MERS, OC43, and NL63 nucleic acid.

The forward and reverse nucleic acid amplification primers of a set of primers of the invention may be any of the forward and reverse nucleic acid amplification primers, or any of the combinations of primers as recited herein for methods of the invention.

Optionally the nucleic acid sequence that is conserved in SARS-CoV-2 nucleic acid, but not in other human coronavirus nucleic acid, comprises a contiguous nucleic acid sequence that is at least 19 nucleotides long.

Optionally the nucleic acid sequence that is conserved in SARS-CoV-2 nucleic acid is nucleic acid sequence that is conserved in the ORF1ab gene or the Nucleocapsid gene of SARS-CoV-2, or the complement thereof.

Optionally the forward nucleic acid primer hybridizes specifically to nucleic acid sequence that is conserved in the ORF1ab gene of SARS-CoV-2, or the complement thereof.

Optionally the forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4.

Optionally the reverse nucleic acid primer hybridizes specifically to nucleic acid sequence that is conserved in the ORF1ab gene of SARS-CoV-2, or the complement thereof.

Optionally the reverse nucleic acid primer comprises a nucleic acid sequence: CAATAGTCTGAACAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7.

Optionally the forward and reverse nucleic acid amplification primers comprise respective nucleic acid sequences according to any of the combinations of forward and reverse primer sequences shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |
| 6 | SEQ ID NO: 4 (SA_nCoV_F2) | SEQ ID NO: 7 (SA_nCoV_R2) |

Optionally the forward nucleic acid amplification primer comprises a nucleic acid sequence of SEQ ID NO: 1, and the reverse nucleic acid amplification primer comprises a nucleic acid sequence of SEQ ID NO: 5.

Optionally the forward nucleic acid primer hybridizes specifically to nucleic acid sequence that is conserved in the nucleocapsid gene of SARS-CoV-2, or the complement thereof.

Optionally the forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14.

Optionally the reverse nucleic acid primer hybridizes specifically to nucleic acid sequence that is conserved in the nucleocapsid gene of SARS-CoV-2, or the complement thereof.

Optionally the reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17.

Optionally the forward nucleic acid amplification primer comprises a nucleic acid sequence of SEQ ID NO: 14, and the reverse nucleic acid amplification primer comprises a nucleic acid sequence of SEQ ID NO: 16.

Optionally the reverse nucleic acid primer further comprises a promoter sequence for a DNA-dependent RNA polymerase at its 5'-end.

Optionally the forward and/or the reverse nucleic acid primer is up to 50 nucleotides long.

There is also provided according to the invention a set of primers for amplifying SARS-CoV-2 nucleic acid by an isothermal nucleic acid amplification reaction, which comprises:

- a first forward nucleic acid amplification primer and a first reverse nucleic acid amplification primer; and
- a second forward nucleic acid amplification primer and a second reverse nucleic acid amplification primer;
- wherein each nucleic acid amplification primer hybridises specifically to nucleic acid sequence that is conserved in SARS-CoV-2 nucleic acid, but not in other human coronavirus nucleic acid, or the complement thereof, and wherein the first forward nucleic acid amplification primer and the first reverse nucleic acid amplification primer hybridise specifically to nucleic acid sequence that is conserved in the ORF1ab gene of SARS-CoV-2 nucleic acid, or the complement thereof, and the second forward nucleic acid amplification primer and the second reverse nucleic acid amplification primer hybridise specifically to nucleic acid sequence that is conserved in the nucleocapsid gene of SARS-CoV-2 nucleic acid, or the complement thereof.

Optionally the first forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4.

Optionally the first reverse nucleic acid primer comprises a nucleic acid sequence: CAATAGTCTGAAGAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7.

Optionally the first forward and reverse nucleic acid amplification primers comprise respective nucleic acid sequences according to any of the combinations of forward and reverse primer sequences shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |
| 6 | SEQ ID NO: 4 (SA_nCoV_F2) | SEQ ID NO: 7 (SA_nCoV_R2) |

Optionally the first forward nucleic acid amplification primer comprises a nucleic acid sequence of SEQ ID NO: 1, and the first reverse nucleic acid amplification primer comprises a nucleic acid sequence of SEQ ID NO: 5.

Optionally the second forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14.

Optionally the second reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17.

Optionally the second forward nucleic acid amplification primer comprises a nucleic acid sequence of SEQ ID NO: 14, and the second reverse nucleic acid amplification primer comprises a nucleic acid sequence of SEQ ID NO: 16.

Optionally the first and/or second reverse nucleic acid primer further comprises a promoter sequence for a DNA-dependent RNA polymerase at its 5'-end for reverse transcription of SARS-CoV-2 RNA using the reverse nucleic acid primer.

There is also provided according to the invention a set of oligonucleotides for amplifying SARS-CoV-2 nucleic acid by an isothermal nucleic acid amplification reaction, and for capturing and/or detecting a product of the amplification reaction, which comprises:

a set of primers of the invention;

a nucleic acid capture probe, wherein the capture probe hybridises specifically to nucleic acid sequence that is conserved in SARS-CoV-2 nucleic acid, but not in other human coronavirus nucleic acid, or the complement thereof; and/or a nucleic acid detector probe, wherein the detector probe hybridises specifically to nucleic acid sequence that is conserved in SARS-CoV-2 nucleic acid, but not in other human coronavirus nucleic acid, or the complement thereof, optionally wherein the detector probe comprises a detectable label for labelling a product of the isothermal nucleic acid amplification.

Optionally the other human coronavirus nucleic acid is human coronavirus 229E, SARS, HKU1, MERS, OC43, and NL63 nucleic acid.

The forward and reverse nucleic acid amplification primers, or the capture and/or detector probes, of a set of oligonucleotides of the invention may be any of the forward and reverse nucleic acid amplification primers, or any of the capture and/or detector probes, or any of the combinations of primers and/or probes as recited herein for methods of the invention.

Optionally the nucleic acid sequence that is conserved in SARS-CoV-2 nucleic acid, but not in other human coronavirus nucleic acid, comprises a contiguous nucleic acid sequence that is at least 19 nucleotides long.

Optionally the forward nucleic acid primer hybridizes specifically to nucleic acid sequence that is conserved in the ORF1ab gene of SARS-CoV-2, or the complement thereof.

Optionally the forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4.

Optionally the reverse nucleic acid primer hybridizes specifically to nucleic acid sequence that is conserved in the ORF1ab gene of SARS-CoV-2, or the complement thereof.

Optionally the reverse nucleic acid primer comprises a nucleic acid sequence: CAATAGTCTGAACAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7.

Optionally the forward and reverse nucleic acid amplification primers comprise respective nucleic acid sequences according to any of the combinations of forward and reverse primer sequences shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |
| 6 | SEQ ID NO: 4 (SA_nCoV_F2) | SEQ ID NO: 7 (SA_nCoV_R2) |

Optionally the forward nucleic acid amplification primer comprises a nucleic acid sequence of SEQ ID NO: 1, and the reverse nucleic acid amplification primer comprises a nucleic acid sequence of SEQ ID NO: 5.

Optionally the forward nucleic acid primer hybridizes specifically to nucleic acid sequence that is conserved in the nucleocapsid gene of SARS-CoV-2, or the complement thereof.

Optionally the forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14.

Optionally the reverse nucleic acid primer hybridizes specifically to nucleic acid sequence that is conserved in the nucleocapsid gene of SARS-CoV-2, or the complement thereof.

Optionally the reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17.

Optionally the forward nucleic acid amplification primer comprises a nucleic acid sequence of SEQ ID NO: 14, and the reverse nucleic acid amplification primer comprises a nucleic acid sequence of SEQ ID NO: 16.

Optionally the reverse nucleic acid primer further comprises a promoter sequence for a DNA-dependent RNA polymerase at its 5'-end for reverse transcription of SARS-CoV-2 RNA using the reverse nucleic acid primer.

Optionally the forward and reverse nucleic acid primers hybridise specifically to nucleic acid sequence that is conserved in the ORF1ab gene of SARS-CoV-2, or the complement thereof, and the capture probe hybridizes specifically to nucleic acid sequence that is conserved in the ORF1ab gene of SARS-CoV-2, or the complement thereof.

Optionally the capture comprises a nucleic acid of sequence: ID GGCAGTGAGGACAATCAGCAACTAC (SEQ NO: 8), GAGGACAATCAGACAACTACTATTC (SEQ ID NO: 9), ACCCGTCCTTGATTGGCTTG (SEQ ID NO: 10), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 8, 9, or 10, or the complement thereof.

Optionally the capture probe comprises a nucleic acid sequence of SEQ ID NO: 9.

Optionally the forward and reverse nucleic acid primers hybridise specifically to nucleic acid sequence that is conserved in the nucleocapsid gene of SARS-CoV-2, or the complement thereof, and the capture probe hybridizes specifically to nucleic acid sequence that is conserved in the nucleocapsid gene of SARS-CoV-2, or the complement thereof.

Optionally the capture probe comprises a nucleic acid of sequence: CTGGTTCTAAATCACCCATTCA (SEQ ID NO: 18), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 18, or the complement thereof.

Optionally the forward and reverse nucleic acid primers hybridise specifically to nucleic acid sequence that is conserved in the ORF1ab gene of SARS-CoV-2, or the complement thereof, and the detector probe hybridizes specifically to nucleic acid sequence that is conserved in the ORF1ab gene of SARS-CoV-2, or the complement thereof.

Optionally the detector probe comprises a nucleic acid sequence of: CAAACAATTGTTGAGGTTCAACCTC (SEQ ID NO: 11), GAGGTTCAACCTCAATT-AGAGATGG (SEQ ID NO: 12), GGAAGGTGTAGAGTTTCTTAGAGAC (SEQ ID NO: 13), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, 12, or 13, or the complement thereof.

Optionally a set of oligonucleotides of the invention comprises forward and reverse amplification primers, and capture and detector probes comprising respective nucleic acid sequences according to any of the combinations of forward and reverse primer sequences, and capture probe (CP) and detector probe (DP) shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse | CP | DP |
|---|---|---|---|---|
| 1 | SEQ ID NO: 1 (nCoV-ARP1.1F) | SEQ ID NO: 5 (nCoV-ARP1.1R) | SEQ ID NO: 9 (nCoV-ARCP1.2) | SEQ ID NO: 12 (nCoV-ARDP1.2) |
| 2 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 11 (nCoV-ARDP1.1) |
| 3 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 12 (nCoV-ARDP1.2) |
| 4 | SEQ ID NO: 2 (nCoV-ARP1.2F) | SEQ ID NO: 5 (nCoV-ARP1.1R) | SEQ ID NO: 9 (nCoV-ARCP1.2) | SEQ ID NO: 12 (nCoV-ARDP1.2) |
| 5 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 11 (nCoV-ARDP1.1) |

-continued

| Combination | Forward | Reverse | CP | DP |
|---|---|---|---|---|
| 6 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 12 (nCoV-ARDP1.2) |
| 7 | SEQ ID NO: 3 (nCoV-ARP1.3F) | SEQ ID NO: 5 (nCoV-ARP1.1R) | SEQ ID NO: 9 (nCoV-ARCP1.2) | SEQ ID NO: 12 (nCoV-ARDP1.2) |
| 8 | SEQ ID NO: 2 (nCoV-ARP1.2F) | SEQ ID NO: 6 (nCoV-ARP1.2R) | SEQ ID NO: 8 (nCoV-ARCP1.1) | SEQ ID NO: 11 (nCoV-ARDP1.1) |
| 9 | SEQ ID NO: 3 (nCoV-ARP1.3F) | SEQ ID NO: 6 (nCoV-ARP1.2R) | SEQ ID NO: 8 (nCoV-ARCP1.1) | SEQ ID NO: 11 (nCoV-ARDP1.1) |
| 10 | SEQ ID NO: 4 (SA_nCoV_F2) | SEQ ID NO: 7 (SA_nCoV_R2) | SEQ ID NO: 10 (SA_nCoV_CP2) | SEQ ID NO: 13 (SA_nCoV_DP2) |

Optionally the detector probe comprises a nucleic acid sequence of SEQ ID NO: 12.

Optionally the forward and reverse nucleic acid primers hybridise specifically to nucleic acid sequence that is conserved in the nucleocapsid gene of SARS-CoV-2, or the complement thereof, and the detector probe hybridizes specifically to nucleic acid sequence that is conserved in the nucleocapsid gene of SARS-CoV-2, or the complement thereof.

Optionally the detector comprises a nucleic acid sequence of: GAACCTAAATTGGGTAGTCTTGTAG (SEQ ID NO: 19), GGAACCTAAATTGGGTAGTCTTG (SEQ ID NO: 20), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 19 or 20, or the complement thereof.

Optionally the detector probe comprises a nucleic acid sequence of SEQ ID NO: 19.

Optionally the capture and/or detector probe is up to 20, 25, 30, 35, 40, 45, 50, 55, or 60 nucleotides long.

There is also provided according to the invention a set of oligonucleotides for amplifying SARS-CoV-2 nucleic acid by an isothermal nucleic acid amplification reaction, and for capturing and/or detecting a product of the amplification reaction, which comprises:

- a first forward nucleic acid amplification primer and a first reverse nucleic acid amplification primer; and
- a second forward nucleic acid amplification primer and a second reverse nucleic acid amplification primer;

wherein each nucleic acid amplification primer hybridises specifically to nucleic acid sequence that is conserved in SARS-CoV-2 nucleic acid, but not in other human coronavirus nucleic acid, or the complement thereof, and wherein the first forward nucleic acid amplification primer and the first reverse nucleic acid amplification primer hybridise specifically to nucleic acid sequence that is conserved in the ORF1ab gene of SARS-CoV-2 nucleic acid, or the complement thereof, and the second forward nucleic acid amplification primer and the second reverse nucleic acid amplification primer hybridise specifically to nucleic acid sequence that is conserved in the nucleocapsid gene of SARS-CoV-2 nucleic acid, or the complement thereof;

- a first nucleic acid capture probe, and a second nucleic acid capture probe, wherein the first and second nucleic acid capture probe each hybridise specifically to nucleic acid sequence that is conserved in SARS-CoV-2 nucleic acid, but not in other human coronavirus nucleic acid, or the complement thereof, and wherein the first nucleic acid capture probe hybridises specifically to nucleic acid sequence that is conserved in the ORF1ab gene of SARS-CoV-2 nucleic acid, or the complement thereof, and the second nucleic acid capture probe hybridises specifically to nucleic acid sequence that is conserved in the nucleocapsid gene of SARS-CoV-2 nucleic acid, or the complement thereof; and/or
- a first nucleic acid detector probe, and a second nucleic acid detector probe, wherein the first and second nucleic acid detector probe each hybridise specifically to nucleic acid sequence that is conserved in SARS-CoV-2 nucleic acid, but not in other human coronavirus nucleic acid, or the complement thereof, and wherein the first nucleic acid detector probe hybridises specifically to nucleic acid sequence that is conserved in the ORF1ab gene of SARS-CoV-2 nucleic acid, or the complement thereof, and the second nucleic acid detector probe hybridises specifically to nucleic acid sequence that is conserved in the nucleocapsid gene of SARS-CoV-2 nucleic acid, or the complement thereof.

Optionally the first forward nucleic acid primer comprises a nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, 2, 3, or 4.

Optionally the first reverse nucleic acid primer comprises a nucleic acid sequence: CAATAGTCTGAACAACTGGTGT (SEQ ID NO: 5), CTGGTGTAAGTTCCATCTCT (SEQ ID NO: 6), AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, 6, or 7.

Optionally the first forward and reverse nucleic acid amplification primers comprise respective nucleic acid sequences according to any of the combinations of forward and reverse primer sequences shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse |
|---|---|---|
| 1 | SEQ ID NO: 1 (nCoV-ARP1.1F) | SEQ ID NO: 5 (nCoV-ARP1.1R) |
| 2 | SEQ ID NO: 2 (nCoV-ARP1.2F) | SEQ ID NO: 5 (nCoV-ARP1.1R) |

-continued

| Combination | Forward | Reverse |
|---|---|---|
| 3 | SEQ ID NO: 3 (nCoV-ARP1.3F) | SEQ ID NO: 5 (nCoV-ARP1.1R) |
| 4 | SEQ ID NO: 2 (nCoV-ARP1.2F) | SEQ ID NO: 6 (nCoV-ARP1.2R) |
| 5 | SEQ ID NO: 3 (nCoV-ARP1.3F) | SEQ ID NO: 6 (nCoV-ARP1.2R) |
| 6 | SEQ ID NO: 4 (SA_nCoV_F2) | SEQ ID NO: 7 (SA_nCoV_R2) |

Optionally the first forward nucleic acid amplification primer comprises a nucleic acid sequence of SEQ ID NO: 1, and the first reverse nucleic acid amplification primer comprises a nucleic acid sequence of SEQ ID NO: 5.

Optionally the second forward nucleic acid primer comprises a nucleic acid sequence of: TAGTTGATGACCCGTGTCCT (SEQ ID NO: 14) or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14.

Optionally the second reverse nucleic acid primer comprises a nucleic acid sequence: TGGGGTCCATTATCAGACAT (SEQ ID NO: 15), CAACACGAACGTCATGATAC (SEQ ID NO: 16), CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, 16, or 17.

Optionally the second forward nucleic acid amplification primer comprises a nucleic acid sequence of SEQ ID NO: 14, and the second reverse nucleic acid amplification primer comprises a nucleic acid sequence of SEQ ID NO: 16.

96%, 97%, 98%, or 99% identity along its entire length with a nucleic acid sequence of SEQ ID NO: 8, 9, or 10, or the complement thereof.

Optionally the first capture probe comprises a nucleic acid sequence of SEQ ID NO: 9.

Optionally the second capture probe comprises a nucleic acid of sequence: CTGGTTCTAAATCACCCATTCA (SEQ ID NO: 18), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 18, or the complement thereof.

Optionally the first detector probe comprises a nucleic acid sequence of: CAAACAATTGTTGAGGTTCAACCTC ID (SEQ NO: 11), GAGGTTCAACCTCAATTAGAGATGG (SEQ ID NO: 12), GGAAGGTGTAGAGTTTCTTAGAGAC (SEQ ID NO: 13), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, 12, or 13, or the complement thereof.

Optionally the first forward and reverse amplification primers, and the first capture and detector probes comprise respective nucleic acid sequences according to any of the combinations of forward and reverse primer sequences, and capture probe (CP) and detector probe (DP) shown in the table below, or nucleic acid sequences which have at least 85%, 86%, 87%, 88%, 89%, 90%, 91%, 92%, 93%, 94%, 95%, 96%, 97%, 98%, or 99% identity along their entire length with such sequences:

| Combination | Forward | Reverse | CP | DP |
|---|---|---|---|---|
| 1 | SEQ ID NO: 1 (nCoV-ARP1.1F) | SEQ ID NO: 5 (nCoV-ARP1.1R) | SEQ ID NO: 9 (nCoV-ARCP1.2) | SEQ ID NO: 12 (nCoV-ARDP1.2) |
| 2 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 11 (nCoV-ARDP1.1) |
| 3 | SEQ ID NO: 2 (nCoV-ARP1.2F) | SEQ ID NO: 5 (nCoV-ARP1.1R) | SEQ ID NO: 8 (nCoV-ARCP1.1) | SEQ ID NO: 12 (nCoV-ARDP1.2) |
| 4 | SEQ ID NO: 2 (nCoV-ARP1.2F) | SEQ ID NO: 5 (nCoV-ARP1.1R) | SEQ ID NO: 9 (nCoV-ARCP1.2) | SEQ ID NO: 12 (nCoV-ARDP1.2) |
| 5 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 11 (nCoV-ARDP1.1) |
| 6 | SEQ ID NO: 3 (nCoV-ARP1.3F) | SEQ ID NO: 5 (nCoV-ARP1.1R) | SEQ ID NO: 8 (nCoV-ARCP1.1) | SEQ ID NO: 12 (nCoV-ARDP1.2) |
| 7 | SEQ ID NO: 3 (nCoV-ARP1.3F) | SEQ ID NO: 5 (nCoV-ARP1.1R) | SEQ ID NO: 9 (nCoV-ARCP1.2) | SEQ ID NO: 12 (nCoV-ARDP1.2) |
| 8 | SEQ ID NO: 2 (nCoV-ARP1.2F) | SEQ ID NO: 6 (nCoV-ARP1.2R) | SEQ ID NO: 8 (nCoV-ARCP1.1) | SEQ ID NO: 11 (nCoV-ARDP1.1) |
| 9 | SEQ ID NO: 3 (nCoV-ARP1.3F) | SEQ ID NO: 6 (nCoV-ARP1.2R) | SEQ ID NO: 8 (nCoV-ARCP1.1) | SEQ ID NO: 11 (nCoV-ARDP1.1) |
| 10 | SEQ ID NO: 4 (SA_nCoV_F2) | SEQ ID NO: 7 (SA_nCoV_R2) | SEQ ID NO: 10 (SA_nCoV_CP2) | SEQ ID NO: 13 (SA_nCoV_DP2) |

Optionally the first and/or second reverse nucleic acid primer further comprises a promoter sequence for a DNA-dependent RNA polymerase at its 5'-end for reverse transcription of SARS-CoV-2 RNA using the reverse nucleic acid primer.

Optionally the first capture probe comprises a nucleic acid of sequence: GGCAGTGAGGACAATCAGCAACTAC (SEQ ID NO: 8), GAGGACAATCAGACAACTACTATTC (SEQ ID NO: 9), ACCCGTCCTTGATTGGCTTG (SEQ ID NO: 10), or a nucleic acid sequence that has at least 85%, 86%, 87%, 88%, 89%, 90%, 91%, 92%, 93%, 94%, 95%, Optionally the first detector probe comprises a nucleic acid sequence of SEQ ID NO: 12.

Optionally the second detector probe comprises a nucleic acid sequence of: GAACCTAAATTGGGTAGTCTTGTAG (SEQ ID NO: 19), GGAACCTAAATTGGGTAGTCTTG (SEQ ID NO: 20), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 19 or 20, or the complement thereof.

Optionally the second detector probe comprises a nucleic acid sequence of SEQ ID NO: 19.

There is also provided according to the invention an oligonucleotide, which comprises:

a nucleic acid sequence of: CTGTTGGTCAACAAGACGGCA (SEQ ID NO: 1), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 1, or the complement thereof;

a nucleic acid sequence of: GTCAACAAACTGTTGGTCAA (SEQ ID NO: 2), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 2, or the complement thereof;

a nucleic acid sequence of: GTCAACAAACTGTTGGTCAACA (SEQ ID NO: 3), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 3, or the complement thereof;

a nucleic acid sequence of: CATTACAGGTGGTGTTGTTCAGTT (SEQ ID NO: 4), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 4, or the complement thereof;

a nucleic acid sequence of: CAATAGTCTGAACAACTGGTGT (SEQ ID NO: 5), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 5, or the complement thereof;

a nucleic acid sequence of: CTGGTGTAAGTTCCATCTCT (SEQ ID NO: 6), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 6, or the complement thereof;

a nucleic acid sequence of: AGGTGACAATTTGTCCACCGAC (SEQ ID NO: 7), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 7, or the complement thereof;

a nucleic acid sequence of: GGCAGTGAGGACAATCAGCAACTAC (SEQ ID NO: 8), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 8, or the complement thereof;

a nucleic acid sequence of: GAGGACAATCAGACAACTACTATTC (SEQ ID NO: 9), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 9, or the complement thereof;

a nucleic acid sequence of: ACCCGTCCTTGATTGGCTTG (SEQ ID NO: 10), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 10, or the complement thereof;

a nucleic acid sequence of: CAAACAATTGTTGAGGTTCAACCTC (SEQ ID NO: 11), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, or the complement thereof;

a nucleic acid sequence of: GAGGTTCAACCTCAATTAGAGATGG (SEQ ID NO: 12), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 12, or the complement thereof;

a nucleic acid sequence of: GGAAGGTGTAGAGTTTCTTAGAGAC (SEQ ID NO: 13), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 13, or the complement thereof;

a nucleic acid sequence of: TAGTTGATGACCCGTGTCCT (SEQ ID NO: 14), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 14, or the complement thereof;

a nucleic acid sequence of: TGGGGTCCATTATCAGACAT (SEQ ID NO: 15), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 15, or the complement thereof;

a nucleic acid sequence of: CAACACGAACGTCATGATAC (SEQ ID NO: 16), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 16, or the complement thereof;

a nucleic acid sequence of: CATAGAACGAACAACGCAC (SEQ ID NO: 17), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 17, or the complement thereof;

a nucleic acid sequence of: CTGGTTCTAAATCACCCATTCA (SEQ ID NO: 18), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 18, or the complement thereof;

a nucleic acid sequence of: GAACCTAAATTGGGTAGTCTTGTAG (SEQ ID NO: 19), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 19, or the complement thereof; or a nucleic acid sequence of: GGAACCTAAATTGGGTAGTCTTG (SEQ ID NO: 20), or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 20, or the complement thereof.

A set of primers, a set of oligonucleotides, or an oligonucleotide, of the invention may be used in a kit of the invention, or in a method of the invention.

A primer, probe, or oligonucleotide of the invention, or of a set of primers or oligonucleotides of the invention, or of a kit of the invention, or for use in a method of the invention, may be at least 15, 20, 25, 30, 35, 40, 45, 50, or over 50 nucleotides in length.

A primer, probe, or oligonucleotide of the invention, or of a set of primers or oligonucleotides of the invention, or of a kit of the invention, or for use in a method of the invention, may be up to 20, 25, 30, 35, 40, 45, 50, 55, 60, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 1 may be up to 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 1 may be up to 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 2 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 2 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 3 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 3 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 4 may be up to 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 4 may be up to 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 5 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 5 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 6 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 6 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 7 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 7 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 8 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 8 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 9 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 9 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 10 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 10 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 11 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 11 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 12 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 12 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 13 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 13 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 14 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 14 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 15 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 15 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 16 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 16 may be up to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 17 may be up to 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 17 may be up to 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 18 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 18 may be up to 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 19 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 19 may be up to 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

A primer or oligonucleotide of the invention, or of a set of primers or oligonucleotides of the invention, or of a kit of the invention, or for use in a method of the invention, which comprises a nucleic acid sequence of SEQ ID NO: 20 may be up to 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention, or of a set of primers or oligonucleotides of the invention, or of a kit of the invention, or for use in a method of the invention, which comprises the complement of a nucleic acid sequence of SEQ ID NO: 20 may be up to 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 nucleotides in length.

An oligonucleotide of the invention may comprise a nucleotide sequence that comprises or consists of a sequence that is at least 85%, 86%, 87%, 88%, 89%, 90%, 91%, 92%, 93%, 94%, 95%, 96%, 97%, 98%, or 99% identical, or that is 100% identical, over its entire length to the nucleotide sequence of any of SEQ ID NOs: 1-20, or the complement thereof.

The oligonucleotide may be labelled with a detectable label, for example with a visually detectable label. In particular, an oligonucleotide that comprises or consists of a nucleic acid sequence of SEQ ID NO: 11, 12, 13, 19, or 20, or a nucleic acid sequence that has at least 85%, 86%, 87%, 88%, 89%, 90%, 91%, 92%, 93%, 94%, 95%, 96%, 97%, 98%, or 99% identity along its entire length with a nucleic acid sequence of SEQ ID NO: 11, 12, 13, 19, or 20, or the complement thereof, may be labelled with a visually detectable label. Examples of visually detectable labels include colloidal metal sol particles, latex particles, or textile dye particles. An example of colloidal metal sol particles is colloidal gold particles.

A set of primers or oligonucleotides of the invention may comprise an oligonucleotide of the invention.

A kit of the invention may comprise a set of primers, a set of oligonucleotides, or an oligonucleotide, of the invention.

There is also provided according to the invention use of a set of primers, a set of oligonucleotides, or an oligonucleotide, of the invention in a method of the invention.

Figure 4:
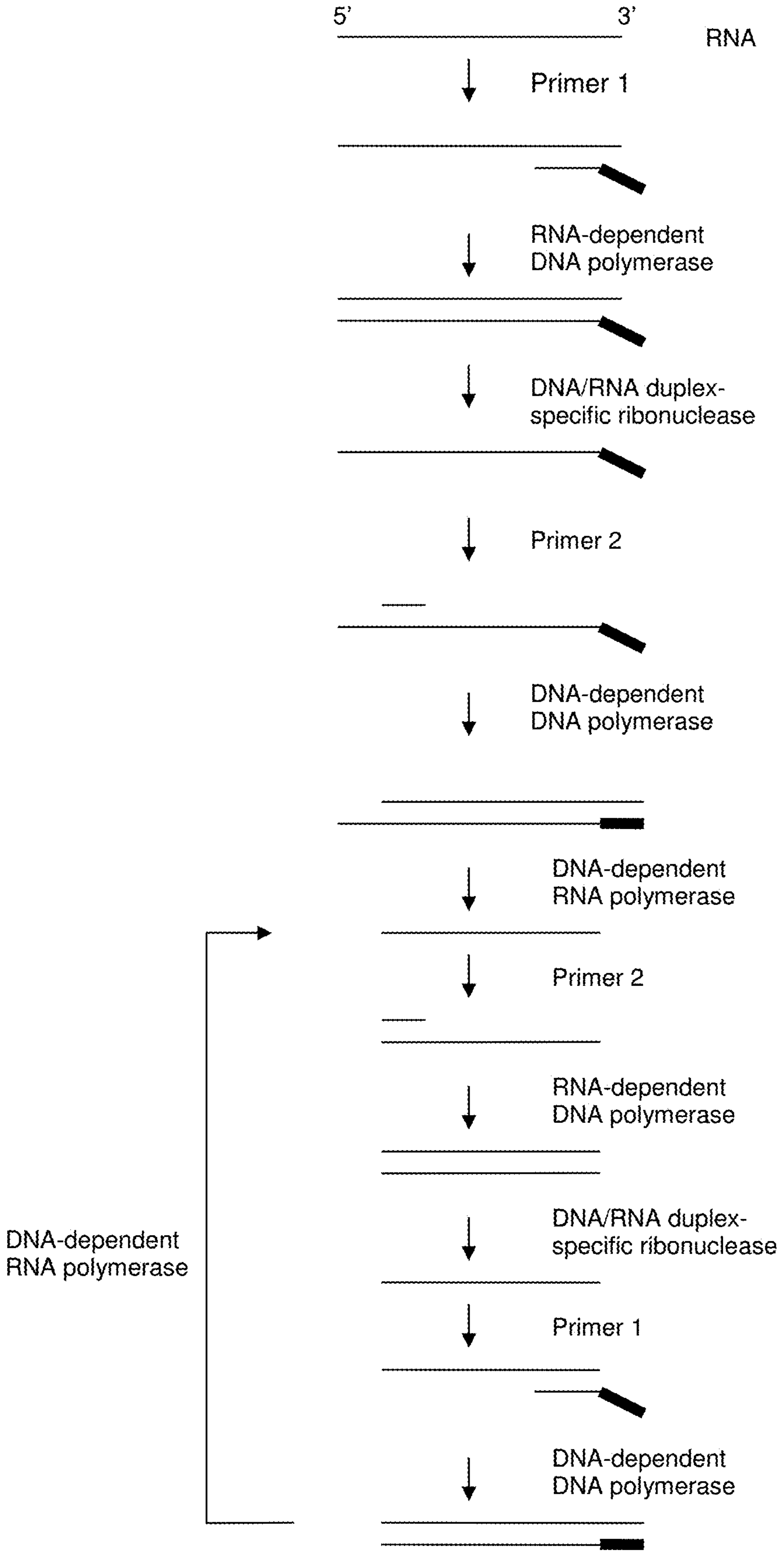
Figure 5:
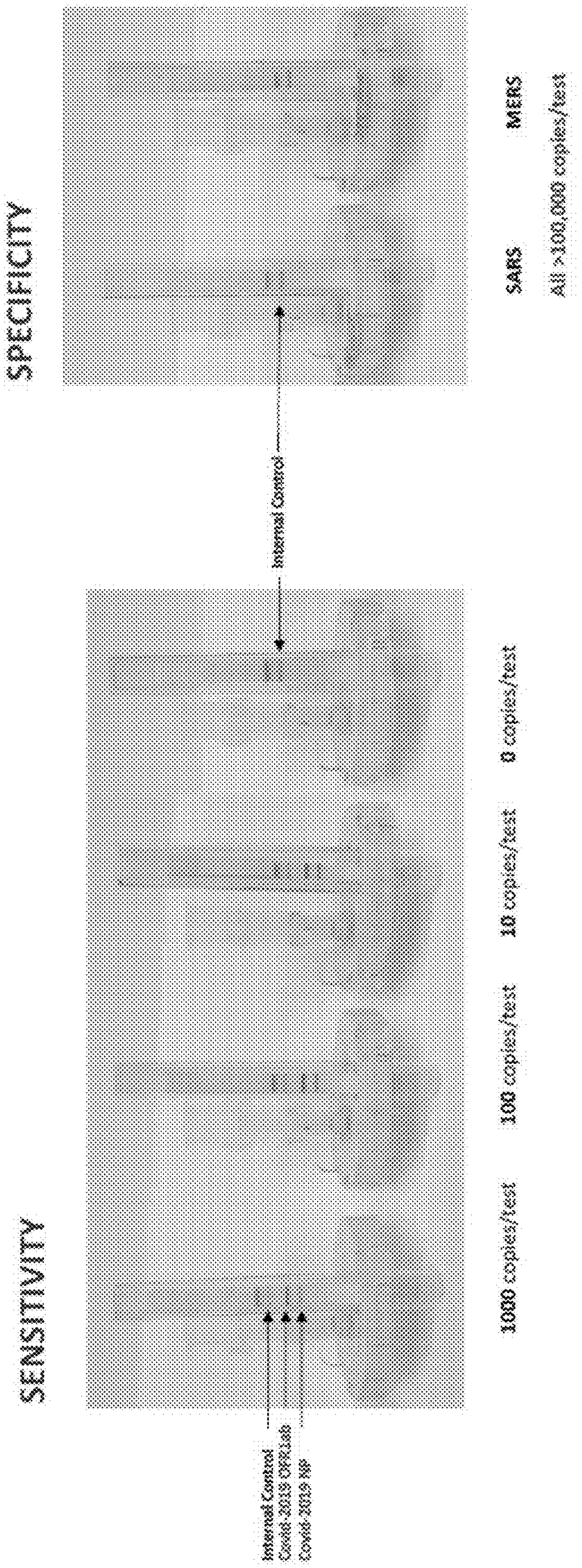

Embodiments of the invention are described below, by way of example only, with reference to the accompanying drawings in which:

FIG. 1 shows the genome organisation of SARS-CoV-2 (isolate Wuhan-Hu-1, GenBank Acc MN908947);

FIG. 2A-D shows a multiple sequence alignment of the ORF1ab region for all 7 human coronaviruses (229E, SARS, HKU1, MERS, OC43, and NL63, and SARS-CoV-2 sequences of several different isolates), and a bat SARS-like coronavirus sequence. In the figure, SARS-CoV-2 is referred to by its previous provisional name "2019-nCOV" (2019 novel coronavirus). The locations in the SARS-CoV-2 ORF1ab gene sequence corresponding to the sequence of the forward primers of SEQ ID NOs: 1-3 (2019-nCoV-ARP1.1F, 2019-nCoV-ARP1.2F, 2019-nCoV-ARP1.3F, respectively), and to the reverse complement of sequence of the reverse primers of SEQ ID NOs: 5,6 (2019-nCoV-ARP1.1R, 2019-nCoV-ARP1.2R, respectively), are also shown;

FIG. 3A-I shows a multiple sequence alignment of the nucleocapsid region for all 7 human coronaviruses (229E, SARS, HKU1, MERS, OC43, and NL63, and SARS-CoV-2 sequences of several different isolates), and a bat SARS-like coronavirus sequence. In the figure, SARS-CoV-2 is referred to by its previous provisional name "2019-nCOV" (2019 novel coronavirus). The locations in the SARS-CoV-2 nucleocapsid gene sequence corresponding to the sequence of the forward primer of SEQ ID NO: 14 (SA-nCoV-F2.3), and to the reverse complement of sequence of the reverse primers of SEQ ID NOs: 15-17 (SA-nCoV-R2.3, SA-nCoV-R2.4, SA-nCoV-R2.5, respectively), are also shown;

FIG. 4 shows schematically the steps for transcription-based amplification of a target RNA; and FIG. 5 shows the results of a Point-of-care (POC) nucleic acid test for detecting SARS-CoV-2 using a method according to an embodiment of the invention.

EXAMPLE 1

Design of Primers and Probes from Coronavirus Orf1Ab Sequence Alignments

Nucleic acid sequences of the Orf1ab gene for all seven human coronaviruses (229E, SARS, HKU1, MERS, OC43, NL63, and SARS-CoV-2) were obtained, including three different SARS-CoV-2 sequences, and a bat SARS-like coronavirus sequence. These sequences were aligned using the CLUSTAL 0 (1.2.4) multiple sequence alignment software. The multiple sequence alignment is shown in FIG. 2. In FIG. 2, SARS-CoV-2 is referred to by its previous provisional name, 2019-nCOV (2019 novel coronavirus).

The sequences obtained are shown below:

```
MERS CoV KJ477103.2
                                        (SEQ ID NO: 27)
AGGAGTGTTCTGAAGTAGAGGCTTCAGATTTAGAAGAAGGTGAATCAG

AGTGCATTTCTGAGACTTCAACTGAACAAGTTGACGTTTCTCATGAGA

CTTCT

hCoV OC43 KU131570
                                        (SEQ ID NO: 28)
ATGATGGTCCAAGTGTGGAGACATCTGATTCACAAGTTGAAGAAGATG
```

-continued

TAGAAATGTCGGATTTTGTTGATCTTGAATCTGTGATTCAGGATTATG

AAAATGTTTGTTTTGA hCoV-NL63 AY567487

(SEQ ID NO: 29)

ACACTTGTTTTGGTGTTAGTAAACCTAATGCCATTGATGTTGAACATT

TAGAGCTTAAAGAAACTGTTTTTGTTGAACCTAAGGATGGTGGTCAAT

TTTTTGTTTCTGGTGATTATCTTTGGTATGT hCoV 229E AF304460

(SEQ ID NO: 30)

ACATGCCAATTGCAGACCCTACACATTTTGACATTGAAGAAGTTGAAC

TTTTAGATGCAGAGTTTGTAGAACCAGGCTGTGGTGGTATTTTGGCAG

TAATAGATGAGCACGTCTTTTATAAGAAGG hCoV-HKU1 MH940245.1

(SEQ ID NO: 31)

ACTGGTGACAATGACGATGAAGATGTTGTTACTGGTGACAATGACGAT

GAAGATGTTGTTACTGGTGACAATGACGATGAAGATGTTGTTACTGGT

GACAATGACGATGAAGAGATTGTTACTGGTGACAATGATGACCAAATT

GTTGTTACTGGTGATGATGTAGATGATATTGAAAGTGTCTATGATTTT

G

SARS CoV GZ02 AY390556.1 China (SEQ ID NO: 32)

AAGAAGAAGAGGAAGACTGGCTGGATGATACTACTGAGCAATCAGAGA

TTGAGCCAGAACCAGAACCTACACCTGAAGAACCAGTTAATCAGTTTA

CTGGTTATTTAAAACTTAC

SARS CoV ZS-B AY394996.1 China (SEQ ID NO: 33)

AAGAAGAAGAGGAAGACTGGCTGGATGATACTACTGAGCAATCAGAGA

TTGAGCCAGAACCAGAACCTACACCTGAAGAACCAGTTAATCAGTTTA

CTGGTTATTTAAAACTTAC

Bat SARS-like CoV Rs4231 KY417146.1 China (SEQ ID NO: 34)

AAGAAGAAGAGGACTGGCTTGGTGATGCTACTGAATTATCGGAGCATG

AACCAGAACCAGAACTAACACCTGAAGAACCAGTTAACCAGTTTACTG

GTTATTTAAAACTTAC 2019-nCoV MN988713 Atlanta USA (SEQ ID NO: 35)

AAGAGCAAGAAGAAGATTGGTTAGATGATGATAGTCAACAAACTGTTG

GTCAACAAGACGGCAGTGAGGACAATCAGACAACTACTATTCAAACAA

TTGTTGAGGTTCAACCTCAATTAGAGATGGAACTTACACCAGTTGTTC

AGACTATTGAAGTGAATAGTTTTAGTGGTTATTTAAAACTTAC 2019-nCoV MN988669.1 WuhanUniversity China (SEQ ID NO: 36)

AAGAGCAAGAAGAAGATTGGTTAGATGATGATAGTCAACAAACTGTTG

GTCAACAAGACGGCAGTGAGGACAATCAGACAACTACTATTCAAACAA

TTGTTGAGGTTCAACCTCAATTAGAGATGGAACTTACACCAGTTGTTC

AGACTATTGAAGTGAATAGTTTTAGTGGTTATTTAAAACTTAC 2019-nCoV MN908947.3 PublicHealth China (SEQ ID NO: 37)

AAGAGCAAGAAGAAGATTGGTTAGATGATGATAGTCAACAAACTGTTG

GTCAACAAGACGGCAGTGAGGACAATCAGACAACTACTATTCAAACAA

-continued

TTGTTGAGGTTCAACCTCAATTAGAGATGGAACTTACACCAGTTGTTC

AGACTATTGAAGTGAATAGTTTTAGTGGTTATTTAAAACTTAC

Primer and Probe Sequences

Primer and probe sequences for specific amplification and detection of SARS-CoV-2 Orf1ab nucleic acid sequence were designed based on the multiple sequence alignment, and are set out below.

Forward primers 2019-nCoV-ARP1.1F (SEQ ID NO: 1)

CTGTTGGTCAACAAGACGGCA 2019-nCoV-ARP1.2F (SEQ ID NO: 2)

GTCAACAAACTGTTGGTCAA 2019-nCoV-ARP1.3F (SEQ ID NO: 3)

GTCAACAAACTGTTGGTCAACA

SA nCoV F2

(SEQ ID NO: 4)

CATTACAGGTGGTGTTGTTCAGTT

Reverse primers 2019-nCoV-ARP1.1R (SEQ ID NO: 5)

CAATAGTCTGAACAACTGGTGT 2019-nCoV-ARP1.2R (SEQ ID NO: 6)

CTGGTGTAAGTTCCATCTCT

SA nCoV R2

(SEQ ID NO: 7)

AGGTGACAATTTGTCCACCGAC

Capture probes 2019-nCoV-AR-CP1.1

(SEQ ID NO: 8)

GGCAGTGAGGACAATCAGCAACTAC 2019-nCoV-AR-CP1.2

(SEQ ID NO: 9)

GAGGACAATCAGACAACTACTATTC

SA nCoV CP2

(SEQ ID NO: 10)

ACCCGTCCTTGATTGGCTTG

Detector probes 2019-nCoV-AR-DP1.1

(SEQ ID NO: 11)

CAAACAATTGTTGAGGTTCAACCTC 2019-nCoV-AR-DP1.2

(SEQ ID NO: 12)

GAGGTTCAACCTCAATTAGAGATGG

SA nCoV DP2

(SEQ ID NO: 13)

GGAAGGTGTAGAGTTTCTTAGAGAC

Example 2

Design of Primers and Probes from Coronavirus Nucleocapsid Gene Sequence Alignments Nucleic acid sequences of the gene encoding the nucleocapsid (N) protein for all seven human coronaviruses (229E, SARS, HKU1, MERS, OC43, NL63, and SARS-CoV-2) were obtained, including three different SARS-CoV-2 sequences, and a bat SARS-like coronavirus sequence.

These sequences were aligned using the CLUSTAL 0 (1.2.4) multiple sequence alignment software. The multiple sequence alignment is shown in FIG. 3. In FIG. 3, SARS-CoV-2 is referred to by its previous provisional name, 2019-nCOV (2019 novel coronavirus).

The sequences obtained are shown below:

```
MERS CoV KJ477103.2
                                        (SEQ ID NO: 38)
AGAACTGGATCATGGTGGTCATTCAATCCTGAGACTAATTGCCTTTTG

AACGTTCCATTTGGTGGTACAACTGTCGTACGTCCACTCGTAGAGGAC

TCTACCAGTGTAACTGCTGTTGTAACCAATGGCCACCTCAAAATGGCT

GGCATGCATTTCGGTGCTTGTGACTACGACAGACTTCCTAATGAAGTC

ACCGTGGCCAAACCCAATGTGCTGATTGCTTTAAAAATGGTGAAGCGG

CAAAGCTACGGAACTAATTCCGGCGTTGCCATTTACCATAGATATAAG

GCAGGTAATTACAGGAGTCCGCCTATTACGGCGGATATTGAACTTGCA

TTGCTTCGAGCTTAGGCTCTTTAGTAAGAGTATCTTAATTGATTTTAA

CGAATCTCAATTTCATTGTTATGGCATCCCCTGCTGCACCTCGTGCTG

TTTC

hCoV OC43 KU131570
                                        (SEQ ID NO: 39)
AGAACCGGCAGTTTTTGGAGTTTCAACCCAGAAACAAACAACTTGATG

TGTATAGATATGAAAGGAACAATGTTTGTTAGGCCAATAATTGAGGAC

TACCATACCCTGACGGTCACAATAATACGCGGTCATCTTTACATTCAA

GGTATAAAACTAGGTACTGGCTATTCTTTGGCAGATTTGCCAGCTTAT

ATGACTGTTGCTAAGGTCACATACCTGTGCACATATAAGCGTGGTTTT

CTTGACAAGATAAGCGATACTAGTGGTTTTGCTGTTTATGTTAAGTCC

AAAGTCGGTAATTACCGACTGCCATCAACCCAAAAGGGTTCAGGCATG

GACACCGCATTGTTGAGAAATAATATCTAAATTTTAAGGATGTCTTTT

ACTCCTGGTAAGCAATCCAGTAGTAGAGCGTCCTCTGGAAATCGTTCT

GGTAATGGCATCCTTAAGTG

hCoV-NL63 AY567487
                                        (SEQ ID NO: 40)
CGTGTTAAAACTTTTTGGGCTTTTAATCCTGAAACTAATGCAATCATC

TCTCTCCAGGTTTACGGACATAATTATTACTTACCGGTGATGGCTGCA

CCTACAGGTGTTACATTAACACTTCTTAGTGGTGTACTTCTTGTTGAT

GGCCATAAGATTGCTACTCGTGTTCAAGTGGGTCAGTTGCCTAAATAT

GTAATAGTTGCTACGCCTAGTACCACAATTGTTTGTGACCGTGTTGGT

CGCTCTGTTAATGAAACAAGCCAGACTGGTTGGGCATTCTACGTCCGT

GCTAAACATGGTGATTTTTCTGGTGTTGCCTCTCAGGAGGGTGTTTTG

TCAGAAAGAGAGAAGTTGCTTCATTTAATCTAAACTAAACAAAATGGC

TAGTGTAAATTGGGCCGATGA--CAGAGCTGCTAGGAAGAAATTTCCT

CCTCCTTC

hCoV 229E AF304460
                                        (SEQ ID NO: 41)
CGTGCTCGAACTTTTTGGGCATGGAATCCTGAGGTTAATGCAATCACT

GTCACAACCGTGTTGGGACAGACATACTATCAACCCATTCAACAAGCT
```

-continued

```
CCAACAGGCATTACTGTGACCTTGCTGAGCGGCGTGCTTTACGTTGAC

GGACATAGATTGGCTTCAGGTGTTCAGGTTCATAACCTACCTGAATAC

ATGACAGTTGCCGTGCCGAGCACTACTATAATTTATAGTAGAGTCGGA

AGGTCCGTAAATTCACAAAATAGCACAGGCTGGGTTTTCTACGTACGA

GTAAAACACGGTGATTTTTCTGCAGTGAGCTCTCCCATGAGCAACATG

ACAGAAAACGAAAGATTGCTTCATTTTTTCTAAACTGAACGAAAAGAT

GGCTACAGTCAAATGGGCTGATGCATCTGAACCACAACGTGGTCGTCA

GGGTAGAATACCTTATTC

hCoV-HKU1 MH940245.1
                                        (SEQ ID NO: 42)
AGAACTGGCAGTTGGTGGAGTTTTAACCCAGAGACTAATAATCTTATG

TGTATTGATATGAAAGGTAAGATGTATGTTAGGCCAGTTATTGAGGAC

TATCATACATTAACGGCTACTGTTATCCGTGGTCATCTTTATATACAG

GGTGTTAAACTTGGCACTGGTTACACGCTTGCCGATTTGCCTGTTTAT

GTTACTGTAGCTAAGGTGCAAGTCCTCTGTACTTATAAACGTGCCTTT

TTAGATAAGTTAGATGTTAATAGTGGTTTTGCTGTTTTTGTTAAGTCT

AAAGTTGGTAACTATCGTTTACCTTCTAGTAAATCTAGTGGTATGGAT

ACTGCCTTGTTGAGAGCTTAAATCTAAACTATTAGGATGTCTTATACT

CCCGGTCATCATGCTGGAAGTAGAAGCTCCTCTGGAAATCGTTCAGGA

ATCCTCAAGAA

SARS CoV GZ02 AY390556.1 China
                                        (SEQ ID NO: 43)
GCAGTTGCATACGCACTGTAGTACAGCGCTGTGCATCTAATAAACCTC

ATGTGCTTGAAGATCCTTGTCCTACTGGTTACCAACCTGAATGGAATA

TAAGGTACAACACTAGGGGTAATACTTATAGCACTGCTTGGCTTTGTG

CTCTAGGAAAGGTTTTACCTTTTCATAGATGGCACACTATGGTTCAAA

CATGCACACCTAATGTTACTATCAACTGTCAAGATCCAGCTGGTGGTG

CGCTTATAGCTAGGTGTTGGTACCTTCATGAAGGTCACCAAACTGCTG

CATTTAGAGACGTATTTGTTGTTTTAAATAAACGAACAAATTAAAATG

TCTGATAATGGACCCCAATCAAACCAACGTAGTGCCCCCCGCATTACA

TTTGGTGGACCCACAGATTC

SARS CoV ZS-B AY394996.1 China
                                        (SEQ ID NO: 44)
GCAGTTGCATACGCACTGTAGTACAGCGCTGTGCATCTAATATAGCAC

TGCTTGGCTTTGTGCTCTAGGAAAGGTTTTACCTTTTCATAGATGGCA

CACTATGGTTCAAACATGCACACCTAATGTTACTATCAACTGTCAAGA

TCCAGCTGGTGGTGCGCTTATAGCTAGGTGTTGGTACCTTCATGAAGG

TCACCAAACTGCTGCATTTAGAGACGTACTTGTTGTTTTAAATAAACG

AACAAATTAAAATGTCTGATAATGGACCCCAATCAAACCAACGTAGTG

CCCCCCGCATTACATTTGGTGGACCCACAGATTC

Bat SARS-like CoV Rs4231 KY417146.1 China
                                        (SEQ ID NO: 45)
GTGTATTGCATGCATAAAGAATGCAGTATACAAGAATGTTGTGAAAAT

CAACCATTCCAACCTGAAGACCCATGTCCAATACATTATTATTCGGAC

TGGTTTGTAAAAATTGGACCTCGCAAGTCTGCTCGCCTAGTACAACTT
```

-continued

TGTGCTGGTGAATATGGACACAGAGTTCCAATACATTATGAAATGTTT

GGCAATTATACTATTTCATGTGAACCACTTGAAATAAATTGTCAAAAC

CCACCAGTTGGAAGTCTCATTGTACGTTGTTCATATGATGTTGACTTT

ATGGAGTATCACGACGTTCGTGTTGTTCTAGATTTCATCTAAACGAAC

AAACTAAAATGTCTGATAATGGACCCCAACCAAATCAGCGTAGTGCCC

CCCGCATTACATTTGGTGGACCCACAGATTC 2019-nCoV MN988713 Atlanta USA
(SEQ ID NO: 46)
GCTGCATTTCACCAAGAATGTAGTTTACAGTCATGTACTCAACATCAA

CCATATGTAGTTGATGACCCGTGTCCTATTCACTTCTATTCTAAATGG

TATATTAGAGTAGGAGCTAGAAAATCAGCACCTTTAATTGAATTGTGC

STGGATGAGGCTGGTTCTAAATCACCCATTCAGTACATCGATATCGGT

AATTATACAGTTTCCTGTTYACCTTTTACAATTAATTGCCAGGAACCT

AAATTGGGTAGTCTTGTAGTGCGTTGTTCGTTCTATGAAGACTTTTTA

GAGTATCATGACGTTCGTGTTGTTTTAGATTTCATCTAAACGAACAAA

CTAAAATGTCTGATAATGGACCCCAAAATCAGCGAAATGCACCCCGCA

TTACGTTTGGTGGACCCTCAGATTC 2019-nCoV MN988669.1 WuhanUniversity China
(SEQ ID NO: 47)
GCTGCATTTCACCAAGAATGTAGTTTACAGTCATGTACTCAACATCAA

CCATATGTAGTTGATGACCCGTGTCCTATTCACTTCTATTCTAAATGG

TATATTAGAGTAGGAGCTAGAAAATCAGCACCTTTAATTGAATTGTGC

STGGATGAGGCTGGTTCTAAATCACCCATTCAGTACATCGATATCGGT

AATTATACAGTTTCCTGTTYACCTTTTACAATTAATTGCCAGGAACCT

AAATTGGGTAGTCTTGTAGTGCGTTGTTCGTTCTATGAAGACTTTTTA

GAGTATCATGACGTTCGTGTTGTTTTAGATTTCATCTAAACGAACAAA

CTAAAATGTCTGATAATGGACCCCAAAATCAGCGAAATGCACCCCGCA

TTACGTTTGGTGGACCCTCAGATTC 2019-nCoV MN908947.3 PublicHealth China
(SEQ ID NO: 48)
GCTGCATTTCACCAAGAATGTAGTTTACAGTCATGTACTCAACATCAA

CCATATGTAGTTGATGACCCGTGTCCTATTCACTTCTATTCTAAATGG

TATATTAGAGTAGGAGCTAGAAAATCAGCACCTTTAATTGAATTGTGC

STGGATGAGGCTGGTTCTAAATCACCCATTCAGTACATCGATATCGGT

AATTATACAGTTTCCTGTTYACCTTTTACAATTAATTGCCAGGAACCT

AAATTGGGTAGTCTTGTAGTGCGTTGTTCGTTCTATGAAGACTTTTTA

GAGTATCATGACGTTCGTGTTGTTTTAGATTTCATCTAAACGAACAAA

CTAAAATGTCTGATAATGGACCCCAAAATCAGCGAAATGCACCCCGCA

TTACGTTTGGTGGACCCTCAGATTC

Primer and Probe Sequences

Primer and probe sequences for specific amplification and detection of SARS-CoV-2 nucleocapsid nucleic acid sequence were designed based on the multiple sequence alignment, and are set out below.

Forward Primer
SA-nCoV-F2.3
(SEQ ID NO: 14)
TAGTTGATGACCCGTGTCCT

Reverse Primers
SA-nCoV-R2.3
(SEQ ID NO: 15)
TGGGGTCCATTATCAGACAT

SA-nCoV-R2.4
(SEQ ID NO: 16)
CAACACGAACGTCATGATAC

SA-nCoV-R2.5
(SEQ ID NO: 17)
CATAGAACGAACAACGCAC

Capture Probe
SA-nCoV-CP2.3
(SEQ ID NO: 18)
CTGGTTCTAAATCACCCATTCA

Detector Probe
SA-nCoV-DP2.3
(SEQ ID NO: 19)
GAACCTAAATTGGGTAGTCTTGTAG

SA-nCoV-DP2.4
(SEQ ID NO: 20)
GGAACCTAAATTGGGTAGTCTTG

Example 3

Point-of-Care (POC) Nucleic Acid Test for Detecting SARS-CoV-2

SARS-CoV-2 target RNA was extracted, reverse transcribed, and amplified by isothermal nucleic acid amplification, and the amplification products were detected by rapid visual detection with a dipstick, using a simple amplification-based assay (SAMBA) method similar to the method described in Lee et al., Journal of Infectious Diseases 2010; 201 (S1): S65-S71.

Briefly, a reverse nucleic acid amplification primer comprises nucleic acid sequence complementary to a portion of SARS-CoV-2 target RNA so that the primer can hybridise specifically to the target RNA, and a single stranded-version of a promoter sequence for a DNA-dependent RNA polymerase at its 5'-end. The reverse primer hybridizes to the RNA target. An RNA-dependent DNA polymerase extends the reverse primer to synthesise a complementary DNA (cDNA) copy of the RNA target. A DNA/RNA duplex-specific ribonuclease digests the RNA of the RNA-cDNA hybrid. A forward nucleic acid amplification primer comprises nucleic acid sequence complementary to a portion of the cDNA. The forward primer hybridizes to the cDNA downstream of the part of the cDNA formed by the reverse primer. The forward primer is extended by a DNA-dependent DNA polymerase to produce a second DNA strand which extends through the DNA-dependent RNA polymerase promoter sequence at one end (thereby forming a double stranded promoter). This promoter is used by a DNA-dependent RNA polymerase to synthesise a large number of RNAs complementary to the original target sequence. These RNA products then function as templates for a cyclic phase of the reaction, but with the primer hybridising steps reversed, i.e., the forward primer followed by the reverse primer.

The following primer/probe sequences were used for isothermal amplification, capture and detection of SARS-CoV-2 nucleic acid:

ORF1ab

```
forward primer 2019-CoV-ARP1.1F:
                                          (SEQ ID NO: 1)
CTGTTGGTCAACAAGACGGCA;

reverse primer 2019-CoV-ARP1.1R:
                                          (SEQ ID NO: 5)
CAATAGTCTGAACAACTGGTGT,

with T7 promoter sequence at its 5'-end:
                                         (SEQ ID NO: 21)
aattctaatacgactcactatagggagaagg;

capture probe 2019-CoV-AR-CP1.2:
                                          (SEQ ID NO: 9)
GAGGACAATCAGACAACTACTATTC;

detector probe 2019-CoV-AR-DP1.2:
                                         (SEQ ID NO: 12)
GAGGTTCAACCTCAATTAGAGATGG.
```

Nucleocapsid Protein (NP)

```
forward primer SA_nCoV_F2.3:
                                         (SEQ ID NO: 14)
TAGTTGATGACCCGTGTCCT

reverse primer SA_nCoV_R2.4:
                                         (SEQ ID NO: 16)
CAACACGAACGTCATGATAC,

with T7 promoter sequence at its 5'-end:
                                         (SEQ ID NO: 22)
aattctaatacgactcactatagggggaaaag;

capture probe SA_nCoV_CP2.3:
                                         (SEQ ID NO: 18)
CTGGTTCTAAATCACCCATTCA

detector probe SA_nCoV_DP2.3:
                                         (SEQ ID NO: 19)
GAACCTAAATTGGGTAGTCTTGTAG
```

Isothermal amplification, capture and detection was carried out for 1000, 100, 10, and 0 SARS-CoV-2 RNA target copies per test to determine the sensitivity of the test.

The chromatographic strip comprises a capture zone with capture probe 2019-CoV-AR-CP1.2 (GAGGACAATCAGACAACTACTATTC; SEQ ID NO: 9) (for capturing amplified nucleic acid of the ORF1ab region) immobilised in a first, upper line, and capture probe SA_nCOV_CP2.3 (CTGGTTCTAAATCACCCATTCA; SEQ ID NO: 18) (for capturing amplified nucleic acid of Nucleocapsid region) immobilised in a separate second, lower line. A third, uppermost line comprises a capture probe for hybridising to amplified nucleic acid of an internal control.

Isothermal amplification, capture and detection was also carried out for SARS and MERS target RNA (at >100,000 copies per test).

The results are recorded in FIG. 5. The results show that SARS-CoV-2 target RNA was efficiently detected down to 10 copies/per test, and that the test results are highly specific for SARS-CoV-2 target RNA over SARS and MERS target RNA.

Example 4

Sensitivity and Specificity of POC Nucleic Acid Test for Detecting SARS-CoV-2 in Clinical Samples This example describes an assessment of the clinical sensitivity and specificity of a SARS-CoV-2 Test according to an embodiment of the invention on 102 blinded frozen clinical samples collected from symptomatic individuals.

The samples were tested independently according to a real-time RT-PCR Reference method described in Corman et al., "*Detection of* 2019 *novel coronavirus* (2019-*nCOV*) *by real-time RT-PCR", Euro Surveill.* 2020; 25 (3): pii=2000045. The results obtained by this method were compared with the results obtained using a method according to an embodiment of the invention similar to the method described in Example 3, carried out using an automated sample processing system similar to that described in WO 2014/140640. The method is referred to herein as the SAMBA II SARS-CoV-2 Test. The test is a fully automated isothermal nucleic acid amplification test which is run using the CE-marked SAMBA II instrument system consisting of the SAMBA II Assay Module and Tablet Module.

102 nose/throat swab samples were collected from symptomatic individuals in Viral Transport Medium (VTM) and diluted 1:2 with buffer before supply for testing. The samples were provided blinded and coded with no patient information available to the tester.

a) Testing Criteria

| | |
|---|---|
| Samples positive by Reference method | SAMBA IC signal ≥0.5, Orf > 0 N ≥ 0 |
| Samples negative by Reference method | SAMBA IC signal ≥3, Orf = 0 N = 0 |

b) Clinical Performance Versus Reference Method (qPCR):

% Sensitivity: ≥98%

% Specificity: 100%

Results:

| Sample | Test date | IC | ORF | N | SAMBA result | Data (reference method) (Ct Value) |
|---|---|---|---|---|---|---|
| 1 | 27 Mar. 2020 | 4.5 | 5.0 | 4.5 | POSITIVE | 19.86 |
| 2 | 27 Mar. 2020 | 5.0 | 4.5 | 5.0 | POSITIVE | 19.07 |
| 3 | 27 Mar. 2020 | 4.5 | 4.5 | 0.5 | POSITIVE | 27.99 |
| 4 | 27 Mar. 2020 | 5.0 | 4.0 | 0.0 | POSITIVE | 29.31 |
| 5 | 27 Mar. 2020 | 5.0 | 1.0 | 0.0 | POSITIVE | 31.81 |
| 6 | 27 Mar. 2020 | 4.5 | 5.0 | 0.0 | POSITIVE | 30.44 |
| 7 | 27 Mar. 2020 | 4.0 | 5.0 | 3.0 | POSITIVE | 25.12 |
| 8 | 27 Mar. 2020 | 5.0 | 0.0 | 0.0 | NEGATIVE | NEGATIVE |
| 9 | 27 Mar. 2020 | 4.5 | 5.0 | 5.0 | POSITIVE | 20.4 |
| 10 | 27 Mar. 2020 | 4.5 | 3.5 | 0.0 | POSITIVE | 25.19 |
| 11 | 27 Mar. 2020 | 5.0 | 0.0 | 0.0 | NEGATIVE | NEGATIVE |
| 12 | 27 Mar. 2020 | 4.5 | 5.0 | 5.0 | POSITIVE | 31 |
| 13 | 27 Mar. 2020 | 4.0 | 5.0 | 0.0 | POSITIVE | 27.35 |
| 14 | 27 Mar. 2020 | 5.0 | 3.5 | 0.0 | POSITIVE | 30.6 |
| 15 | 27 Mar. 2020 | 4.0 | 5.0 | 3.0 | POSITIVE | 25.76 |
| 16 | 27 Mar. 2020 | 5.0 | 2.5 | 0.5 | POSITIVE | 30.49 |
| 17 | 27 Mar. 2020 | 4.0 | 5.0 | 4.5 | POSITIVE | 25.19 |
| 18 | 27 Mar. 2020 | 4.0 | 5.0 | 4.5 | POSITIVE | 19.82 |
| 19 | 27 Mar. 2020 | 4.5 | 5.0 | 4.5 | POSITIVE | 21.22 |
| 20 | 27 Mar. 2020 | 4.5 | 5.0 | 0.5 | POSITIVE | 19.33 |
| 21 | 27 Mar. 2020 | 4.5 | 5.0 | 4.5 | POSITIVE | 18.82 |
| 22 | 27 Mar. 2020 | 4.5 | 5.0 | 0.5 | POSITIVE | 26.57 |
| 23 | 27 Mar. 2020 | 5.0 | 0.0 | 0.0 | NEGATIVE | NEGATIVE |
| 24 | 27 Mar. 2020 | 5.0 | 1.0 | 0.5 | POSITIVE | 26.53 |
| 25 | 27 Mar. 2020 | 5.0 | 0.0 | 0.0 | NEGATIVE | 31.18 |
| 26 | 27 Mar. 2020 | 4.5 | 5.0 | 1.5 | POSITIVE | 22.81 |
| 27 | 27 Mar. 2020 | 3.0 | 3.0 | 2.5 | POSITIVE | 20.38 |
| 28 | 27 Mar. 2020 | 4.5 | 5.0 | 4.5 | POSITIVE | 20.43 |
| 29 | 27 Mar. 2020 | 4.5 | 5.0 | 4.0 | POSITIVE | 20.62 |
| 30 | 27 Mar. 2020 | 4.0 | 3.0 | 3.0 | POSITIVE | 14.07 |
| 31 | 27 Mar. 2020 | 4.5 | 4.5 | 4.5 | POSITIVE | 22.58 |
| 32 | 27 Mar. 2020 | 5.0 | 4.5 | 0.5 | POSITIVE | 26.86 |
| 33 | 27 Mar. 2020 | 4.5 | 5.0 | 4.5 | POSITIVE | 21.64 |
| 34 | 27 Mar. 2020 | 4.5 | 5.0 | 3.5 | POSITIVE | 18.56 |
| 35 | 27 Mar. 2020 | 4.5 | 3.5 | 0 | POSITIVE | 24.92 |
| 36 | 27 Mar. 2020 | 4.5 | 5 | 5 | POSITIVE | 19.12 |

-continued

| Sample | Test date | IC | ORF | N | SAMBA result | Data (reference method) (Ct Value) |
|---|---|---|---|---|---|---|
| 37 | 27 Mar. 2020 | 4.5 | 5 | 4.5 | POSITIVE | 19.74 |
| 38 | 27 Mar. 2020 | 4.5 | 5 | 2 | POSITIVE | 24.52 |
| 39 | 27 Mar. 2020 | 5 | 4 | 4.5 | POSITIVE | 16.75 |
| 40 | 27 Mar. 2020 | 4.5 | 5 | 3 | POSITIVE | 22.73 |
| 41 | 27 Mar. 2020 | 4.5 | 4.5 | 4.5 | POSITIVE | 17 |
| 42 | 27 Mar. 2020 | 4 | 5 | 5 | POSITIVE | 21.36 |
| 43 | 27 Mar. 2020 | 4 | 5 | 3.5 | POSITIVE | 15 |
| 44 | 27 Mar. 2020 | 4 | 4.5 | 4 | POSITIVE | 22.54 |
| 45 | 27 Mar. 2020 | 5 | 4.5 | 4.5 | POSITIVE | 23.4 |
| 46 | 27 Mar. 2020 | 4.5 | 4.5 | 5 | POSITIVE | 19.44 |
| 47 | 27 Mar. 2020 | 4.5 | 4 | 4.5 | POSITIVE | 19.05 |
| 48 | 27 Mar. 2020 | 4 | 4.5 | 4.5 | POSITIVE | 20.83 |
| 49 | 27 Mar. 2020 | 4.5 | 5 | 3.5 | POSITIVE | 18.9 |
| 50 | 27 Mar. 2020 | 4.5 | 4.5 | 4.5 | POSITIVE | 20.34 |
| 51 | 27 Mar. 2020 | 4.5 | 5 | 4.5 | POSITIVE | 20.57 |
| 52 | 27 Mar. 2020 | 4.5 | 5 | 4 | POSITIVE | 21.65 |
| 53 | 29 Mar. 2020 | 5 | 5 | 5 | POSITIVE | 20 |
| 54 | 29 Mar. 2020 | 5 | 5 | 3 | POSITIVE | 28 |
| 55 | 29 Mar. 2020 | 5 | 5 | 5 | POSITIVE | 27 |
| 56 | 29 Mar. 2020 | 0 | 0 | 0 | INVALID | |
| 56 (1:4) | 29 Mar. 2020 | 5 | 2 | 0 | POSITIVE | 22 |
| 57 | 29 Mar. 2020 | 4.5 | 5 | 5 | POSITIVE | 24 |
| 58 | 29 Mar. 2020 | 4.5 | 5 | 5 | POSITIVE | 24 |
| 59 | 29 Mar. 2020 | 4.5 | 5 | 3 | POSITIVE | 30 |
| 60 | 29 Mar. 2020 | 5 | 4.5 | 0 | POSITIVE | 26 |
| 61 | 29 Mar. 2020 | 4.5 | 5 | 5 | POSITIVE | 19 |
| 62 | 29 Mar. 2020 | 5 | 3 | 0 | POSITIVE | 27 |
| 63 | 29 Mar. 2020 | 4.5 | 5 | 3.5 | POSITIVE | 20 |
| 64 | 29 Mar. 2020 | 4.5 | 4.5 | 3 | POSITIVE | 28 |
| 65 | 29 Mar. 2020 | 5 | 4.5 | 5 | POSITIVE | 18 |
| 66 | 29 Mar. 2020 | 4.5 | 5 | 3 | POSITIVE | 26 |
| 67 | 29 Mar. 2020 | 5 | 4.5 | 5 | POSITIVE | 22 |
| 68 | 29 Mar. 2020 | 4.5 | 5 | 0 | POSITIVE | 29 |
| 69 | 29 Mar. 2020 | 5 | 1.5 | 0.5 | POSITIVE | 28 |
| 70 | 29 Mar. 2020 | 4.5 | 5 | 5 | POSITIVE | 17 |
| 71 | 29 Mar. 2020 | 5 | 5 | 5 | POSITIVE | 22 |
| 72 | 29 Mar. 2020 | 5 | 5 | 5 | POSITIVE | 23 |
| 73 | 29 Mar. 2020 | 5 | 4.5 | 5 | POSITIVE | 16 |
| 74 | 29 Mar. 2020 | 5 | 4.5 | 5 | POSITIVE | 20 |
| 75 | 29 Mar. 2020 | 4 | 5 | 3.5 | POSITIVE | 25 |
| 76 | 29 Mar. 2020 | 4.5 | 5 | 5 | POSITIVE | 25 |
| 77 | 29 Mar. 2020 | 4.5 | 5 | 4.5 | POSITIVE | 22 |
| 78 | 29 Mar. 2020 | 5 | 4.5 | 5 | POSITIVE | 21 |
| 79 | 29 Mar. 2020 | 5 | 0 | 0 | NEGATIVE | NEGATIVE |
| 80 | 29 Mar. 2020 | 5 | 0 | 0 | NEGATIVE | NEGATIVE |
| 81 | 29 Mar. 2020 | 4.5 | 0 | 0 | NEGATIVE | NEGATIVE |
| 82 | 29 Mar. 2020 | 5 | 0 | 0 | NEGATIVE | NEGATIVE |
| 83 | 29 Mar. 2020 | 4.5 | 0 | 0 | NEGATIVE | NEGATIVE |
| 84 | 29 Mar. 2020 | 5 | 0 | 0 | NEGATIVE | NEGATIVE |
| 85 | 29 Mar. 2020 | 5 | 0 | 0 | NEGATIVE | NEGATIVE |
| 86 | 29 Mar. 2020 | 0 | 0 | 0 | INVALID | |
| 86 (1:10) | 29 Mar. 2020 | 5 | 0 | 0 | NEGATIVE | NEGATIVE |
| 87 | 29 Mar. 2020 | 5 | 0 | 0 | NEGATIVE | NEGATIVE |
| 88 | 29 Mar. 2020 | 5 | 0 | 0 | NEGATIVE | NEGATIVE |
| 89 | 29 Mar. 2020 | 5 | 0 | 0 | NEGATIVE | NEGATIVE |

-continued

| Sample | Test date | IC | ORF | N | SAMBA result | Data (reference method) (Ct Value) |
|---|---|---|---|---|---|---|
| 90 | 29 Mar. 2020 | 5 | 0 | 0 | NEGATIVE | NEGATIVE |
| 91 | 29 Mar. 2020 | 5 | 0 | 0 | NEGATIVE | NEGATIVE |
| 92 | 29 Mar. 2020 | 5 | 0 | 0 | NEGATIVE | NEGATIVE |
| 93 | 29 Mar. 2020 | 5 | 0 | 0 | NEGATIVE | NEGATIVE |
| 94 | 29 Mar. 2020 | 0 | 0 | 0 | INVALID | |
| 94 (1:4) | 29 Mar. 2020 | 5 | 0 | 0 | NEGATIVE | NEGATIVE |
| 95 | 29 Mar. 2020 | 4 | 0 | 0 | NEGATIVE | NEGATIVE |
| 96 | 29 Mar. 2020 | 4.5 | 5 | 1 | POSITIVE | 25 |
| 97 | 29 Mar. 2020 | 5 | 0 | 0 | NEGATIVE | NEGATIVE |
| 98 | 29 Mar. 2020 | 5 | 0 | 0 | NEGATIVE | NEGATIVE |
| 99 | 29 Mar. 2020 | 5 | 0 | 0 | NEGATIVE | NEGATIVE |
| 100 | 29 Mar. 2020 | 4 | 0 | 0 | NEGATIVE | NEGATIVE |
| 101 | 29 Mar. 2020 | 4 | 0 | 0 | NEGATIVE | NEGATIVE |
| 102 | 29 Mar. 2020 | 4.5 | 0 | 0 | NEGATIVE | NEGATIVE |

In total 102 samples were tested by SAMBA, of which 74 were positive, 25 were negative and 3 were invalid by SAMBA. The invalid samples were further diluted in Buffer 1:4 and 1:10 and retested, which resulted in 1 positive and 2 negatives.

Compared with the reference laboratory test, there were 75 concordant positives, 26 concordant negatives and one false-negative by SAMBA (see table below). Therefore, the SAMBA II SARS-CoV-2 Test has a sensitivity of 98.68% (95% CI 92.89-99.97%), specificity of 100% (95% CI 87.23-100%), PPV of 100% and NPV of 96.43% (79.39-99.47%) when compared to the reference method. The one discrepant sample gave a high Ct value on the reference method (>31) and it was further diluted (1:2) for SAMBA testing as the UTM was found to interfere with the assay, which may explain the false-negative result.

Clinical performance in 102 blinded surplus clinical samples compared to reference method:

| | | Reference method | |
|---|---|---|---|
| | | POSITIVE | NEGATIVE |
| SAMBA SARS-CoV-2 Test | POSITIVE | 75 | 0 |
| | NEGATIVE | 1 | 26 |

CONCLUSIONS

The sensitivity and specificity of the SAMBA II SARS-CoV-2 Test was 98.68% (95% CI 92.89-99.97%) and specificity of 100% (95% CI 87.23-100%) respectively when tested 1:2 in buffer compared to the Reference method.

The invention claimed is:

1. A method for determining whether a sample includes a severe acute respiratory syndrome coronavirus 2 (SARS-CoV-2) nucleic acid, wherein the method comprises amplifying a nucleic acid of the sample, or amplifying a nucleic acid derived from the nucleic acid of the sample, by an isothermal amplification reaction using a set of forward and reverse nucleic acid amplification primers selected from (i)-(iii):

(i) at least one forward nucleic acid primer and at least one reverse nucleic acid amplification primer that each hybridize specifically to a nucleic acid sequence that is conserved in the ORF1ab gene of SARS-CoV-2, wherein the at least one forward nucleic acid primer comprises the nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), or CATTACAGGTGGTGTTGTTCAGTT (SEQ ID NO: 4); and the at least one reverse nucleic acid primer comprises the nucleic acid sequence of: CAATAGTCTGAACAACTGGTGT (SEQ ID NO: 5), CTGGTGTAAGTTCCATCTCT (SEQ ID NO: 6), or AGGTGACAATTTGTCCACCGAC (SEQ ID NO: 7);

(ii) a forward nucleic acid primer and a reverse nucleic acid primer that each hybridize specifically to a nucleic acid sequence that is conserved in the nucleocapsid gene of SARS-CoV-2, wherein the forward nucleic acid primer comprises the nucleic acid sequence of: TAGTTGATGACCCGTGTCCT (SEQ ID NO: 14); and the reverse nucleic acid primer comprises the nucleic acid sequence of: TGGGGTCCATTATCAGACAT (SEQ ID NO: 15), CAACACGAACGTCATGATAC (SEQ ID NO: 16), or CATAGAACGAACAACGCAC (SEQ ID NO: 17); or (iii) a combination of (i) and (ii).

2. A method according to claim 1, which further comprises reverse transcribing SARS-CoV-2 RNA of the sample, and amplifying a product of the reverse transcription by an isothermal amplification reaction using the forward and reverse nucleic acid amplification primers, optionally wherein the reverse nucleic acid primer further comprises a promoter sequence for a DNA-dependent RNA polymerase at its 5'-end, and reverse transcription is carried out using the reverse nucleic acid primer and/or which further comprises isolating nucleic acid of the sample before reverse transcribing SARS-CoV-2 RNA of the sample present in the isolated nucleic acid.

3. A method according to claim 1, which further comprises capturing a product of the isothermal amplification reaction by hybridising the nucleic acid of the product to a nucleic acid capture probe, wherein the capture probe hybridises specifically to the nucleic acid sequence that is conserved in a SARS-CoV-2 nucleic acid, but not in other human coronavirus nucleic acid, wherein:

the forward and reverse nucleic acid primers hybridise specifically to the nucleic acid sequence that is conserved in the ORF1ab gene of SARS-CoV-2, and the capture probe hybridizes specifically to the nucleic acid sequence that is conserved in the ORF1ab gene of SARS-CoV-2, wherein the capture probe comprises the nucleic acid sequence of: GGCAGTGAGGACAATCAGCAACTAC (SEQ ID NO: 8), GAGGACAATCAGACAACTACTATTC (SEQ ID NO: 9), or ACCCGTCCTTGATTGGCTTG (SEQ ID NO: 10); and/or the forward and reverse nucleic acid primers hybridise specifically to the nucleic acid sequence that is conserved in the nucleocapsid gene of SARS-CoV-2, and the capture probe hybridizes specifically to the nucleic acid sequence that is conserved in the nucleocapsid gene of SARS-CoV-2, wherein the capture probe comprises the nucleic acid sequence of: CTGGTTCTAAATCACCCATTCA (SEQ ID NO: 18).

4. A method according to claim 1, which further comprises detecting a product of the isothermal amplification reaction by hybridising the product to a nucleic acid detector probe, wherein the detector probe hybridises specifically to a SARS-CoV-2 nucleic acid sequence that is conserved in the SARS-CoV-2 nucleic acid, but not in other human coronavirus nucleic acid, wherein:

the forward and reverse nucleic acid primers hybridise specifically to the nucleic acid sequence that is conserved in the ORF1ab gene of SARS-CoV-2, and the detector probe hybridizes specifically to the nucleic acid sequence that is conserved in the ORF1ab gene of SARS-CoV-2, wherein the detector probe comprises the nucleic acid sequence of: CAAACAATTGTTGAGGTTCAACCTC (SEQ ID NO: 11), GAGGTTCAACCTCAATTAGAGATGG (SEQ ID NO: 12), or GGAAGGTGTAGAGTTTCTTAGAGAC (SEQ ID NO: 13); and/or the forward and reverse nucleic acid primers hybridise specifically to the nucleic acid sequence that is conserved in the nucleocapsid gene of SARS-CoV-2, and the detector probe hybridizes specifically to the nucleic acid sequence that is conserved in the nucleocapsid gene of SARS-CoV-2, wherein the detector probe comprises the nucleic acid sequence of: GAACCTAAATTGGGTAGTCTTGTAG (SEQ ID NO: 19) or GGAACCTAAATTGGGTAGTCTTG (SEQ ID NO: 20);

optionally wherein the detector probe is labelled with a visually detectable label.

5. A method according to claim 4, wherein the detection of the product of the isothermal amplification reaction is carried out by chromatographic dipstick assay.

6. A method according to claim 1, wherein the sample is a biological sample obtained from a subject suspected of being infected with SARS-CoV-2, optionally wherein the sample is a nasopharyngeal or a throat swab sample obtained from a subject suspected of being infected with SARS-CoV-2, and/or which is an in vitro method.

7. A kit for determining whether a sample includes a SARS-CoV-2 nucleic acid, which comprises:

a forward nucleic acid amplification primer and a reverse nucleic acid amplification primer, for amplifying a template nucleic acid by an isothermal amplification reaction, wherein each nucleic acid amplification primer hybridises specifically to a nucleic acid sequence that is conserved in the SARS-CoV-2 nucleic acid, but not in other human coronavirus nucleic acid;

a nucleic acid capture probe, wherein the capture probe hybridises specifically to a nucleic acid sequence that is conserved in the SARS-CoV-2 nucleic acid, but not in other human coronavirus nucleic acid, or the complement thereof; and/or a nucleic acid detector probe, wherein the detector probe hybridises specifically to a nucleic acid sequence that is conserved in the SARS-CoV-2 nucleic acid, but not in other human coronavirus nucleic acid, or the complement thereof, wherein the detector probe comprises a detectable label for labelling a product of the isothermal nucleic acid amplification, wherein:

the forward and the reverse nucleic acid primers hybridize specifically to a nucleic acid sequence that is conserved in the ORF1ab gene of SARS-CoV-2, wherein the forward nucleic acid primer comprises the nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), or CATTACAGGTGGTGTTGTTCAGTT (SEQ ID NO: 4), and the reverse nucleic acid primer comprises the nucleic acid sequence of: CAATAGTCTGAACAACTGGTGT (SEQ ID NO: 5), CTGGTGTAAGTTCCATCTCT (SEQ ID NO: 6), or AGGTGACAATTTGTCCACCGAC (SEQ ID NO: 7); and/or the forward and reverse nucleic acid primers hybridize specifically to a nucleic acid sequence that is conserved in the nucleocapsid gene of SARS-CoV-2, wherein the forward nucleic acid primer comprises the nucleic acid sequence of: TAGTTGATGACCCGTGTCCT (SEQ ID NO: 14) and the reverse nucleic acid primer comprises the nucleic acid sequence of: TGGGGTCCATTATCAGACAT (SEQ ID NO: 15), CAACACGAACGTCATGATAC (SEQ ID NO: 16), or CATAGAACGAACAACGCAC (SEQ ID NO: 17).

8. A kit according to claim 7, wherein the reverse nucleic acid primer further comprises a promoter sequence for a DNA-dependent RNA polymerase at its 5'-end for reverse transcription of SARS-CoV-2 RNA using the reverse nucleic acid primer.

9. A kit according to claim 7, wherein: the forward and reverse nucleic acid primers hybridise specifically to the nucleic acid sequence that is conserved in the ORF1ab gene of SARS-CoV-2, and the capture probe hybridizes specifically to the nucleic acid sequence that is conserved in the ORF1ab gene of SARS-CoV-2, wherein the capture probe comprises the nucleic acid sequence of: GGCAGTGAGGACAATCAGCAACTAC (SEQ ID NO: 8), GAGGACAATCAGACAACTACTATTC (SEQ ID NO: 9), or ACCCGTCCTTGATTGGCTTG (SEQ ID NO: 10); and/or the forward and reverse nucleic acid primers hybridise specifically to the nucleic acid sequence that is conserved in the nucleocapsid gene of SARS-CoV-2, and the capture probe hybridizes specifically to the nucleic acid sequence that is conserved in the nucleocapsid gene of SARS-CoV-2, wherein the capture probe comprises the nucleic acid sequence of: CTGGTTCTAAATCACCCATTCA (SEQ ID NO: 18).

10. A kit according to claim 7, wherein:

the forward and reverse nucleic acid primers hybridise specifically to the nucleic acid sequence that is conserved in the ORF1ab gene of SARS-CoV-2, and the detector probe hybridizes specifically to the nucleic acid sequence that is conserved in the ORF1ab gene of SARS-CoV-2, wherein the detector probe comprises the nucleic acid sequence of: CAAACAATTGTTGAGGTTCAACCTC (SEQ ID NO: 11), GAGGTTCAACCTCAATTAGAGATGG (SEQ ID NO: 12), or GGAAGGTGTAGAGTTTCTTAGAGAC (SEQ ID NO: 13); and/or the forward and reverse nucleic acid primers hybridise specifically to the nucleic acid sequence that is conserved in the nucleocapsid gene of SARS-CoV-2, and the detector probe hybridizes specifically to the nucleic acid sequence that is conserved in the nucleocapsid gene of SARS-CoV-2, wherein the detector probe comprises the nucleic acid sequence of: GAACCTAAATTGGGTAGTCTTGTAG (SEQ ID NO: 19) or GGAACCTAAATTGGGTAGTCTTG (SEQ ID NO: 20).

11. A kit according to claim 7, which further comprises:

an RNA-dependent DNA polymerase, a DNA-dependent DNA polymerase, a DNA/RNA duplex-specific ribonuclease, and a DNA-dependent RNA polymerase; and/or a swab stick for obtaining a nasopharyngeal or throat swab sample from a subject, optionally wherein the kit further comprises a first swab stick for obtaining a nasopharyngeal swab sample from a subject, and a second swab stick for obtaining a throat swab sample from a subject; and/or a chromatographic test strip for capturing and detecting a product of the isothermal nucleic acid amplification; and/or a lysis/binding buffer, an elution buffer, and optionally a wash buffer, for extracting nucleic acid from a biological sample obtained from the subject.

12. A set of primers for amplifying SARS-CoV-2 nucleic acid by an isothermal nucleic acid amplification reaction, which comprises a forward nucleic acid amplification primer and a reverse nucleic acid amplification primer, wherein each nucleic acid amplification primer hybridises specifically to a nucleic acid sequence that is conserved in the SARS-CoV-2 nucleic acid, but not in other human coronavirus nucleic acid, wherein the nucleic acid sequence that is conserved in the SARS-CoV-2 nucleic acid is a nucleic acid sequence that is conserved in the ORF1ab gene or the nucleocapsid gene of SARS-CoV-2, wherein:

the forward and the reverse nucleic acid primers hybridize specifically to the nucleic acid sequence that is conserved in the ORF1ab gene of SARS-CoV-2, wherein the forward nucleic acid primer comprises the nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), or CATTACAGGTGGTGTTGTTCAGTT (SEQ ID NO: 4), and the reverse nucleic acid primer comprises the nucleic acid sequence of: CAATAGTCTGAACAACTGGTGT (SEQ ID NO: 5), CTGGTGTAAGTTCCATCTCT (SEQ ID NO: 6), or AGGTGACAATTTGTCCACCGAC (SEQ ID NO: 7); and/or the forward and reverse nucleic acid primers hybridize specifically to the nucleic acid sequence that is conserved in the nucleocapsid gene of SARS-CoV-2, wherein the forward nucleic acid primer comprises the nucleic acid sequence of: TAGTTGATGACCCGTGTCCT (SEQ ID NO: 14), and the reverse nucleic acid primer comprises the nucleic acid sequence of: TGGGGTCCATTATCAGACAT (SEQ ID NO: 15), CAACACGAACGTCATGATAC (SEQ ID NO: 16), or CATAGAACGAACAACGCAC (SEQ ID NO: 17);

wherein the reverse nucleic acid primer further comprises a promoter sequence for a DNA-dependent RNA polymerase at its 5'-end;

optionally wherein the forward and/or the reverse nucleic acid primer is up to 50 nucleotides long.

13. The method according to claim 1, wherein the method employs the use of a set of primers according to claim 12.

14. A set of oligonucleotides for amplifying SARS-CoV-2 nucleic acid by an isothermal nucleic acid amplification reaction, and for capturing and/or detecting a product of the amplification reaction, wherein the set of oligonucleotides comprises:

(i) a set of primers, wherein the set of primers comprises a forward nucleic acid amplification primer and a reverse nucleic acid amplification primer, wherein each nucleic acid amplification primer hybridises specifically to a nucleic acid sequence that is conserved in the SARS-CoV-2 nucleic acid, but not in other human coronavirus nucleic acid, wherein the nucleic acid sequence that is conserved in the SARS-CoV-2 nucleic acid is the nucleic acid sequence that is conserved in the ORF1ab gene or the nucleocapsid gene of SARS-CoV-2, wherein:

the forward and the reverse nucleic acid primers hybridize specifically to the nucleic acid sequence that is conserved in the ORF1ab gene of SARS-CoV-2, wherein the forward nucleic acid primer comprises the nucleic acid sequence of: CTGTTGGTCAACAAGACGGCA (SEQ ID NO: 1), GTCAACAAACTGTTGGTCAA (SEQ ID NO: 2), GTCAACAAACTGTTGGTCAACA (SEQ ID NO: 3), or CATTACAGGTGGTGTTGTTCAGTT (SEQ ID NO: 4), and the reverse nucleic acid primer comprises the nucleic acid sequence of: CAATAGTCTGAACAACTGGTGT (SEQ ID NO: 5), CTGGTGTAAGTTCCATCTCT (SEQ ID NO: 6), or AGGTGACAATTTGTCCACCGAC (SEQ ID NO: 7); and/or the forward and reverse nucleic acid primers hybridize specifically to the nucleic acid sequence that is conserved in the nucleocapsid gene of SARS-CoV-2, wherein the forward nucleic acid primer comprises the nucleic acid sequence of: TAGTTGATGACCCGTGTCCT (SEQ ID NO: 14), and the reverse nucleic acid primer comprises the nucleic acid sequence of: TGGGGTCCATTATCAGACAT (SEQ ID NO: 15), CAACACGAACGTCATGATAC (SEQ ID NO: 16), or CATAGAACGAACAACGCAC (SEQ ID NO: 17);

(ii) a nucleic acid capture probe, wherein the capture probe hybridises specifically to the nucleic acid sequence that is conserved in SARS-CoV-2 nucleic acid, but not in other human coronavirus nucleic acid; and/or (iii) a nucleic acid detector probe, wherein the detector probe hybridises specifically to the nucleic acid sequence that is conserved in SARS-CoV-2 nucleic acid, but not in other human coronavirus nucleic acid, wherein the detector probe comprises a detectable label for labelling a product of the isothermal nucleic acid amplification.

15. The method according to claim 4, wherein the method employs the set of oligonucleotides according to claim 14.

16. A set of oligonucleotides according to claim 14, wherein:

the forward and reverse nucleic acid primers hybridise specifically to the nucleic acid sequence that is conserved in the ORF1ab gene of SARS-CoV-2, and the capture probe hybridizes specifically to nucleic acid sequence that is conserved in the ORF1ab gene of SARS-CoV-2, wherein the capture probe comprises the nucleic acid of sequence of: GGCAGTGAGGACAATCAGCAACTAC (SEQ ID NO: 8), GAGGACAATCAGACAACTACTATTC (SEQ ID NO: 9), or ACCCGTCCTTGATTGGCTTG (SEQ ID NO: 10); and/or the forward and reverse nucleic acid primers hybridise specifically to the nucleic acid sequence that is conserved in the nucleocapsid gene of SARS-CoV-2, and the capture probe hybridizes specifically to the nucleic acid sequence that is conserved in the nucleocapsid gene of SARS-CoV-2 wherein the capture probe comprises the nucleic acid of sequence of: CTGGTTCTAAATCACCCATTCA (SEQ ID NO: 18);

optionally wherein the capture probe is up to 50 nucleotides long.

17. A set of oligonucleotides according to claim 14 or 16, wherein:

the forward and reverse nucleic acid primers hybridise specifically to the nucleic acid sequence that is conserved in the ORF1ab gene of SARS-CoV-2, and the detector probe hybridizes specifically to the nucleic acid sequence that is conserved in the ORF1ab gene of SARS-CoV-2, wherein the detector probe comprises the nucleic acid sequence of: CAAACAATTGTTGAGGTTCAACCTC (SEQ ID NO: 11), GAGGTTCAACCTCAATTAGAGATGG (SEQ ID NO: 12), or GGAAGGTGTAGAGTTTCTTAGAGAC (SEQ ID NO: 13); and/or the forward and reverse nucleic acid primers hybridise specifically to the nucleic acid sequence that is conserved in the nucleocapsid gene of SARS-CoV-2, and the detector probe hybridizes specifically to the nucleic acid sequence that is conserved in the nucleocapsid gene of SARS-CoV-2, wherein the detector probe comprises a nucleic acid sequence of: GAACCTAAATTGGGTAGTCTTGTAG (SEQ ID NO: 19) or GGAACCTAAATTGGGTAGTCTTG (SEQ ID NO: 20);

optionally wherein the detector probe is up to 50 nucleotides long.

18. A kit according to claim 7, which comprises a set of primers according to claim 12, or a set of oligonucleotides according to claim 14.

19. A method for determining whether a sample includes severe acute respiratory syndrome coronavirus 2 (SARS-CoV-2) nucleic acid, which comprises amplifying a nucleic acid of the sample, or amplifying a nucleic acid derived from the nucleic acid of the sample, by an amplification reaction using a set of forward and reverse nucleic acid amplification primers, which further comprises detecting a product of the amplification reaction by hybridizing the product to a nucleic acid detector probe, selected from (i)-(iii):

(i) the forward nucleic acid primer, the reverse nucleic acid primer, and the detector probe each hybridizes specifically to the nucleic acid sequence that is conserved in the ORF1ab gene of SARS-CoV-2, but not in other human coronavirus nucleic acid, wherein:

the forward nucleic acid primer hybridizes specifically to the nucleic acid sequence that is conserved in the ORF1ab gene of SARS-CoV-2;

the reverse nucleic acid primer hybridizes specifically to the nucleic acid sequence that is conserved in the ORF1ab gene of SARS-CoV-2; and the detector probe hybridizes specifically to the nucleic acid sequence that is conserved in the ORF1ab gene of SARS-CoV-2, wherein the detector probe comprises the nucleic acid sequence of: GAGGTTCAACCTCAATTAGAGATGG (SEQ ID NO: 12);

(ii) the forward nucleic acid primer, the revers nucleic acid primer, and the detector probe each hybridizes specifically to the nucleic acid sequence that is conserved in the nucleocapsid gene of SARS-CoV-2, but not in other human coronavirus nucleic acid, wherein:

the forward nucleic acid primer hybridizes specifically to the nucleic acid sequence that is conserved in the nucleocapsid gene of SARS-CoV-2;

the reverse nucleic acid primer hybridizes specifically to the nucleic acid sequence that is conserved in the nucleocapsid gene of SARS-CoV-2; and the detector probe hybridizes specifically to the nucleic acid sequence that is conserved in the nucleocapsid gene of SARS-CoV-2, wherein the detector probe comprises an oligonucleotide comprising the nucleic acid sequence of: CTGGTTCTAAATCACCCATTCA (SEQ ID NO: 18); or (iii) a combination of (i) and (ii).

20. A kit for determining whether a sample includes SARS-CoV-2 nucleic acid, which comprises:

a forward nucleic acid amplification primer and a reverse nucleic acid amplification primer, for amplifying a template nucleic acid by an amplification reaction, wherein each nucleic acid amplification primer hybridises specifically to the nucleic acid sequence that is conserved in the ORF1ab gene of SARS-CoV-2; and a nucleic acid capture probe, wherein the capture probe hybridises specifically to the nucleic acid sequence that is conserved in the ORF1ab gene of SARS-CoV-2; and/or a nucleic acid detector probe, wherein the detector probe hybridises specifically to the nucleic acid sequence that is conserved in the ORF1ab gene of SARS-CoV-2, wherein the detector probe comprises a detectable label for labelling a product of the nucleic acid amplification, wherein the kit comprises:

an oligonucleotide comprising the nucleic acid sequence of: GAGGACAATCAGACAACTACTATTC (SEQ ID NO: 9); and an oligonucleotide comprising the nucleic acid sequence of: GAGGTTCAACCTCAATTAGAGATGG (SEQ ID NO: 12).

* * * * *